United States Patent
Keogh et al.

(10) Patent No.: US 10,335,280 B2
(45) Date of Patent: Jul. 2, 2019

(54) METHOD FOR ABLATING TARGET TISSUE OF A PATIENT

(71) Applicant: Medtronic, Inc., Minneapolis, MN (US)

(72) Inventors: James R. Keogh, Maplewood, MN (US); Timothy R. Ryan, Shorewood, MN (US); Carol E. Eberhardt, Fullerton, CA (US); Mark T. Stewart, Minneapolis, MN (US); James R. Skarda, Lake Elmo, MN (US); Timothy G. Laske, Shoreview, MN (US); Alexander J. Hill, Blaine, MN (US); Jack D. Lemmon, St. Paul, MN (US); David E. Francischelli, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 338 days.

(21) Appl. No.: 15/098,494

(22) Filed: Apr. 14, 2016

(65) Prior Publication Data

US 2016/0302925 A1   Oct. 20, 2016

Related U.S. Application Data

(63) Continuation of application No. 14/174,268, filed on Feb. 6, 2014, now Pat. No. 9,949,831, which is a
(Continued)

(51) Int. Cl.
*A61N 7/02*      (2006.01)
*A61F 2/24*      (2006.01)
(Continued)

(52) U.S. Cl.
CPC .......... *A61F 2/2496* (2013.01); *A61B 5/0044* (2013.01); *A61B 5/1076* (2013.01);
(Continued)

(58) Field of Classification Search
CPC ...... A61B 18/1442; A61B 2017/00243; A61B 2018/00291; A61B 2018/00351;
(Continued)

(56) References Cited

U.S. PATENT DOCUMENTS

| 421,131 A | 2/1890 | Haughawout |
| 873,845 A | 12/1907 | Crow |

(Continued)

FOREIGN PATENT DOCUMENTS

| CN | 102551878 | 7/2012 |
| EP | 0167345 A1 | 1/1986 |

(Continued)

OTHER PUBLICATIONS

Rong et al., "Noninvasive Renal Denervation for Resistant Hypertension Using High-Intensity Focused Ultrasound." Hypertension, Oct. 2015, 66, 4 pages.
(Continued)

*Primary Examiner* — Ruth S Smith

(57) ABSTRACT

A method for treating a human patient includes emitting ultrasound energy from an ultrasound transducer positioned remotely from target tissue of the patient. The ultrasound transducer is positioned at a desired location relative to the patient and target tissue using location and imaging techniques. The method further includes focusing the ultrasound energy such that one or more focal points are directed to the target tissue of the patient and ablating the target tissue at each focal point. The target tissue is ablated via the focused ultrasound energy without ablating non-target tissue through
(Continued)

which the ultrasound energy passes between the ultrasound transducer and the one or more focal points.

18 Claims, 15 Drawing Sheets

Related U.S. Application Data continuation of application No. 13/585,622, filed on Aug. 14, 2012, now abandoned, which is a continuation of application No. 12/570,888, filed on Sep. 30, 2009, now Pat. No. 8,241,274, which is a continuation-in-part of application No. 11/298,282, filed on Dec. 9, 2005, now Pat. No. 8,221,402, which is a continuation-in-part of application No. 11/128,686, filed on May 13, 2005, now Pat. No. 7,706,882, which is a continuation-in-part of application No. 10/643,299, filed on Aug. 19, 2003, now Pat. No. 7,338,434, which is a continuation-in-part of application No. 10/464,213, filed on Jun. 18, 2003, now Pat. No. 6,936,046, which is a continuation-in-part of application No. 10/156,315, filed on May 28, 2002, now Pat. No. 7,507,235, which is a continuation of application No. 09/879,294, filed on Jun. 12, 2001, now Pat. No. 6,447,443, which is a continuation of application No. 09/629,194, filed on Jul. 31, 2000, now Pat. No. 6,595,934, which is a continuation-in-part of application No. 09/487,705, filed on Jan. 19, 2000, now abandoned.

(60) Provisional application No. 61/194,783, filed on Sep. 30, 2008, provisional application No. 60/571,182, filed on May 14, 2004, provisional application No. 60/424,243, filed on Nov. 6, 2002, provisional application No. 60/404,969, filed on Aug. 21, 2002, provisional application No. 60/286,952, filed on Apr. 26, 2001, provisional application No. 60/282,029, filed on Apr. 6, 2001, provisional application No. 60/263,739, filed on Jan. 24, 2001, provisional application No. 60/261,343, filed on Jan. 13, 2001.

(51) Int. Cl.
*A61B 5/00* (2006.01)
*A61B 5/107* (2006.01)
*A61B 8/00* (2006.01)
*A61B 34/20* (2016.01)
*A61B 90/00* (2016.01)
*A61B 18/14* (2006.01)
*A61B 17/00* (2006.01)
*A61B 18/00* (2006.01)

(52) U.S. Cl.
CPC ............ *A61B 5/6853* (2013.01); *A61B 8/445* (2013.01); *A61B 34/20* (2016.02); *A61B 90/37* (2016.02); *A61B 90/39* (2016.02); *A61F 2/2433* (2013.01); *A61N 7/02* (2013.01); *A61B 18/1442* (2013.01); *A61B 2017/00243* (2013.01); *A61B 2018/00291* (2013.01); *A61B 2018/00351* (2013.01); *A61B 2018/00577* (2013.01); *A61B 2034/2051* (2016.02); *A61B 2034/2063* (2016.02); *A61B 2090/378* (2016.02); *A61B 2090/397* (2016.02); *A61F 2210/009* (2013.01); *A61F 2250/0096* (2013.01)

(58) Field of Classification Search
CPC .. A61B 2018/00577; A61B 2034/2051; A61B 2034/2063; A61B 2090/378; A61B 2090/397; A61B 34/20; A61B 5/0044; A61B 5/1076; A61B 5/6853; A61B 8/445; A61B 90/37; A61B 90/39; A61F 2210/009; A61F 2250/0096; A61F 2/2433; A61F 2/2496; A61N 7/02
See application file for complete search history.

(56) References Cited

U.S. PATENT DOCUMENTS

| | | |
|---|---|---|
| 954,661 A | 4/1910 | Whitcomb |
| 3,409,013 A | 11/1968 | Berry |
| 3,540,431 A | 11/1970 | Mobin/Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,736,936 A | 6/1973 | Basiulis et al. |
| 3,755,823 A | 9/1973 | Hancock |
| 3,783,873 A | 1/1974 | Jacobs |
| 3,807,403 A | 4/1974 | Stumpf et al. |
| 3,823,575 A | 7/1974 | Parel |
| 3,827,436 A | 8/1974 | Stumpf et al. |
| 3,839,741 A | 10/1974 | Haller |
| 3,859,986 A | 1/1975 | Okada et al. |
| 3,868,956 A | 3/1975 | Alfidi et al. |
| 3,874,388 A | 4/1975 | Kinq et al. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 3,990,452 A | 11/1976 | Murry et al. |
| 4,018,227 A | 4/1977 | Walsh |
| 4,022,215 A | 5/1977 | Benson |
| 4,035,849 A | 7/1977 | Angell et al. |
| 4,049,002 A | 9/1977 | Kletschka et al. |
| 4,056,854 A | 11/1977 | Boretos et al. |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,106,129 A | 8/1978 | Carpentier et al. |
| 4,207,897 A | 6/1980 | Lloyd et al. |
| 4,222,126 A | 9/1980 | Boretos et al. |
| 4,233,690 A | 11/1980 | Akins |
| 4,248,224 A | 2/1981 | Jones |
| 4,265,694 A | 5/1981 | Boretos |
| 4,275,734 A | 6/1981 | Mitchner |
| 4,291,420 A | 9/1981 | Reul |
| 4,297,749 A | 11/1981 | Davis et al. |
| 4,306,561 A | 12/1981 | De Medinaceli |
| 4,339,831 A | 7/1982 | Johnson |
| 4,343,048 A | 8/1982 | Ross et al. |
| 4,345,340 A | 8/1982 | Rosen |
| 4,377,168 A | 3/1983 | Rzasa et al. |
| 4,419,389 A | 12/1983 | Gudkin et al. |
| 4,470,157 A | 9/1984 | Love |
| 4,501,030 A | 2/1985 | Lane |
| 4,508,122 A | 4/1985 | Gardineer et al. |
| 4,562,900 A | 1/1986 | Anderson |
| 4,574,803 A | 3/1986 | Storz |
| 4,580,568 A | 4/1986 | Gianturco |
| 4,592,340 A | 6/1986 | Boyles |
| 4,598,698 A | 7/1986 | Siegmund |
| 4,601,290 A | 7/1986 | Effron et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,658,828 A | 4/1987 | Dory |
| 4,662,885 A | 5/1987 | DiPisa, Jr. |
| 4,664,110 A | 5/1987 | Schanzlin |
| 4,665,906 A | 5/1987 | Jervis |

(56) References Cited

U.S. PATENT DOCUMENTS

| | | |
|---|---|---|
| 4,688,570 A | 8/1987 | Kramer et al. |
| 4,688,750 A | 8/1987 | Kramer et al. |
| 4,710,192 A | 12/1987 | Liotta et al. |
| 4,726,356 A | 2/1988 | Santilli et al. |
| 4,733,665 A | 3/1988 | Palmaz |
| 4,736,749 A | 4/1988 | Lundback |
| 4,777,951 A | 10/1988 | Cribier et al. |
| 4,779,611 A | 10/1988 | Grooters |
| 4,787,899 A | 11/1988 | Lazarus |
| 4,787,901 A | 11/1988 | Baykut |
| 4,796,629 A | 1/1989 | Grayzel |
| 4,807,633 A | 2/1989 | Fry |
| 4,815,470 A | 3/1989 | Curtis et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,887,605 A | 12/1989 | Angelsen et al. |
| 4,909,252 A | 3/1990 | Goldberger |
| 4,917,096 A | 4/1990 | Engelhart et al. |
| 4,917,102 A | 4/1990 | Miller et al. |
| 4,922,905 A | 5/1990 | Strecker |
| 4,936,281 A | 6/1990 | Stasz |
| 4,946,460 A | 8/1990 | Merry |
| 4,951,653 A | 8/1990 | Fry et al. |
| 4,954,126 A | 9/1990 | Wallsten |
| 4,955,365 A | 9/1990 | Fry et al. |
| 4,955,896 A | 9/1990 | Freeman |
| 4,966,604 A | 10/1990 | Reiss |
| 4,973,300 A | 11/1990 | Wright |
| 4,979,939 A | 12/1990 | Shiber |
| RE33,590 E | 1/1991 | Dory |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,010,886 A | 4/1991 | Passafaro et al. |
| 5,013,312 A | 5/1991 | Parins et al. |
| 5,026,366 A | 6/1991 | Leckrone |
| 5,029,574 A | 7/1991 | Shimamura et al. |
| 5,032,128 A | 7/1991 | Alonso |
| 5,033,456 A | 7/1991 | Pell et al. |
| 5,036,855 A | 8/1991 | Fry et al. |
| 5,037,434 A | 8/1991 | Lane |
| 5,044,165 A | 9/1991 | Linner et al. |
| 5,047,041 A | 9/1991 | Samuels |
| 5,054,470 A | 10/1991 | Fry et al. |
| 5,059,177 A | 10/1991 | Towne et al. |
| 5,061,273 A | 10/1991 | Yock |
| 5,065,761 A | 11/1991 | Pell |
| 5,080,101 A | 1/1992 | Dory |
| 5,080,102 A | 1/1992 | Dory |
| 5,080,660 A | 1/1992 | Buelina |
| 5,085,635 A | 2/1992 | Craaa |
| 5,089,015 A | 2/1992 | Ross |
| 5,096,587 A | 3/1992 | Kline/Schoder et al. |
| 5,100,388 A | 3/1992 | Behl |
| 5,108,390 A | 4/1992 | Potocky et al. |
| 5,109,859 A | 5/1992 | Jenkins |
| 5,117,832 A | 6/1992 | Sanghvi et al. |
| 5,139,496 A | 8/1992 | Hed |
| 5,134,988 A | 9/1992 | Pell et al. |
| 5,143,074 A | 9/1992 | Dory |
| 5,150,711 A | 9/1992 | Dory |
| 5,150,712 A | 9/1992 | Dory |
| 5,152,771 A | 10/1992 | Sabbaqhian et al. |
| 5,158,070 A | 10/1992 | Dory |
| 5,161,547 A | 11/1992 | Tower |
| 5,163,953 A | 11/1992 | Vince |
| 5,167,628 A | 12/1992 | Boyles |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,217,483 A | 7/1993 | Tower |
| 5,224,943 A | 7/1993 | Goddard |
| 5,228,923 A | 7/1993 | Hed |
| 5,232,445 A | 8/1993 | Bonzel |
| 5,232,516 A | 8/1993 | Baust et al. |
| 5,247,935 A | 9/1993 | Cline et al. |
| 5,256,132 A | 10/1993 | Snyders |
| 5,267,954 A | 12/1993 | Nita |
| 5,269,291 A | 12/1993 | Carter |
| 5,269,297 A | 12/1993 | Weng et al. |
| 5,272,909 A | 12/1993 | Nguyen et al. |
| 5,295,484 A | 3/1994 | Marcus et al. |
| 5,295,958 A | 3/1994 | Shturman |
| 5,304,115 A | 4/1994 | Pflueger et al. |
| 5,312,328 A | 5/1994 | Nita et al. |
| 5,318,014 A | 6/1994 | Carter |
| 5,324,255 A | 6/1994 | Passafaro et al. |
| 5,326,342 A | 7/1994 | Pflueger et al. |
| 5,327,774 A | 7/1994 | Nguyen et al. |
| 5,336,252 A | 8/1994 | Choen |
| 5,342,292 A | 8/1994 | Nita et al. |
| 5,350,398 A | 9/1994 | Pavcnik et al. |
| 5,354,258 A | 10/1994 | Dory |
| 5,368,557 A | 11/1994 | Nita et al. |
| 5,368,558 A | 11/1994 | Nita |
| 5,370,685 A | 12/1994 | Stevens |
| 5,372,138 A | 12/1994 | Crowley et al. |
| 5,380,274 A | 1/1995 | Nita |
| 5,382,228 A | 1/1995 | Nita et al. |
| 5,383,874 A | 1/1995 | Jackson et al. |
| 5,389,106 A | 2/1995 | Tower |
| 5,391,197 A | 2/1995 | Burdette |
| 5,397,301 A | 3/1995 | Pflueger et al. |
| 5,397,351 A | 3/1995 | Pavcnik et al. |
| 5,405,318 A | 4/1995 | Nita |
| 5,409,002 A | 4/1995 | Pell |
| 5,415,633 A | 5/1995 | Lazarus et al. |
| 5,417,672 A | 5/1995 | Nita et al. |
| 5,423,812 A | 6/1995 | Ellman et al. |
| 5,427,118 A | 6/1995 | Nita et al. |
| 5,431,621 A | 7/1995 | Dory |
| 5,431,663 A | 7/1995 | Carter |
| 5,431,676 A | 7/1995 | Dubrul et al. |
| 5,443,446 A | 8/1995 | Shturman |
| 5,447,509 A | 9/1995 | Mills et al. |
| 5,452,733 A | 9/1995 | Sterman et al. |
| 5,456,662 A | 10/1995 | Edwards |
| 5,471,988 A | 12/1995 | Fujio et al. |
| 5,474,530 A | 12/1995 | Passafaro et al. |
| 5,478,330 A | 12/1995 | Imran et al. |
| 5,480,424 A | 1/1996 | Cox |
| 5,489,294 A | 2/1996 | Mcvenes et al. |
| 5,489,297 A | 2/1996 | Duran |
| 5,492,126 A | 2/1996 | Hennige et al. |
| 5,496,346 A | 3/1996 | Horzewski et al. |
| 5,500,014 A | 3/1996 | Quijano et al. |
| 5,501,655 A | 3/1996 | Hennige et al. |
| 5,507,767 A | 4/1996 | Maeda et al. |
| 5,514,131 A | 5/1996 | Edwards |
| 5,520,188 A | 5/1996 | Nita et al. |
| 5,540,656 A | 7/1996 | Pflueger et al. |
| 5,542,917 A | 8/1996 | Nita et al. |
| 5,545,195 A | 8/1996 | Lennox et al. |
| 5,545,200 A | 8/1996 | West et al. |
| 5,545,209 A | 8/1996 | Roberts et al. |
| 5,545,211 A | 8/1996 | An et al. |
| 5,545,214 A | 8/1996 | Stevens |
| 5,549,661 A | 8/1996 | Kordis |
| 5,553,198 A | 9/1996 | Wang et al. |
| 5,554,185 A | 9/1996 | Block et al. |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |

(56) References Cited

U.S. PATENT DOCUMENTS

| | | | |
|---|---|---|---|
| 5,575,766 | A | 11/1996 | Swartz et al. |
| 5,575,788 | A | 11/1996 | Baker |
| 5,575,810 | A | 11/1996 | Swanson et al. |
| 5,575,818 | A | 11/1996 | Pinchuk |
| 5,578,007 | A | 11/1996 | Imran |
| 5,580,922 | A | 12/1996 | Park et al. |
| 5,588,432 | A | 12/1996 | Crowley |
| 5,590,657 | A | 1/1997 | Cain et al. |
| 5,591,195 | A | 1/1997 | Taheri et al. |
| 5,601,526 | A | 2/1997 | Chapelon |
| 5,607,462 | A | 3/1997 | Imran |
| 5,609,606 | A | 3/1997 | O'Boyle |
| 5,609,626 | A | 3/1997 | Quijano et al. |
| 5,617,854 | A | 4/1997 | Munsif |
| 5,620,479 | A | 4/1997 | Diederich |
| 5,624,439 | A | 4/1997 | Edwards |
| 5,630,837 | A | 5/1997 | Crowley |
| 5,637,090 | A | 6/1997 | McGee et al. |
| 5,643,197 | A | 7/1997 | McGee et al. |
| 5,645,559 | A | 7/1997 | Hachtman et al. |
| 5,656,029 | A | 8/1997 | Brucker et al. |
| 5,657,429 | A | 8/1997 | Wang et al. |
| 5,658,278 | A | 8/1997 | Imran et al. |
| 5,665,115 | A | 9/1997 | Craaa |
| 5,667,523 | A | 9/1997 | Bynon et al. |
| 5,671,747 | A | 9/1997 | Connor |
| 5,673,695 | A | 10/1997 | McGee et al. |
| 5,674,191 | A | 10/1997 | Edwards |
| 5,674,277 | A | 10/1997 | Freitaq |
| 5,676,662 | A | 10/1997 | Fleischhacker et al. |
| 5,676,692 | A | 10/1997 | Sanghvi |
| 5,695,498 | A | 12/1997 | Tower |
| 5,702,368 | A | 12/1997 | Stevens et al. |
| 5,707,349 | A | 1/1998 | Edwards |
| 5,713,953 | A | 2/1998 | Vallana et al. |
| 5,716,417 | A | 2/1998 | Girard et al. |
| 5,718,702 | A | 2/1998 | Edwards |
| 5,720,719 | A | 2/1998 | McMillan et al. |
| 5,728,094 | A | 3/1998 | Edwards |
| 5,730,719 | A | 3/1998 | Edwards |
| 5,733,315 | A | 3/1998 | Burdette et al. |
| 5,735,280 | A | 4/1998 | Sherman |
| 5,738,114 | A | 4/1998 | Edwards |
| 5,743,904 | A | 4/1998 | Edwards |
| 5,746,224 | A | 5/1998 | Edwards |
| 5,749,890 | A | 5/1998 | Shaknovich |
| 5,762,066 | A | 6/1998 | Law et al. |
| 5,782,809 | A | 7/1998 | Umeno et al. |
| 5,797,849 | A | 8/1998 | Vesely et al. |
| 5,797,960 | A | 8/1998 | Stevens et al. |
| 5,799,661 | A | 9/1998 | Boyd et al. |
| 5,800,379 | A | 9/1998 | Edwards |
| 5,800,429 | A | 9/1998 | Pomeranz et al. |
| 5,800,508 | A | 9/1998 | Goicoechea et al. |
| 5,807,308 | A | 9/1998 | Edwards |
| 5,817,049 | A | 10/1998 | Edwards |
| 5,823,197 | A | 10/1998 | Edwards |
| 5,824,041 | A | 10/1998 | Lenker et al. |
| 5,824,043 | A | 10/1998 | Cottone, Jr. |
| 5,824,053 | A | 10/1998 | Khosravi et al. |
| 5,824,056 | A | 10/1998 | Rosenberg |
| 5,824,061 | A | 10/1998 | Quijano et al. |
| 5,824,064 | A | 10/1998 | Taheri |
| 5,827,203 | A | 10/1998 | Nita |
| 5,827,277 | A | 10/1998 | Edwards |
| 5,830,213 | A | 11/1998 | Panescu et al. |
| 5,840,030 | A | 11/1998 | Ferekpetric et al. |
| 5,843,158 | A | 12/1998 | Lenker et al. |
| 5,844,349 | A | 12/1998 | Oakley |
| 5,846,187 | A | 12/1998 | Wells et al. |
| 5,846,191 | A | 12/1998 | Wells et al. |
| 5,848,969 | A | 12/1998 | Panescu et al. |
| 5,849,028 | A | 12/1998 | Chen |
| 5,855,597 | A | 1/1999 | Jayaraman |
| 5,855,601 | A | 1/1999 | Bessler et al. |
| 5,860,966 | A | 1/1999 | Tower |
| 5,861,028 | A | 1/1999 | Angell |
| 5,865,801 | A | 2/1999 | Houser |
| 5,868,783 | A | 2/1999 | Tower |
| 5,871,523 | A | 2/1999 | Fleischman et al. |
| 5,871,524 | A | 2/1999 | Knowloton |
| 5,871,525 | A | 2/1999 | Edwards et al. |
| 5,873,902 | A | 2/1999 | Sanghvi et al. |
| 5,876,399 | A | 3/1999 | Chia et al. |
| 5,876,448 | A | 3/1999 | Thompson et al. |
| 5,879,295 | A | 3/1999 | Ockuly et al. |
| 5,879,329 | A | 3/1999 | Edwards |
| 5,881,732 | A | 3/1999 | Sung et al. |
| 5,882,302 | A | 3/1999 | Driscoll, Jr. et al. |
| 5,885,278 | A | 3/1999 | Fleischman |
| 5,888,201 | A | 3/1999 | Stinson et al. |
| 5,891,191 | A | 4/1999 | Stinson |
| 5,893,848 | A | 4/1999 | Negus et al. |
| 5,893,949 | A | 4/1999 | Pomeranz et al. |
| 5,895,356 | A | 4/1999 | Andrus et al. |
| 5,904,711 | A | 5/1999 | Flom et al. |
| 5,906,587 | A | 5/1999 | Zimmon |
| 5,906,606 | A | 5/1999 | Ghee et al. |
| 5,906,619 | A | 5/1999 | Olson et al. |
| 5,907,893 | A | 6/1999 | Zadno/Azizi et al. |
| 5,908,029 | A | 6/1999 | Knudson et al. |
| 5,913,842 | A | 6/1999 | Boyd et al. |
| 5,916,192 | A | 6/1999 | Nita et al. |
| 5,916,213 | A | 6/1999 | Haissaguerre et al. |
| 5,916,214 | A | 6/1999 | Cosio et al. |
| 5,921,982 | A | 7/1999 | Lesh et al. |
| 5,925,063 | A | 7/1999 | Khosravi |
| 5,927,284 | A | 7/1999 | Borst et al. |
| 5,928,169 | A | 7/1999 | Schitzle et al. |
| 5,928,191 | A | 7/1999 | Houser et al. |
| 5,931,810 | A | 8/1999 | Grabek |
| 5,931,848 | A | 8/1999 | Saadat |
| 5,934,284 | A | 8/1999 | Plaia et al. |
| 5,935,075 | A | 8/1999 | Casscells et al. |
| 5,938,608 | A | 8/1999 | Bieger et al. |
| 5,944,738 | A | 8/1999 | Amplatz et al. |
| 5,954,766 | A | 9/1999 | Zadno/Azizi et al. |
| 5,957,882 | A | 9/1999 | Nita et al. |
| 5,957,941 | A | 9/1999 | Ream |
| 5,957,949 | A | 9/1999 | Leonhardt et al. |
| 5,967,984 | A | 10/1999 | Chu et al. |
| 5,968,068 | A | 10/1999 | Dehdashtian et al. |
| 5,971,980 | A | 10/1999 | Sherman |
| 5,972,013 | A | 10/1999 | Schmitdt |
| 5,978,713 | A | 11/1999 | Varney |
| 5,984,881 | A | 11/1999 | Ishibashi et al. |
| 5,984,882 | A | 11/1999 | Rosenschein et al. |
| 5,984,957 | A | 11/1999 | Laptewicz, Jr. et al. |
| 5,989,208 | A | 11/1999 | Nita |
| 5,993,447 | A | 11/1999 | Blewett et al. |
| 5,997,497 | A | 12/1999 | Nita et al. |
| 5,997,573 | A | 12/1999 | Quijano et al. |
| 6,007,499 | A | 12/1999 | Martin et al. |
| 6,007,514 | A | 12/1999 | Nita |
| 6,009,877 | A | 1/2000 | Edwards |
| 6,012,457 | A | 1/2000 | Lesh |
| 6,013,033 | A | 1/2000 | Berger et al. |
| 6,016,811 | A | 1/2000 | Knopp et al. |
| 6,019,722 | A | 2/2000 | Spence et al. |
| 6,022,309 | A | 2/2000 | Celliers et al. |
| 6,022,370 | A | 2/2000 | Tower |
| 6,024,740 | A | 2/2000 | Lesh |
| 6,026,816 | A | 2/2000 | McMillan et al. |
| 6,027,525 | A | 2/2000 | Suh et al. |
| 6,029,671 | A | 2/2000 | Stevens et al. |
| 6,032,675 | A | 3/2000 | Rubinsky |
| 6,035,378 | A | 3/2000 | James |
| 6,039,694 | A | 3/2000 | Larson et al. |
| 6,042,556 | A * | 3/2000 | Beach ............... A61N 7/02 600/437 |
| 6,042,566 | A | 3/2000 | Beach et al. |
| 6,042,589 | A | 3/2000 | Marianne |
| 6,042,598 | A | 3/2000 | Tsuqita et al. |
| 6,051,014 | A | 4/2000 | Jang |

(56) References Cited

U.S. PATENT DOCUMENTS

| | | |
|---|---|---|
| 6,053,873 A | 4/2000 | Govari et al. |
| 6,056,744 A | 5/2000 | Edwards |
| 6,059,809 A | 5/2000 | Amor et al. |
| 6,060,454 A | 5/2000 | Duhaylongsod |
| 6,066,096 A | 5/2000 | Smith et al. |
| 6,071,279 A | 6/2000 | Oakley |
| 6,081,749 A | 6/2000 | Ingle et al. |
| 6,083,159 A | 7/2000 | Driscoll et al. |
| 6,096,033 A | 8/2000 | Tu et al. |
| 6,110,201 A | 8/2000 | Quijano et al. |
| 6,113,559 A | 9/2000 | Klopotek |
| 6,113,592 A | 9/2000 | Taylor |
| 6,117,101 A | 9/2000 | Diederich et al. |
| 6,117,128 A | 9/2000 | Gregory |
| 6,120,496 A | 9/2000 | Whayne et al. |
| 6,126,657 A | 10/2000 | Edwards et al. |
| 6,135,971 A | 10/2000 | Hutchinson et al. |
| 6,142,991 A | 11/2000 | Schatzberger |
| 6,142,993 A | 11/2000 | Whayne et al. |
| 6,146,366 A | 11/2000 | Schachar |
| 6,149,596 A | 11/2000 | Bancroft |
| 6,152,920 A | 11/2000 | Thompson et al. |
| 6,156,009 A | 12/2000 | Grabeck |
| 6,159,201 A | 12/2000 | Hamilton et al. |
| 6,159,239 A | 12/2000 | Greenhalqh |
| 6,161,543 A | 12/2000 | Cox et al. |
| 6,162,195 A | 12/2000 | Igo et al. |
| 6,162,208 A | 12/2000 | Hipps |
| 6,162,245 A | 12/2000 | Javaraman |
| 6,171,335 B1 | 1/2001 | Wheatley et al. |
| 6,174,280 B1 | 1/2001 | Oneda et al. |
| 6,174,307 B1 | 1/2001 | Daniel et al. |
| 6,190,353 B1 | 2/2001 | Makower et al. |
| 6,190,381 B1 | 2/2001 | Edwards et al. |
| 6,200,266 B1 | 3/2001 | Shokrollahi |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,216,704 B1 | 4/2001 | Ingle et al. |
| 6,217,528 B1 | 4/2001 | Koblish et al. |
| 6,217,576 B1 | 4/2001 | Tu et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,224,592 B1 | 5/2001 | Eggers et al. |
| 6,231,516 B1 | 5/2001 | Keilman et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,241,753 B1 | 6/2001 | Knowlton |
| 6,241,757 B1 | 6/2001 | An et al. |
| 6,245,020 B1 | 6/2001 | Moore et al. |
| 6,245,064 B1 | 6/2001 | Lesh et al. |
| 6,245,102 B1 | 6/2001 | Jayaraman |
| 6,246,077 B1 | 6/2001 | Suorsa et al. |
| 6,254,598 B1 | 7/2001 | Edwards et al. |
| 6,254,599 B1 | 7/2001 | Lesh et al. |
| 6,258,087 B1 | 7/2001 | Edwards et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,266,564 B1 | 7/2001 | Hill et al. |
| 6,277,555 B1 | 8/2001 | Duran et al. |
| 6,283,935 B1 | 9/2001 | Laufer et al. |
| 6,296,619 B1 | 10/2001 | Brisken et al. |
| 6,296,639 B1 | 10/2001 | Truckai et al. |
| 6,299,637 B1 | 10/2001 | Shaolia et al. |
| 6,309,355 B1 * | 10/2001 | Cain ............... A61B 17/22004 600/439 |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,732 B1 | 11/2001 | Suorsa et al. |
| 6,315,741 B1 | 11/2001 | Martin et al. |
| 6,324,843 B1 | 12/2001 | Yasuda et al. |
| 6,325,769 B1 | 12/2001 | Klopotek |
| 6,328,688 B1 | 12/2001 | Borst |
| 6,331,158 B1 | 12/2001 | Hu et al. |
| 6,332,881 B1 | 12/2001 | Carner et al. |
| 6,336,898 B1 | 1/2002 | Vorst |
| 6,350,229 B1 | 2/2002 | Borst |
| 6,421,559 B1 | 2/2002 | Pearlman |
| 6,353,751 B1 | 3/2002 | Swanson et al. |
| 6,361,531 B1 | 3/2002 | Hissong |
| 6,363,279 B1 | 3/2002 | Ben/Haim et al. |
| 6,364,826 B1 | 4/2002 | Borst |
| 6,364,840 B1 | 4/2002 | Crowley |
| 6,368,275 B1 | 4/2002 | Erb et al. |
| 6,371,906 B1 | 4/2002 | Borst |
| 6,371,955 B1 | 4/2002 | Fuimanono et al. |
| 6,374,132 B1 | 4/2002 | Acker et al. |
| 6,383,151 B1 | 5/2002 | Diederich et al. |
| 6,385,472 B1 | 5/2002 | Hall et al. |
| 6,394,096 B1 | 5/2002 | Constantz |
| 6,394,948 B1 | 5/2002 | Borst |
| 6,394,956 B1 | 5/2002 | Chandrasekaran et al. |
| 6,398,780 B1 | 6/2002 | Farley et al. |
| 6,398,792 B1 | 6/2002 | O'Conner |
| 6,409,720 B1 | 6/2002 | Hissong et al. |
| 6,413,254 B1 | 7/2002 | Hissong |
| 6,419,648 B1 | 7/2002 | Vitek et al. |
| 6,425,867 B1 | 7/2002 | Vaezy et al. |
| 6,429,217 B1 | 8/2002 | Puskas |
| 6,430,426 B2 | 8/2002 | Avitall |
| 6,432,067 B1 | 8/2002 | Martin et al. |
| 6,440,127 B2 | 8/2002 | McGovern et al. |
| 6,440,164 B1 | 8/2002 | DiMatteo et al. |
| 6,485,489 B2 | 8/2002 | Teirstein et al. |
| 6,447,443 B1 | 9/2002 | Keogh et al. |
| 6,447,507 B1 | 9/2002 | Barnarek et al. |
| 6,451,013 B1 | 9/2002 | Bays et al. |
| 6,451,044 B1 | 9/2002 | Naghavi et al. |
| 6,454,737 B1 | 9/2002 | Nita et al. |
| 6,454,757 B1 | 9/2002 | Nita et al. |
| 6,395,015 B1 | 10/2002 | Borst |
| 6,459,926 B1 | 10/2002 | Nowlin et al. |
| 6,461,314 B1 | 10/2002 | Pant et al. |
| 6,461,382 B1 | 10/2002 | Cao |
| 6,461,956 B1 | 10/2002 | Patterson |
| 6,464,629 B1 | 10/2002 | Borst |
| 6,468,265 B1 | 10/2002 | Evans |
| 6,468,303 B1 | 10/2002 | Amplatz et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,239 B1 | 11/2002 | Campbell et al. |
| 6,477,396 B1 | 11/2002 | Mest et al. |
| 6,479,523 B1 | 11/2002 | Puskas |
| 6,482,228 B1 | 11/2002 | Norred |
| 6,484,052 B1 | 11/2002 | Visuri et al. |
| 6,484,727 B1 | 11/2002 | Vaska et al. |
| 6,487,446 B1 | 11/2002 | Hill et al. |
| 6,488,704 B1 | 12/2002 | Connelly et al. |
| 6,492,762 B1 | 12/2002 | Pant et al. |
| 6,494,891 B1 | 12/2002 | Cornish et al. |
| 6,494,909 B2 | 12/2002 | Greenhalqh |
| 6,500,133 B2 | 12/2002 | Martin et al. |
| 6,500,174 B1 | 12/2002 | Maguire et al. |
| 6,501,978 B2 | 12/2002 | Wagshul et al. |
| 6,503,272 B2 | 1/2003 | Dueriq et al. |
| 6,508,765 B2 | 1/2003 | Suorsa et al. |
| 6,508,774 B1 | 1/2003 | Acker et al. |
| 6,508,833 B2 | 1/2003 | Pavcnik et al. |
| 6,589,238 B2 | 1/2003 | Edwards et al. |
| 6,517,563 B1 | 2/2003 | Paolitto et al. |
| 6,527,767 B2 | 3/2003 | Wang |
| 6,527,769 B2 | 3/2003 | Langberg et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,532,388 B1 | 3/2003 | Hill et al. |
| 6,542,774 B2 | 4/2003 | Hill et al. |
| 6,546,272 B1 | 4/2003 | MacKinnon et al. |

(56) References Cited

U.S. PATENT DOCUMENTS

| | | |
|---|---|---|
| 6,547,788 B1 | 4/2003 | Maguire et al. |
| 6,558,381 B2 | 5/2003 | Ingle et al. |
| 6,562,031 B2 | 5/2003 | Chandrasekaran et al. |
| 6,562,058 B2 | 5/2003 | Sequin et al. |
| 6,569,109 B2 | 5/2003 | Sakurai et al. |
| 6,569,196 B1 | 5/2003 | Vesely |
| 6,575,956 B1 | 6/2003 | Hissong et al. |
| 6,585,758 B1 | 7/2003 | Chouinard et al. |
| 6,592,526 B1 | 7/2003 | Lenker |
| 6,592,546 B1 | 7/2003 | Barbut et al. |
| 6,599,256 B1 | 7/2003 | Acker et al. |
| 6,605,084 B2 | 8/2003 | Acker et al. |
| 6,605,112 B1 | 8/2003 | Moll et al. |
| 6,610,054 B1 | 8/2003 | Edwards et al. |
| 6,613,077 B2 | 9/2003 | Gilligan et al. |
| 6,622,604 B1 | 9/2003 | Chouinard et al. |
| 6,626,855 B1 | 9/2003 | Weng et al. |
| 6,628,987 B1 | 9/2003 | Hill et al. |
| 6,629,534 B1 | 10/2003 | St. Goar et al. |
| 6,635,054 B2 | 10/2003 | Fjield et al. |
| 6,635,068 B1 | 10/2003 | Dubrul et al. |
| 6,641,579 B1 | 11/2003 | Bernardi et al. |
| 6,645,199 B1 | 11/2003 | Jenkins et al. |
| 6,645,202 B1 | 11/2003 | Vaska et al. |
| 6,652,515 B1 | 11/2003 | Maguire et al. |
| 6,652,571 B1 | 11/2003 | White et al. |
| 6,656,136 B1 | 12/2003 | Weng et al. |
| 6,656,213 B2 | 12/2003 | Solem |
| 6,656,950 B2 | 12/2003 | Puskas |
| 6,663,663 B2 | 12/2003 | Kim et al. |
| 6,669,655 B1 | 12/2003 | Acker et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,685,739 B2 | 2/2004 | DiMatteo et al. |
| 6,689,086 B1 | 2/2004 | Nita et al. |
| 6,689,128 B2 | 2/2004 | Sliwa et al. |
| 6,689,144 B2 | 2/2004 | Gerberdinq |
| 6,689,164 B1 | 2/2004 | Sequin |
| 6,690,973 B2 | 2/2004 | Hill et al. |
| 6,692,490 B1 | 2/2004 | Edwards |
| 6,692,512 B2 | 2/2004 | Janq |
| 6,692,513 B2 | 2/2004 | Streeter |
| 6,695,878 B2 | 2/2004 | McGuckin, Jr. et al. |
| 6,702,748 B1 | 3/2004 | Nita et al. |
| 6,702,811 B2 | 3/2004 | Stewart et al. |
| 6,702,851 B1 | 3/2004 | Chinn et al. |
| 6,711,429 B1 | 3/2004 | Gilboa et al. |
| 6,808,524 B2 | 3/2004 | Lopath et al. |
| 6,719,694 B2 | 4/2004 | Weng et al. |
| 6,719,789 B2 | 4/2004 | Cox |
| 6,723,064 B2 | 4/2004 | Babaev |
| 6,730,377 B2 | 5/2004 | Wanq |
| 6,733,525 B2 | 5/2004 | Yang et al. |
| 6,735,471 B2 | 5/2004 | Hill et al. |
| 6,736,846 B2 | 5/2004 | Cox |
| 6,740,028 B2 | 5/2004 | Borst |
| 6,746,401 B2 | 6/2004 | Panescu |
| 6,752,828 B2 | 6/2004 | Thornton |
| 6,755,780 B2 | 6/2004 | Borst |
| 6,758,847 B2 | 7/2004 | Maguire |
| 6,758,855 B2 | 7/2004 | Fulton, III et al. |
| 6,763,261 B2 | 7/2004 | Casscells et al. |
| 6,763,722 B2 | 7/2004 | Fjield et al. |
| 6,769,433 B2 | 8/2004 | Zikorus et al. |
| 6,769,434 B2 | 8/2004 | Liddicoat et al. |
| 6,770,070 B1 | 8/2004 | Balbierz |
| 6,773,433 B2 | 8/2004 | Stewart et al. |
| 6,778,854 B2 | 8/2004 | Puskas |
| 6,780,183 B2 | 8/2004 | Jimenez et al. |
| 6,786,925 B1 | 9/2004 | Schoon et al. |
| 6,787,974 B2 | 9/2004 | Fjield et al. |
| 6,792,979 B2 | 9/2004 | Konya et al. |
| 6,797,002 B2 | 9/2004 | Spence et al. |
| 6,802,840 B2 | 10/2004 | Chin et al. |
| 6,805,128 B1 | 10/2004 | Pless et al. |
| 6,807,444 B2 | 10/2004 | Tu et al. |
| RE38,654 E | 11/2004 | Hill et al. |
| 6,821,297 B2 | 11/2004 | Snyders |
| 6,824,516 B2 | 11/2004 | Batten et al. |
| 6,830,575 B2 | 12/2004 | Stenzel et al. |
| 6,830,585 B1 | 12/2004 | Artof et al. |
| 6,840,936 B2 | 1/2005 | Sliwa et al. |
| 6,846,325 B2 | 1/2005 | Liddicoat |
| RE38,705 E | 2/2005 | Hill et al. |
| 6,849,075 B2 | 2/2005 | Bertolero et al. |
| 6,855,123 B2 | 2/2005 | Nita |
| 6,866,650 B2 | 3/2005 | Stevens et al. |
| 6,869,431 B2 | 3/2005 | Maguire et al. |
| 6,872,223 B2 | 3/2005 | Roberts et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,898,454 B2 | 5/2005 | Atalar et al. |
| 6,904,318 B2 | 6/2005 | Hill et al. |
| 6,911,026 B1 | 6/2005 | Hall et al. |
| 6,912,419 B2 | 6/2005 | Hill et al. |
| 6,913,600 B2 | 7/2005 | Valley et al. |
| 6,929,632 B2 | 8/2005 | Nita et al. |
| 6,929,653 B2 | 8/2005 | Streeter |
| 6,936,001 B1 | 8/2005 | Snow |
| 6,936,046 B2 | 8/2005 | Hissong |
| 6,936,066 B2 | 8/2005 | Palmaz et al. |
| 6,939,365 B1 | 9/2005 | Foqarty et al. |
| 6,942,620 B2 | 9/2005 | Nita et al. |
| 6,942,677 B2 | 9/2005 | Nita et al. |
| 6,949,097 B2 | 9/2005 | Stewart et al. |
| 6,949,098 B2 | 9/2005 | Mulier |
| 6,951,571 B1 | 10/2005 | Srivastava |
| 6,954,977 B2 | 10/2005 | Maguire et al. |
| 6,966,908 B2 | 11/2005 | Maguire et al. |
| 6,974,456 B2 | 12/2005 | Edwards et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,098 B2 | 5/2006 | Farley et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,048,683 B2 | 5/2006 | Borst |
| 7,058,447 B2 | 6/2006 | Hill et al. |
| 7,063,666 B2 | 6/2006 | Weng et al. |
| 7,066,895 B2 | 6/2006 | Podany |
| 7,072,720 B2 | 7/2006 | Puskas |
| 7,083,614 B2 | 8/2006 | Fjield et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,137,963 B2 | 11/2006 | Nita et al. |
| 7,142,910 B2 | 11/2006 | Puskas |
| 7,147,663 B1 | 12/2006 | Berq et al. |
| 7,153,315 B2 | 12/2006 | Miller |
| 7,153,324 B2 | 12/2006 | Case et al. |
| 7,155,271 B2 | 12/2006 | Halperin et al. |
| 7,160,319 B2 | 1/2007 | Chouinard et al. |
| 7,165,551 B2 | 1/2007 | Edwards et al. |
| 7,175,656 B2 | 2/2007 | Khairkhahan |
| 7,184,828 B2 | 2/2007 | Hill et al. |
| 7,184,829 B2 | 2/2007 | Hill et al. |
| 7,186,265 B2 | 3/2007 | Sharkawy et al. |
| 7,189,229 B2 | 3/2007 | Lopath et al. |
| 7,195,641 B2 | 3/2007 | Palmaz et al. |
| 7,201,749 B2 | 4/2007 | Govari et al. |
| 7,201,761 B2 | 4/2007 | Woolfson et al. |
| 7,220,233 B2 | 5/2007 | Nita et al. |
| 7,220,239 B2 | 5/2007 | Wilson et al. |
| 7,241,736 B2 | 7/2007 | Hunter et al. |

(56) References Cited

U.S. PATENT DOCUMENTS

| | | |
|---|---|---|
| 7,247,141 B2 | 7/2007 | Makin et al. |
| 7,294,125 B2 | 11/2007 | Phalen et al. |
| 7,297,131 B2 | 11/2007 | Nita |
| 7,300,457 B2 | 11/2007 | Palmaz |
| 7,300,463 B2 | 11/2007 | Liddicoat |
| 7,313,430 B2 | 12/2007 | Urquhart et al. |
| 7,316,706 B2 | 1/2008 | Bloom et al. |
| 7,326,201 B2 | 2/2008 | Fjield et al. |
| 7,329,278 B2 | 2/2008 | Sequin et al. |
| 7,335,180 B2 | 2/2008 | Nita et al. |
| 7,335,218 B2 | 2/2008 | Wilson et al. |
| 7,338,434 B1 | 3/2008 | Haarstad et al. |
| 7,338,520 B2 | 3/2008 | Bailey et al. |
| 7,343,195 B2 | 3/2008 | Strommer et al. |
| 7,374,571 B2 | 5/2008 | Pease et al. |
| 7,381,218 B2 | 6/2008 | Shreck |
| 7,384,411 B1 | 6/2008 | Condado |
| 7,393,338 B2 | 7/2008 | Nita |
| 7,406,970 B2 | 8/2008 | Zikorus et al. |
| 7,410,486 B2 | 8/2008 | Fuimaono et al. |
| 7,413,556 B2 | 8/2008 | Zhang et al. |
| 7,426,409 B2 | 9/2008 | Casscells et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,241 B2 | 12/2008 | Weng et al. |
| 7,470,284 B2 | 12/2008 | Lambrecht et al. |
| 7,481,838 B2 | 1/2009 | Carpentier et al. |
| 7,499,745 B2 | 3/2009 | Littrup et al. |
| 7,510,536 B2 | 3/2009 | Foley et al. |
| 7,540,846 B2 | 6/2009 | Harhen et al. |
| 7,540,852 B2 | 6/2009 | Nita et al. |
| 7,540,870 B2 | 6/2009 | Babaev et al. |
| 7,562,066 B2 | 7/2009 | Kawatani |
| 7,573,182 B2 | 8/2009 | Savage et al. |
| 7,591,996 B2 | 9/2009 | Hwang et al. |
| 7,604,608 B2 | 10/2009 | Nita et al. |
| 7,615,015 B2 | 11/2009 | Coleman |
| 7,617,005 B2 | 11/2009 | Demarais et al. |
| 7,621,902 B2 | 11/2009 | Nita et al. |
| 7,621,929 B2 | 11/2009 | Nita et al. |
| 7,640,046 B2 | 12/2009 | Pastore et al. |
| 7,641,633 B2 | 1/2010 | Laufer et al. |
| 7,655,005 B2 | 2/2010 | Bhola |
| 7,662,114 B2 | 2/2010 | Seip et al. |
| 7,670,335 B2 | 3/2010 | Keidar et al. |
| 7,674,259 B2 | 3/2010 | Shadduck et al. |
| 7,678,106 B2 | 3/2010 | Lee et al. |
| 7,706,882 B2 | 4/2010 | Francischelli et al. |
| 7,717,853 B2 | 5/2010 | Nita |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,653,438 B2 | 6/2010 | Deem et al. |
| 7,727,178 B2 | 6/2010 | Wilson et al. |
| 7,736,317 B2 | 6/2010 | Stephens et al. |
| 7,753,907 B2 | 7/2010 | Dimatteo et al. |
| 7,758,510 B2 | 7/2010 | Nita et al. |
| 7,771,372 B2 | 8/2010 | Wilson |
| 7,789,876 B2 | 9/2010 | Zikorus et al. |
| 7,792,568 B2 | 9/2010 | Zhong et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,837,676 B2 | 11/2010 | Sinelnikov et al. |
| 7,918,850 B2 | 4/2011 | Govari et al. |
| 7,942,871 B2 | 5/2011 | Thapliyal et al. |
| 7,950,397 B2 | 5/2011 | Thapliyal et al. |
| 7,955,293 B2 | 6/2011 | Nita et al. |
| 7,956,613 B2 | 6/2011 | Wald et al. |
| 7,967,782 B2 | 6/2011 | Laufer et al. |
| 7,972,330 B2 | 7/2011 | Alejandro et al. |
| 8,021,362 B2 | 9/2011 | Deem et al. |
| 8,025,661 B2 | 9/2011 | Arnold et al. |
| 8,052,636 B2 | 11/2011 | Moll et al. |
| 8,062,289 B2 | 11/2011 | Babaev |
| 8,080,006 B2 | 12/2011 | Lafontaine et al. |
| 8,137,274 B2 | 3/2012 | Weng et al. |
| 8,146,603 B2 | 4/2012 | Thapliyal et al. |
| 8,167,805 B2 | 5/2012 | Emery et al. |
| 8,190,238 B2 | 5/2012 | Moll et al. |
| 8,241,217 B2 | 8/2012 | Chiang et al. |
| 8,277,379 B2 | 10/2012 | Lau et al. |
| 8,295,912 B2 | 10/2012 | Gertner |
| 8,317,810 B2 | 11/2012 | Stangenes et al. |
| 8,088,127 B2 | 12/2012 | Mayse et al. |
| 8,382,697 B2 | 2/2013 | Brenneman et al. |
| 8,401,667 B2 | 3/2013 | Gustus et al. |
| 8,469,904 B2 | 6/2013 | Gertner |
| 8,512,262 B2 | 8/2013 | Gertner |
| 8,545,409 B2 | 10/2013 | Sliwa et al. |
| 8,556,834 B2 | 10/2013 | Gertner |
| 8,585,597 B2 | 11/2013 | Dae et al. |
| 8,758,334 B2 | 3/2014 | Coe et al. |
| 8,715,209 B2 | 5/2014 | Gertner |
| 8,974,446 B2 | 3/2015 | Nguyen et al. |
| 8,986,211 B2 | 3/2015 | Gertner et al. |
| 8,986,231 B2 | 3/2015 | Gertner et al. |
| 8,992,447 B2 | 3/2015 | Gertner et al. |
| 9,005,143 B2 | 4/2015 | Gertner |
| 9,028,417 B2 | 5/2015 | Sverdlik et al. |
| 9,119,951 B2 | 9/2015 | Gertner et al. |
| 9,119,952 B2 | 9/2015 | Gertner |
| 9,125,642 B2 | 9/2015 | Gertner |
| 9,174,065 B2 | 11/2015 | Gertner |
| 9,192,790 B2 | 11/2015 | Hastings et al. |
| 9,199,097 B2 | 12/2015 | Gertner |
| 9,352,171 B2 | 5/2016 | Gertner |
| 9,358,401 B2 | 6/2016 | Gertner |
| 9,566,456 B2 | 2/2017 | Sverdlik et al. |
| 2001/0031922 A1* | 10/2001 | Weng ............... A61B 17/0057 600/439 |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2001/0051774 A1 | 12/2001 | Littrup et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0035396 A1 | 3/2002 | Heath |
| 2002/0042650 A1 | 4/2002 | Vardi et al. |
| 2002/0045888 A1 | 4/2002 | Ramans |
| 2002/0052651 A1 | 5/2002 | Myers et al. |
| 2002/0058995 A1 | 5/2002 | Stevens |
| 2002/0071518 A1 | 6/2002 | Bruder et al. |
| 2002/0072789 A1 | 6/2002 | Hackett et al. |
| 2002/0077696 A1 | 6/2002 | Zadno/Azizi et al. |
| 2002/0095139 A1 | 7/2002 | Keogh et al. |
| 2002/0095209 A1 | 7/2002 | Zadno/Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0082612 A1 | 9/2002 | Nowlin |
| 2002/0123802 A1 | 9/2002 | Snyders |
| 2002/0133183 A1 | 9/2002 | Lentz et al. |
| 2002/0138109 A1 | 9/2002 | Keogh et al. |
| 2002/0143324 A1 | 10/2002 | Edwards et al. |
| 2002/0151970 A1 | 10/2002 | Garrison et al. |
| 2002/0161277 A1 | 10/2002 | Mansvelt/Beck et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0004439 A1 | 1/2003 | Pante et al. |
| 2003/0013949 A1 | 1/2003 | Moll |
| 2003/0014104 A1 | 1/2003 | Cribier |
| 2003/0023303 A1 | 1/2003 | Palmaz et al. |
| 2003/0028114 A1 | 2/2003 | Casscells et al. |
| 2003/0028247 A1 | 2/2003 | Cali |
| 2003/0040771 A1 | 2/2003 | Hyodoh et al. |
| 2003/0040772 A1 | 2/2003 | Hvodoh et al. |
| 2003/0045872 A1 | 3/2003 | Jacobs |
| 2003/0050632 A1 | 3/2003 | Fjield et al. |

(56) References Cited

U.S. PATENT DOCUMENTS

| | | |
|---|---|---|
| 2003/0050694 A1 | 3/2003 | Yanq et al. |
| 2003/0055410 A1 | 3/2003 | Evans |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0069619 A1 | 4/2003 | Fenn et al. |
| 2003/0078470 A1 | 4/2003 | Borst |
| 2003/0078471 A1 | 4/2003 | Foley et al. |
| 2003/0088189 A1 | 5/2003 | Tu et al. |
| 2003/0109924 A1 | 6/2003 | Cribier |
| 2003/0120270 A1 | 6/2003 | Acker |
| 2003/0125795 A1 | 7/2003 | Pavcnik et al. |
| 2003/0130726 A1 | 7/2003 | Thorpe et al. |
| 2003/0139804 A1 | 7/2003 | Hankh et al. |
| 2003/0144656 A1 | 7/2003 | Ocel |
| 2003/0149475 A1 | 8/2003 | Hyodoh et al. |
| 2003/0149476 A1 | 8/2003 | Damm et al. |
| 2003/0149478 A1 | 8/2003 | Fiqulla et al. |
| 2003/0153974 A1 | 8/2003 | Spenser et al. |
| 2003/0158463 A1 | 8/2003 | Julian et al. |
| 2003/0181850 A1 | 9/2003 | Diamond et al. |
| 2003/0191462 A1 | 10/2003 | Jacobs |
| 2003/0191519 A1 | 10/2003 | Lombardi et al. |
| 2003/0199747 A1 | 10/2003 | Michlitsch et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0216715 A1 | 11/2003 | Moll |
| 2003/0216724 A1 | 11/2003 | Jahns |
| 2004/0015106 A1 | 1/2004 | Coleman |
| 2004/0015219 A1 | 1/2004 | Francischelli |
| 2004/0024371 A1 | 2/2004 | Plicchi et al. |
| 2004/0034411 A1 | 2/2004 | Quijano et al. |
| 2004/0039436 A1 | 2/2004 | Spenser et al. |
| 2004/0044340 A1 | 3/2004 | Francischelli |
| 2004/0049179 A1 | 3/2004 | Francischelli |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0054362 A1 | 3/2004 | Lopath et al. |
| 2004/0068257 A1 | 4/2004 | Lopath et al. |
| 2004/0073206 A1 | 4/2004 | Foley et al. |
| 2004/0078069 A1 | 4/2004 | Francischelli |
| 2004/0082904 A1 | 4/2004 | Houde et al. |
| 2004/0087940 A1 | 5/2004 | Jahns |
| 2004/0088045 A1 | 5/2004 | Cox |
| 2004/0092926 A1 | 5/2004 | Hoey |
| 2004/0093005 A1 | 5/2004 | Durcan |
| 2004/0093060 A1 | 5/2004 | Sequin et al. |
| 2004/0097788 A1 | 5/2004 | Mourles et al. |
| 2004/0098112 A1 | 5/2004 | DiMatteo et al. |
| 2004/0106880 A1 | 6/2004 | Weng et al. |
| 2004/0106990 A1 | 6/2004 | Spence et al. |
| 2004/0111016 A1 | 6/2004 | Casscells et al. |
| 2004/0111096 A1 | 6/2004 | Tu et al. |
| 2004/0116951 A1 | 6/2004 | Rosenqart |
| 2004/0117004 A1 | 6/2004 | Osborne et al. |
| 2004/0122468 A1 | 6/2004 | Yodfat et al. |
| 2004/0122516 A1 | 6/2004 | Fogarty et al. |
| 2004/0127979 A1 | 7/2004 | Wilson et al. |
| 2004/0138109 A1 | 7/2004 | Chen et al. |
| 2004/0138742 A1 | 7/2004 | Myers et al. |
| 2004/0138743 A1 | 7/2004 | Myers et al. |
| 2004/0143260 A1 | 7/2004 | Francischelli |
| 2004/0158143 A1 | 8/2004 | Flaherty |
| 2004/0162507 A1* | 8/2004 | Govari ............... A61N 7/02 601/2 |
| 2004/0162555 A1 | 8/2004 | Farley et al. |
| 2004/0167549 A1 | 8/2004 | Borst |
| 2004/0176757 A1 | 9/2004 | Sinelnikov et al. |
| 2004/0186465 A1 | 9/2004 | Francischelli |
| 2004/0193211 A1 | 9/2004 | Voegele et al. |
| 2004/0215183 A1 | 10/2004 | Hoey |
| 2004/0220556 A1 | 11/2004 | Cooper et al. |
| 2004/0220560 A1 | 11/2004 | Briscoe |
| 2004/0236322 A1 | 11/2004 | Mulier |
| 2004/0267326 A1 | 12/2004 | Ocel |
| 2005/0033270 A1 | 2/2005 | Ramans |
| 2005/0033280 A1 | 2/2005 | Francischelli |
| 2005/0090815 A1 | 4/2005 | Francischelli |
| 2005/0107808 A1 | 5/2005 | Evans |
| 2005/0143729 A1 | 6/2005 | Francischelli |
| 2005/0165298 A1* | 7/2005 | Larson ............... A61N 7/02 600/410 |
| 2005/0165388 A1 | 7/2005 | Bhola |
| 2005/0165391 A1 | 7/2005 | Maguire et al. |
| 2005/0165392 A1 | 7/2005 | Francischelli |
| 2005/0203410 A1 | 9/2005 | Jenkins |
| 2005/0209564 A1 | 9/2005 | Bonner |
| 2005/0214268 A1 | 9/2005 | Cavanagh et al. |
| 2005/0228286 A1 | 10/2005 | Messerly et al. |
| 2005/0240170 A1 | 10/2005 | Zhang et al. |
| 2005/0267454 A1 | 12/2005 | Hissong |
| 2005/0283195 A1 | 12/2005 | Pastore et al. |
| 2006/0009753 A1 | 1/2006 | Fjield et al. |
| 2006/0009756 A1 | 1/2006 | Francischelli |
| 2006/0009759 A1 | 1/2006 | Christian |
| 2006/0036128 A1 | 2/2006 | Borst |
| 2006/0058711 A1 | 3/2006 | Harhen et al. |
| 2006/0100514 A1 | 5/2006 | Lopath |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149166 A1 | 7/2006 | Zvuloni |
| 2006/0155269 A1 | 7/2006 | Warnking |
| 2006/0167474 A1 | 7/2006 | Bloom et al. |
| 2006/0171895 A1 | 8/2006 | Bucay-Couto |
| 2006/0178559 A1 | 8/2006 | Kumar |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0229594 A1 | 10/2006 | Francischelli et al. |
| 2006/0241414 A1 | 10/2006 | Nowlin |
| 2006/0241523 A1 | 10/2006 | Sinelnikov et al. |
| 2006/0247763 A1 | 11/2006 | Slater |
| 2006/0259137 A1 | 11/2006 | Artof et al. |
| 2006/0265056 A1 | 11/2006 | Nguyen et al. |
| 2006/0270975 A1 | 11/2006 | Savage |
| 2006/0270976 A1 | 11/2006 | Savage |
| 2006/0271166 A1 | 11/2006 | Thill et al. |
| 2006/0271175 A1 | 11/2006 | Woolfson et al. |
| 2006/0273695 A1 | 12/2006 | Savage |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027390 A1 | 2/2007 | Maschke et al. |
| 2007/0027518 A1 | 2/2007 | Case et al. |
| 2007/0027533 A1 | 2/2007 | Douk |
| 2007/0038056 A1 | 2/2007 | Pappone et al. |
| 2007/0043435 A1 | 2/2007 | Sequin et al. |
| 2007/0051377 A1 | 3/2007 | Douk et al. |
| 2007/0066897 A1 | 3/2007 | Sekins et al. |
| 2007/0073392 A1 | 3/2007 | Heyninck/Jantz et al. |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Canqialosi et al. |
| 2007/0100449 A1 | 5/2007 | O'Neil et al. |
| 2007/0112415 A1 | 5/2007 | Bartlett |
| 2007/0135875 A1 | 6/2007 | Demarais et al. |
| 2007/0162102 A1 | 7/2007 | Ryan et al. |
| 2007/0162113 A1 | 7/2007 | Sharkawy et al. |
| 2007/0179379 A1 | 8/2007 | Weng et al. |
| 2007/0185513 A1 | 8/2007 | Woolfson et al. |
| 2007/0203391 A1 | 8/2007 | Bloom et al. |
| 2007/0203480 A1 | 8/2007 | Mody et al. |
| 2007/0208256 A1 | 9/2007 | Marilla |
| 2007/0208301 A1 | 9/2007 | Evard et al. |

(56) References Cited

U.S. PATENT DOCUMENTS

| | | |
|---|---|---|
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239062 A1 | 10/2007 | Chopra et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0039746 A1 | 2/2008 | Hissong et al. |
| 2008/0048656 A1 | 2/2008 | Tan et al. |
| 2008/0064957 A1 | 3/2008 | Spence |
| 2008/0065001 A1 | 3/2008 | DiNucci et al. |
| 2008/0065206 A1 | 3/2008 | Liddicoat |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0097251 A1 | 4/2008 | Babaev |
| 2008/0119879 A1 | 5/2008 | Brenneman et al. |
| 2008/0133003 A1 | 6/2008 | Sequin et al. |
| 2008/0140189 A1 | 6/2008 | Nquyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Riqhini et al. |
| 2008/0154356 A1 | 6/2008 | Obermiller et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0208169 A1 | 8/2008 | Boyle et al. |
| 2008/0215143 A1 | 9/2008 | Sequin |
| 2008/0215144 A1 | 9/2008 | Ryan et al. |
| 2008/0221448 A1 | 9/2008 | Khuri-Yakub et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249419 A1 | 10/2008 | Sekins et al. |
| 2008/0255478 A1 | 10/2008 | Burdette et al. |
| 2008/0255651 A1 | 10/2008 | Dwork |
| 2008/0262593 A1 | 10/2008 | Ryan et al. |
| 2008/0294037 A1 | 11/2008 | Richter |
| 2008/0312673 A1 | 12/2008 | Viswanathan et al. |
| 2009/0005863 A1 | 1/2009 | Goetz et al. |
| 2009/0012600 A1 | 1/2009 | Styrc et al. |
| 2009/0030312 A1 | 1/2009 | Hadjicostis |
| 2009/0036774 A1 | 2/2009 | Weng et al. |
| 2009/0043186 A1 | 2/2009 | Jung et al. |
| 2009/0048656 A1 | 2/2009 | Wen |
| 2009/0054976 A1 | 2/2009 | Tuval et al. |
| 2009/0062697 A1 | 3/2009 | Zhang et al. |
| 2009/0069886 A1 | 3/2009 | Suri et al. |
| 2009/0069887 A1 | 3/2009 | Riqhini et al. |
| 2009/0069889 A1 | 3/2009 | Suri et al. |
| 2009/0118620 A1 | 5/2009 | Tgavalekos et al. |
| 2009/0131798 A1 | 5/2009 | Minar et al. |
| 2009/0138079 A1 | 5/2009 | Tuval et al. |
| 2009/0164004 A1 | 6/2009 | Cohn |
| 2009/0171447 A1 | 7/2009 | VonSeqqesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinqer et al. |
| 2009/0216312 A1 | 8/2009 | Straubinqer et al. |
| 2009/0216313 A1 | 8/2009 | Straubinqer et al. |
| 2009/0221955 A1 | 9/2009 | Babaev |
| 2009/0228003 A1 | 9/2009 | Sinelnikov |
| 2009/0240264 A1 | 9/2009 | Tuval et al. |
| 2009/0240320 A1 | 9/2009 | Tuval et al. |
| 2009/0247912 A1 | 10/2009 | Warnking |
| 2009/0264755 A1 | 10/2009 | Chen et al. |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0016958 A1 | 1/2010 | St. Goar et al. |
| 2010/0049099 A1 | 2/2010 | Thapliyal et al. |
| 2010/0049186 A1 | 2/2010 | Ingle et al. |
| 2010/0106005 A1 | 4/2010 | Karczmar et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0125268 A1 | 5/2010 | Gustus et al. |
| 2010/0130892 A1 | 5/2010 | Warnking |
| 2010/0152582 A1 | 6/2010 | Thapliyal et al. |
| 2010/0168624 A1 | 7/2010 | Sliwa |
| 2010/0179424 A1 | 7/2010 | Warnking |
| 2010/0191112 A1 | 7/2010 | Demarais et al. |
| 2010/0191232 A1 | 7/2010 | Boveda |
| 2010/0198065 A1 | 8/2010 | Thapliyal et al. |
| 2010/0204577 A1 | 8/2010 | Sekins et al. |
| 2010/0217162 A1 | 8/2010 | Hissong et al. |
| 2010/0228122 A1 | 9/2010 | Keenan et al. |
| 2010/0249604 A1 | 9/2010 | Hastings et al. |
| 2010/0256616 A1 | 10/2010 | Katoh et al. |
| 2010/0268217 A1 | 10/2010 | Habib |
| 2011/0021913 A1 | 1/2011 | Weng et al. |
| 2011/0066085 A1 | 3/2011 | Weng et al. |
| 2011/0071400 A1 | 3/2011 | Hastings et al. |
| 2011/0071401 A1 | 3/2011 | Hastings et al. |
| 2011/0092781 A1 | 4/2011 | Gertner |
| 2011/0092880 A1 | 4/2011 | Gertner |
| 2011/0118598 A1 | 5/2011 | Gertner |
| 2011/0118600 A1 | 5/2011 | Gertner |
| 2011/0118632 A1 | 5/2011 | Sinelnikov et al. |
| 2011/0137149 A1 | 6/2011 | Gertner |
| 2011/0137298 A1 | 6/2011 | Nguyen et al. |
| 2011/0146673 A1 | 6/2011 | Keast et al. |
| 2011/0172527 A1 | 7/2011 | Gertner |
| 2011/0172528 A1 | 7/2011 | Gertner |
| 2011/0172529 A1 | 7/2011 | Gertner |
| 2011/0172654 A1 | 7/2011 | Barry et al. |
| 2011/0178403 A1 | 7/2011 | Weng et al. |
| 2011/0257523 A1 | 10/2011 | Hastings et al. |
| 2011/0257561 A1 | 10/2011 | Gertner et al. |
| 2011/0257562 A1 | 10/2011 | Schaer |
| 2011/0257563 A1 | 10/2011 | Thapliyal et al. |
| 2011/0319765 A1 | 12/2011 | Gertner et al. |
| 2012/0010902 A1 | 1/2012 | Emery et al. |
| 2012/0016226 A1 | 1/2012 | Gertner |
| 2012/0022409 A1 | 1/2012 | Gertner et al. |
| 2012/0059286 A1 | 3/2012 | Hastings et al. |
| 2012/0065492 A1 | 3/2012 | Gertner et al. |
| 2012/0065493 A1 | 3/2012 | Gertner |
| 2012/0065494 A1 | 3/2012 | Gertner et al. |
| 2012/0065506 A1 | 3/2012 | Smith |
| 2012/0095335 A1 | 4/2012 | Sverdlik et al. |
| 2012/0095371 A1 | 4/2012 | Sverdlik et al. |
| 2012/0109018 A1 | 5/2012 | Gertner et al. |
| 2012/0109021 A1 | 5/2012 | Hastings et al. |
| 2012/0109023 A1 | 5/2012 | Emery et al. |
| 2012/0123243 A1 | 5/2012 | Hastings |
| 2012/0123261 A1 | 5/2012 | Jenson et al. |

(56) References Cited

U.S. PATENT DOCUMENTS

| | | |
|---|---|---|
| 2012/0123303 A1 | 5/2012 | Sogard et al. |
| 2012/0143078 A1 | 6/2012 | Kassab et al. |
| 2012/0143097 A1 | 6/2012 | Pike, Jr. |
| 2012/0157984 A1 | 6/2012 | Thapliyal et al. |
| 2012/0172723 A1 | 7/2012 | Gertner |
| 2012/0197166 A1 | 8/2012 | Gertner |
| 2012/0209118 A1 | 8/2012 | Warnking |
| 2012/0232409 A1 | 9/2012 | Stahmann et al. |
| 2012/0232436 A1 | 9/2012 | Warnking |
| 2012/0238918 A1 | 9/2012 | Gertner |
| 2012/0238919 A1 | 9/2012 | Gertner |
| 2012/0245494 A1 | 9/2012 | Gertner |
| 2012/0253239 A1 | 10/2012 | Gertner et al. |
| 2012/0265227 A1 | 10/2012 | Sverdlik et al. |
| 2012/0271171 A1 | 10/2012 | Gertner |
| 2013/0023862 A1 | 1/2013 | Marrouche |
| 2013/0090578 A1 | 4/2013 | Smith et al. |
| 2013/0090649 A1 | 4/2013 | Smith et al. |
| 2013/0110012 A1 | 5/2013 | Perozek et al. |
| 2013/0123625 A1 | 5/2013 | Hastings et al. |
| 2013/0123670 A1 | 5/2013 | Smith |
| 2013/0131668 A1 | 5/2013 | Schaer |
| 2013/0138018 A1 | 5/2013 | Gertner |
| 2013/0138095 A1 | 5/2013 | Gertner |
| 2013/0184703 A1 | 7/2013 | Shireman et al. |
| 2013/0190716 A1 | 7/2013 | Gertner |
| 2013/0190748 A1 | 7/2013 | Coe et al. |
| 2013/0197555 A1 | 8/2013 | Schaer |
| 2013/0204167 A1 | 8/2013 | Sverdlik et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0225973 A1 | 8/2013 | Gertner |
| 2013/0253381 A1 | 9/2013 | Gertner |
| 2013/0281889 A1 | 10/2013 | Gertner |
| 2013/0296646 A1 | 11/2013 | Barbut et al. |
| 2013/0331739 A1 | 12/2013 | Gertner |
| 2014/0012133 A1 | 1/2014 | Sverdlik et al. |
| 2014/0018888 A1 | 1/2014 | Ostroot et al. |
| 2014/0031727 A1 | 1/2014 | Warnking |
| 2014/0039477 A1 | 2/2014 | Sverdlik et al. |
| 2014/0039479 A1 | 2/2014 | Gertner |
| 2014/0046229 A1 | 2/2014 | Hawkins et al. |
| 2014/0046313 A1 | 2/2014 | Pederson et al. |
| 2014/0058188 A1 | 2/2014 | Gertner |
| 2014/0058293 A1 | 2/2014 | Hynynen et al. |
| 2014/0058294 A1 | 2/2014 | Gross et al. |
| 2014/0066883 A1 | 3/2014 | Azamian et al. |
| 2014/0066916 A1 | 3/2014 | Coe et al. |
| 2014/0066919 A1 | 3/2014 | Azamian et al. |
| 2014/0066920 A1 | 3/2014 | Azamian et al. |
| 2014/0066921 A1 | 3/2014 | Coe et al. |
| 2014/0066922 A1 | 3/2014 | Coe et al. |
| 2014/0066923 A1 | 3/2014 | Azamian et al. |
| 2014/0066924 A1 | 3/2014 | Azamian et al. |
| 2014/0074089 A1 | 3/2014 | Nishii |
| 2014/0107482 A1 | 4/2014 | Warnking |
| 2014/0128734 A1 | 5/2014 | Genstler et al. |
| 2014/0128865 A1 | 5/2014 | Gross |
| 2014/0135661 A1 | 5/2014 | Garrison et al. |
| 2014/0135715 A1 | 5/2014 | Lambert et al. |
| 2014/0163372 A1 | 6/2014 | Deladi et al. |
| 2014/0163540 A1 | 6/2014 | Iyer et al. |
| 2014/0180085 A1 | 6/2014 | Dae et al. |
| 2014/0180197 A1 | 6/2014 | Sverdlik et al. |
| 2014/0194784 A1 | 7/2014 | Gertner |
| 2014/0194785 A1 | 7/2014 | Gertner |
| 2014/0194786 A1 | 7/2014 | Gertner et al. |
| 2014/0200489 A1 | 7/2014 | Behar et al. |
| 2014/0214018 A1 | 7/2014 | Behar et al. |
| 2014/0272110 A1 | 9/2014 | Taylor et al. |
| 2014/0276050 A1 | 9/2014 | Jenson et al. |
| 2014/0276714 A1 | 9/2014 | Edmunds et al. |
| 2014/0277033 A1 | 9/2014 | Taylor et al. |
| 2014/0316269 A1 | 10/2014 | Zhang et al. |
| 2014/0336497 A1 | 11/2014 | Gertner |
| 2015/0011987 A1 | 1/2015 | Kobayashi et al. |
| 2015/0025518 A1 | 1/2015 | Kobayashi et al. |
| 2015/0073400 A1 | 3/2015 | Sverdlik et al. |
| 2015/0105715 A1 | 4/2015 | Pikus et al. |
| 2015/0202466 A1 | 7/2015 | Gertner |
| 2015/0290427 A1 | 10/2015 | Warnking |
| 2016/0059044 A1 | 3/2016 | Gertner |
| 2016/0113699 A1 | 4/2016 | Sverdlik et al. |
| 2016/0317844 A1 | 11/2016 | Lupotti |

FOREIGN PATENT DOCUMENTS

| | | |
|---|---|---|
| EP | 0432560 A2 | 6/1991 |
| EP | 0293760 A3 | 7/1991 |
| EP | 0432560 A2 | 6/1994 |
| EP | 0630629 A1 | 12/1994 |
| EP | 668058 A1 | 8/1995 |
| EP | 808606 A1 | 11/1997 |
| EP | 0908139 A1 | 4/1999 |
| EP | 0919193 A1 | 6/1999 |
| EP | 0920835 A1 | 6/1999 |
| EP | 0993806 A2 | 4/2000 |
| EP | 0993806 A3 | 6/2000 |
| EP | 1095627 | 5/2001 |
| EP | 1181895 | 2/2002 |
| EP | 1299035 | 4/2003 |
| EP | 1299038 | 4/2003 |
| EP | 1579889 | 9/2005 |
| EP | 1596746 | 11/2005 |
| EP | 1620156 | 2/2006 |
| EP | 1750804 | 7/2008 |
| EP | 1265674 | 9/2008 |
| EP | 2018129 | 1/2009 |
| EP | 2218479 | 8/2010 |
| EP | 2275174 | 1/2011 |
| EP | 2275175 | 1/2011 |
| EP | 2285304 | 2/2011 |
| EP | 2285334 | 2/2011 |
| EP | 2296573 | 3/2011 |
| EP | 2307098 | 4/2011 |
| EP | 2309939 | 4/2011 |
| EP | 2320821 | 5/2011 |
| EP | 2344039 | 7/2011 |
| EP | 2352559 | 8/2011 |
| EP | 2430996 | 3/2012 |
| EP | 2430997 | 3/2012 |
| EP | 2430998 | 3/2012 |
| EP | 2455015 | 5/2012 |
| EP | 2488250 | 8/2012 |
| EP | 2493568 | 9/2012 |
| EP | 2493569 | 9/2012 |
| EP | 2521593 | 11/2012 |
| EP | 2540246 | 1/2013 |
| EP | 2540347 | 1/2013 |
| EP | 2540348 | 1/2013 |
| EP | 2558165 | 2/2013 |
| EP | 2613724 | 7/2013 |
| EP | 2640300 | 9/2013 |
| EP | 2670315 | 12/2013 |
| EP | 2675525 | 12/2013 |
| EP | 2780081 | 9/2014 |
| EP | 2890459 | 7/2015 |
| EP | 2629683 | 10/2015 |
| EP | 2964086 | 1/2016 |
| EP | 2995350 | 3/2016 |
| EP | 2999411 | 3/2016 |
| EP | 3005944 | 4/2016 |
| EP | 3017770 | 5/2016 |
| EP | 3074090 | 10/2016 |
| EP | 2629736 | 2/2017 |
| EP | 3132828 | 2/2017 |
| EP | 3142564 | 3/2017 |
| EP | 2670315 | 4/2017 |
| GB | 2140695 A | 12/1984 |
| GB | 2214428 A | 9/1989 |
| GB | 2233561 | 1/1991 |

(56) References Cited

FOREIGN PATENT DOCUMENTS

| | | |
|---|---|---|
| GB | 2214428 B | 6/1991 |
| GB | 2267827 | 12/1993 |
| WO | WO87/04081 | 7/1987 |
| WO | WO88/00481 | 1/1988 |
| WO | WO94/03142 | 2/1994 |
| WO | WO94/14383 | 7/1994 |
| WO | WO94/14715 | 7/1994 |
| WO | WO1995001751 | 1/1995 |
| WO | WO95/10753 | 4/1995 |
| WO | WO95/17127 | 6/1995 |
| WO | WO96/00033 | 1/1996 |
| WO | WO1997003604 | 2/1997 |
| WO | WO00/06041 | 11/1997 |
| WO | WO98/10705 | 3/1998 |
| WO | WO98/17182 | 4/1998 |
| WO | WO1998029030 | 7/1998 |
| WO | WO97/40751 | 11/1998 |
| WO | WO98/48703 | 11/1998 |
| WO | WO98/49947 | 11/1998 |
| WO | WO1998058588 | 12/1998 |
| WO | WO1999002096 | 1/1999 |
| WO | WO99/08585 | 2/1999 |
| WO | WO99/09892 | 3/1999 |
| WO | WO99/16367 | 4/1999 |
| WO | WO00/10466 | 3/2000 |
| WO | WO00/15119 | 3/2000 |
| WO | WO2001022897 | 4/2001 |
| WO | WO2001/080755 | 11/2001 |
| WO | WO2001095820 | 12/2001 |
| WO | WO03/001969 | 1/2003 |
| WO | WO03/001998 | 1/2003 |
| WO | WO2003026525 | 4/2003 |
| WO | WO2004098694 | 11/2004 |
| WO | WO2004110258 | 12/2004 |
| WO | WO2005/113068 | 12/2005 |
| WO | WO2006041881 | 4/2006 |
| WO | WO2007/067945 | 6/2007 |
| WO | WO2007134258 | 11/2007 |
| WO | WO2007/14031 | 12/2007 |
| WO | WO2008102363 | 8/2008 |
| WO | WO2008151001 | 12/2008 |
| WO | WO2009152379 | 6/2009 |
| WO | WO2009137819 | 11/2009 |
| WO | WO2009152354 | 12/2009 |
| WO | WO2009152467 | 12/2009 |
| WO | WO2010009472 | 1/2010 |
| WO | WO2010009473 | 1/2010 |
| WO | WO2010080886 | 7/2010 |
| WO | WO2011046879 | 4/2011 |
| WO | WO2011046880 | 4/2011 |
| WO | WO2011053757 | 5/2011 |
| WO | WO2011053772 | 5/2011 |
| WO | WO2011055143 | 5/2011 |
| WO | WO2011056514 | 5/2011 |
| WO | WO2011059792 | 5/2011 |
| WO | WO2011130531 | 10/2011 |
| WO | WO2012033860 | 3/2012 |
| WO | WO2012052921 | 4/2012 |
| WO | WO2012052922 | 4/2012 |
| WO | WO2012052924 | 4/2012 |
| WO | WO2012052926 | 4/2012 |
| WO | WO2012052927 | 4/2012 |
| WO | WO2012068354 | 5/2012 |
| WO | WO2012106492 | 8/2012 |
| WO | WO2012112165 | 8/2012 |
| WO | WO2012120495 | 9/2012 |
| WO | WO2012125172 | 9/2012 |
| WO | WO2013013156 | 1/2013 |
| WO | WO2013014583 | 1/2013 |
| WO | WO2013030807 | 3/2013 |
| WO | WO2013055685 | 4/2013 |
| WO | WO2013074218 | 5/2013 |
| WO | WO2013074661 | 5/2013 |
| WO | WO2013111136 | 8/2013 |
| WO | WO2013116380 | 8/2013 |
| WO | WO2013150776 | 10/2013 |
| WO | WO2013157011 | 10/2013 |
| WO | WO2013157207 | 10/2013 |
| WO | WO2013157208 | 10/2013 |
| WO | WO2013165935 | 11/2013 |
| WO | WO2014068577 | 5/2014 |
| WO | WO2014078301 | 5/2014 |
| WO | WO2014159276 | 10/2014 |
| WO | WO2014164363 | 10/2014 |
| WO | WO2014188430 | 11/2014 |

OTHER PUBLICATIONS

Samuels, et al., "The Electrophyiologist and the Cardia Surgeon," advances in Cardiac Surgery, Chapter 6, vol. 12, 2000, pp. 97/115.

Schmitt, et al., "Recent Advances in Cardia Mapping Techniques," Catheter/Ablative Techniques and the Implantable Cardioverter Defibrillator, 1999, pp. 149/156.

Ki/Bong Kim, M.D., et al., Abstract "The Cox/Maze III Procedure for Atrial Fibrillation Associated with Rheumatic Mitral Valve Disease," The Annals of Thoracic Surgery, 2000; pp. 1/5.

Taijiro Sueda, et al., "Efficacy of a Simple Left Atrial Procedure for Chronic Atrial Fibrillation in Mitral Valve Operations," The Annals of Thoracic Surgery, 1997, vol. 63, pp. 1070/1073.

Mien/Cheng Chen, M.D., et al., "Radiofrequency and Cryoabiation of Atrial Fibrillation in Patients Undergoing Valvular Operations," Annals of Thoracic Surgery, 1998:65:1666/1672.

Arif Elvan, M.D., et al., Abstract, "Radiofrequency Catheter Ablation of the Atria Reduces Inducibility and Duration of Atrial Fibrillation in Dogs," Circulation, 1995:91:2235/2244.

Stuart P. Thomas, et al., "Mechanism, Localization and Cure of Atrial Arrhythmias Occurring After a New Intraoperative Endocardial Radiofrequency Ablation Procedure for Atrial Fibrillation," Journal of the American College of Cardiology, 2000, vol. 35 No. 2, pp. 442/450.

Akira T. Kawaguchi, et al., "Factors Affecting Rhythm After the Maze Procedure for Atrial Fibrillation", 1998; vol. 78, No. 5, pp. 1288/1296.

Ivan M. Robbins, M.D., et al., "Pulmonary Vein Stenosis After Catheter Ablation of ATrial Fibrillation," Circulation, 1998; 98:1769/1775.

Enrique, J. Berjano, et al., "Bipolar Electrosurgery with Long Electrodes for RF Coagulation of Atrial Tissue," Proceedings 19th International Conference—IEEE/EMBS Oct. 30-Nov. 2, 1997 Chicago, Ill. USA, pp. 2528/2530.

Taijiro Sueda, et al., "Simple Left Atria] Procedure for Chronic Atrial Fibrillation Associated with Mitral Valve Disease," The Annals of Thoracic Surgery, 1996;62:17961/1800.

Yoshio Kosakai, M.D. et al., "Cox Maze Procedure for Chronic Atrial Fibrillation Associated with Mitral Valve Disease," The Journal of Thoracic and Cardiovascular Surgery, 1994; vol. 108, No. 6, pp. 1049/1055.

Yoshito Inoue, et al., "Video Assisted Thoracoscopic and Cardioscopic Radiofrequency Maze Ablation," ASAIO Journal, 1997, pp. 334/337.

Response in U.S. Patent Publication No. 2003/0144656, U.S. Appl. No. 10/056,807, filed Apr. 25, 2006.

Chitwood, "Will C. Sealy, MD: The Father of Arrhythmia Surgery / The Story of the Fisherman with a Fast Pulse," Annals of Thoracic Surgery 58:1228/1239, 1994.

Gallagher et al., "Cryosurgical Ablation of Accessory Atrioventrical Connections: A Method for Correction of the Pre/excitation Syndrome," Circulation 55(3): 471/479, 1977.

Sealy, "Direct Surgical Treatment of Arrhythmias: The Last Frontier in Surgical Cardiology," Chest 75(5): 536/537, 1979.

Sealy, "The Evolution of the Surgical Methods for Interruption of Right Free Wall Kent Bundles," The Annals of Thoracic Surgery 36(1): 29/36, 1983.

Guiraudon et al., "Surgical Repair of Wolff/Parkinson/White Syndrome: A New Closed/Heart Techique," The Annals of Thoracic Surgery 37(1): 67/71, 1984.

(56) References Cited

OTHER PUBLICATIONS

Klein et al., "Surgical Correction of the Wolff/Parkinson/White Syndrome in the Closed Heart Using Cryosurgery: A Simplified Approach," JACC 3(2): 405/409, 1984.
Randall et al., "Local Epicardial Chemical Ablation of Vagal Input to Sino/Atrial and Atrioventricular Regions of the Canine Heart," Journal of the Autonomic Nervous System 11:145/159, 1984.
Guiraudon et at., "Surgical Ablation of Posterior Septal Accessory Pathways in the Wolf/Parkinson/White Syndrome by a Closed Heart Technique," Journal Thoracic Cardiovascular Surgery 92:406/413, 1986.
Gallagher et al., "Surgical Treatment of Arrhythmias," The American Journal of Cardiology 61:27A/44A, 1988.
Mahomed et al., "Surgical Division of Wolff/Parkinson/White Pathways Utilizing the Closed/Heart Technique: A 2/Year Experience in 47 Patients," The Annals of Thoracic Surgery 45(5): 495/504, 1988.
Cox et al., Surgery for Atrial Fibrillation; Seminars in Thoracic and Cardiovascular Surgery, vol. 1, No. 1 (Jul. 1989) pp. 67/73.
Bredikis and Bredikis; Surgery of Tachyarrhythmia: Intracardiac Closed Heart Cryoablation; PACE, vol. 13, pp. 1980/1984.
McCarthy et al., "Combined Treatment of Mitral Regurgitation and Atrial Fibrillation with Valvuloplasty and the Maze Procedure," The American Journal of Cardiology 71: 483/486, 1993.
Yamauchi et al. "Use of Intraoperative Mapping to Optimize Surgical Ablation of Atrial Flutter," The Annals of Thoracic Surgery 56: 337/342, 1993.
Graffigna et al., "Surgical Treatment of Wolff/Parkinson/White Syndrome: Epicardial Approach Without the Use of Cardiopulmonary Bypass," Journal of Cardiac Surgi 8: 108/116, 1993.
Siefert et al., "Radiofrequency Maze Ablation for Atrial Fibrillation," Circulation 90(4): 1/594.
Surgical treatment of atrial fibrillation: a review; Europace (2004) 5, S20/S29.
Cox et al., "Modification of the Maze Procedure for Atrial Flutter and Atrial Fibrillation. I. Rational and Surgical Results," The Journal of Thoracic Cardiovascular Surgery 110: 473/484, 1995.
Cox, "The Maze III Procedure for Treatment of Atrial Fibrillation," Sabiston DC, ed Atlas of Cardiothoracic Surgery, Philadelphia: WB Saunders: 460/475, 1994.
Tsui et al., "Maze 3 for Atrial Fibrillation: Two Cuts Too Few?" PACE 17: 2163/2166, 1994.
Cox et al., "The Surgical Treatment of Atrial Fibrillation, IV Surgical Technique," *J. of Thorac Cardiovasc Surg.* 1991: 101: 584/593.
Nardella, "Radio Frequency Energy and Impedance Feedback," SPIE vol. 1068, Catheter Based Sensing and Imaging Technology (1989).
Avitall et. al., "A Thoracoscopic Approach to Ablate Atrial Fibrillation via Linear Radiofrequency Lesion Generation on the Epicardium of Both Atria," PACE, Apr. 1996;19(Part 11):626,#241.
Sie et al., "Radiofrequency Ablation of Atrial Fibrillation in Patients Undergoing Mitral Valve Surgery. First Experience," Circulation (Nov. 1996) 96:450,1/675,#3946.
Sie et al., "Radiofrequency Ablation of Atrial Fibrillation in Patients Undergoing Valve Surgery," Circulation (Nov. 1997) 84:1450,#2519.
Jais et al., "Catheter Ablation for Paroxysmal Atrial Fibrillation: High Success Rates with Ablation in the Left Atrium," Circulation (Nov. 1996) 94:1/675,#3946.
Cox, "Evolving Applications of the Maze Procedure for Atrial Fibrillation," Ann Thorac Surg, 1993;55:578/580.
Cox et al. "Five/Year Experience with the Maze Procedure for Atrial Fibrillation," Ann Thorac Surg, 1993; 56:814/824.
Avitall et al., "New Monitoring Criteria for Transmural Ablation of Atrial Tissues," Circulation, 1996;94(Supp 1):11493, #2889.
Cox et al., "An 8 1/2 Year Clinical Experience with Surgery for Atrial Fibrillation," Annals of Surgery, 1996;224(3):267/275.
Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257/279.

Haissaguerre et al., "Right and Left Atrial Radiofrequency Catheter Therapy of Paroxysmal Atrial Fibrillation," Journal of Cardiovascular Electrophysiology, 1996;7(12):1132/1144.
Haissaguerre et al., "Role of Catheter Ablation for Atrial Fibrillation," Current Opinion in Cardiology, 1997;12:18/23.
Kawaguchi et al., "Risks and Benefits of Combined Maze Procedure for Atrial Fibrillation Associated with Organic Heart Disease," JACC, 1996;28(4):985/990.
Cox, et al., "Perinodal cryosurgery for atrioventricular node reentry tachycardia in 23 patients," Journal of Thoracic and Cardiovascular Surgery, 99:3, Mar. 1990, pp. 440/450.
Cox, "Anatomic/Electrophysiologic Basis for the Surgical Treatment of Refractory Ischemic Ventricular Tachycardia," Annals of Surgery, Aug. 1983; 198:2;119/129.
Williams, et al., "Left atrial isolation," J. Thorac Cardiovasc Surg; 1980; 80: 373/380.
Scheinman, "Catheter/based Techniques for Cure of Cardiac Arrhythmias," Advances in Cardiovascular Medicine, 1996, ISSN 1075/5527, pp. 93/100.
Guiraudon et al., "Surgical Ablation of Posterior Septal Accessory Pathways in the Wolf/Parkinson/White Syndrome by a Closed Heart Technique," Journal Thoracic Cardiovascular Surgery 92:406/413, 1986.
Graffigna et al., "Surgical Treatment of Wolff/Parkinson/White Syndrome: Epicardial Approach Without the Use of Cardiopulmonary Bypass," Journal of Cardiac Surgery 8: 108/116, 1993.
Siefert et al., "Radiofreuency Maz Ablation for Atrial Fibrillation," Circulation 90(4): I/594.
Surgical treatment of atrial fibrillation: a review; Europace (2004) 5, 520/S29 (abstract only).
Elvan et ai., "Radiofrequency Catheter Ablation of the Atria Reduces Inducibility and Duration of Atrial Fibrillation in Dog," Circulation 91: 2235/2244, 1995.
Cox et al., "Modification of the Maze Procedure for Atrial Flutter and Atrial Fibrillation. I. Rational and Surgical Results," The Journal of Thoracic Cardiovascular Summery 110: 473/484, 1995.
Sueda et al., "Simple Left Atrial Procedure for Chronic Atrial Fibrillation Associated with Mitral Valve Disease," The Annals of Thoracic Surgery 62(6): 1796/1800, 1996.
Kosakai et al., "Cox Maze Procedure for Chronic Atrial Fibrillation Associated with Mitral Valve Disease," The Journal of Thoracic Cardiovascular Surgery 108: 1049/1055, 1994.
Avitall et. al., "A Thoracoscopic Approach to Ablate Atrial Fibrillation via Linear Radiofrequency Lesion Generation on the Epicardium of Both Atria," PACE, Apr. 1996;19(Part II):626,#241.
Sie et al., "Radiofrequency Ablation of Atrial Fibrillation in Patients Undergoing Mitral Valve Surgery. First Experience," Circulation (Nov. 1996) 96:450,I/675,#3945.
Avitall et al., "New Monitoring Criteria for Transmural Ablation of Atrial Tissues," Circulation, 1996;94(Supp 1):I/493, #2889.
Williams, et al., "Left atrial isolation," | Thorac Cardiovasc Surg; 1980; 80: 373/380.
Sueda et al., "Efficacy of a Simple Left Atrial Procedure for Chronic Atrial Fibrillation in Mitral Valve Operations," Ann Thorac Surg, 1997;63:1070/1075.
Block et al., "Percutaneous Approaches to Valvular Heart Disease," Current Cardiology Reports, vol. 7 (2005) pp. 108/113.
Bonhoeffer et al, "Percutaneous Insertion of the Pulmonary Valve," Journal of the American College of Cardiology :United States), May 15, 2002, pp. 1664/1669.
Bonhoeffer et al, "Percutaneous Mitral Valve Dilatation with the Multi/Track System," Catheterization and cardiovascular Interventions/Official Journal of the Society for Cardiac Angiography & Interventions (United States), Dd. 1999, pp. 178/183.
Boudjemline et al, "Images in Cardiovascular Medicine. Percutaneous Aortic Valve Replacement in Animals," Circulation (United States), Mar. 16, 2004, 109, p. e161.
Boudjemline et al, "Percutaneous Aortic Valve Replacement: Will We Get There?" Heart (British Cardiac Society) (/England), Dec. 2001, pp. 705/706.
Boudjemline et al, "Percutaneous Implantation of a Biological Valve in the Aorta to Treat Aortic Valve Insufficiency/A /Sheep

(56) References Cited

OTHER PUBLICATIONS

Study," Medical Science Monitor/International Medical Journal of Experimental and Clinical Research (Poland), Apr. 2002, pp. BR113/BR116.
Boudjemline et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline et al, "The Percutaneous Implantable Heart Valve," Progress in Pediatric Cardiology (Ireland), 2001, pp. 39/93.
Coats et al, "The Potential Impact of Percutaneous Pulmonary Valve Stent Implantation on Right Ventricular Outflow Tract Re/Intervention," European Journal of Cardio/Thoracic Surgery (England), Apr. 2005, pp. 536/543.
Khambadkone, "Nonsurgical Pulmonary Valve Replacement: Why, When, and How?" Catheterization and cardiovascular Interventions/Official Journal of the Society for Cardiac Angiography & Interventions (United States), Jul. 2004, pp. 401/408.
Khambadkone et al, "Percutaneous Implantation of Pulmonary Valves," Expert Review of Cardiovascular Therapy :England), Nov. 2003, pp. 541/548.
Khambadkone et al, "Percutaneous Pulmonary Valve Implantation: Early and Medium Term Results," Circulation 108 (17 Supplement), Oct. 28, 2003, p. IV/375.
Lutter et al, "Percutaneous Aortic Valve Replacement: An Experimental Study. I. Studies on Implantation," The Journal of Thoracic and Cardiovascular Surgery, Apr. 2002, pp. 768/776.
Lutter et al, "Percutaneous Valve Replacement: Current State and Future Prospects," Annals of Thoracic Surgery (Netherlands), Dec. 2004, pp. 2199/2206.
Palacios, "Percutaneous Valve Replacement and Repair, Fiction or Reality?" Journal of American College of 2,ardiology, vol. 44, No. 8 (2004) pp. 1662/1663.
Saliba et al, "Treatment of Obstructions of Prosthetic Conduits by Percutaneous Implantation of Stents," Archives des Maldies du Coeur et des Vaisseaux (France), 1999, pp. 591/596.
Yonga et al, Effect of Percutaneous Balloon Mitral Valvotomy on Pulmonary Venous Flow in Severe Mitral Stenosis, East African Medical Journal (Kenya), Jan. 1999, pp. 28/30.
Yonga et al, "Percutaneous Transluminal Balloon Valvuloplasty for Pulmonary Valve Stenosis: Report on Six Cases," East African Medical Journal (Kenya), Apr. 1994, pp. 232/235.
Pavcnik et al., "Aortic and venous valve for percutaneous insertion," Min. Invas. Ther. & Allied Techol. 2000, 9 (314):287/292.
Andersen et al, "Transluminal implantation of artificial heart valves. Description of a new expandable aortic valve and initial results with implantation by catheter technique in closed chest pigs." Euro. Heart J. (1992) 13:704/708.
Babaliaros et al., "State of the Art Percutaneous Intervention for the Treatment of Valvular heart Disease: A Review of the Current Technologies and Ongoing Research in the Field of Percutaneous Heart Valve Replacement and Repair," Cardiology 2007; 107:87/96.
Bailey, "Percutaneous Expandable Prosthetic Valves," In: Topol EJ, ed. Textbook of Interventional Cardiology. vol. IL Second edition WB Saunders, Philadelphia, 1994:1268/1276.
Bonhoeffer et al, "Percutaneous Mitral Valve Dilatation with the Multi/Track System," Catheterization and Cardiovascular Interventions /Official Journal ofthe Society for Cardiac Angiography & Interventions (United States), Oct. 1999, pp. 178-183.
Bonhoeffer et al, "Percutaneous Replacement of Pulmonary Valve in a Right/Ventricle to Pulmonary/Artery Prosthetic Conduit with Valve Dysfunction," Lancet (England), Oct. 21, 2000, pp. 1403-1405.
Bonhoeffer et al, "Technique and Results of Percutaneous Mitral Valvuloplasty With the Multi/Track System," Journal of Interventional Cardiology (United States), 13(4):263/268 (Aug. 2000).
Bonhoeffer et al, "Transcatheter Implantation of a Bovine Valve in Pulmonary Position: A Lamb Study," Circulation (United States), Aug. 15, 2000, pp. 813-816.

Boudjemline et al, "Images in Cardiovascular Medicine. Percutaneous Aortic Valve Replacement in Animals," Circulation (United States), Mar. 16, 2004, 109.
Boudjemline et al, "Is Percutaneous Implantation of a Bovine Venous Valve in the Inferior Vena Cava a Reliable Technique to Treat Chronic Venous Insufficiency Syndrome?" Medical Science Monitor /International Medical Journal of Experimental and Clinical Research (Poland), Mar. 2004, pp. BR61-BR66.
Boudjemline et al, Off/pump Replacement of the Pulmonary Valve in Large Right Ventricular Outflow Tracts: A Hybrid Approach? Journal of Thoracic and Cardiovascular Surgery (United States), Apr. 2005, pp. 831-837.
Boudjemline ft al, "Percutaneous Aortic Valve Replacement: Will We Get There?" Heart (British Cardiac Society) (England), Dec. 2001, ngs. 705/6.
Boudjemline et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline et al, "Percutaneous Implantation of a Biological Valve in Aortic Position: Preliminary Results in a Sheep Study," European Heart Journal 22, Sep. 2001, p. 630.
Boudjemline et al, "Percutaneous Implantation of a Valve in the Descending Aorta in Lambs," European Heart Journal (England), Jul. 2002, pp. 1045-1049.
Boudjemline et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline et al, "Percutaneous Valve Insertion: A New Approach," Journal of Thoracic and Cardiovascular Surgery (United States), Mar. 2003, pp. 741/743.
Boudjemline, et al, "Steps Toward Percutaneous Aortic Valve Replacement," Circulation (United States), Feb. 12, 2002, pp. 775-778.
Boudjemline et al, "The Percutaneous Implantable Heart Valve," Progress in Pediatric Cardiology (Ireland), 2001, n!!s. 89-93.
Boudjemline ft al, "Transcatheter Reconstruction of the Right Heart," Cardiology in the Young (England), Jun. 2003, pp. 308-311.
Coats et al, "The Potential Impact of Percutaneous Pulmonary Valve Stcnt Implantation on Right Ventricular Outflow Tract Re/Intervention," European Journal of Cardin/Thoracic Surgery (England), Apr. 2005, pp. 536-543.
Commeau et al, "Percutaneous balloon dilatation of calcific aortic valve stenosis: anatomical and haemodynamic evaluation," 1988, British Heart Journal, 59:227/238.
Cribier et al, "Percutaneous Transcatheter Implantation of an Aortic Valve Prosthesis for Calcific Aortic Stenosis: First Human Case Description," Circulation (2002) 3006/3008.
Davidson et al, "Percutaneous therapies for valvular heart disease," Cardiovascular Pathology 15 (2006) 123/129.
Hanzel et al., "Complications of percutaneous aortic valve replacement: experience with the Criber/EdwardsTM percutaneous heart valve," EuroIntervention Supplements (2006), 1 (Supplement A) A3/A8.
Huber et al., "Do Valved Stents Compromise Coronary Flow?" Eur. I Cardiothorac. Surg. 2004;25:754/759.
Khambadkone et al, "Percutaneous Pulmonary Valve Implantation: Impact of Morphology on Case Selection," Circulation 108 (17 Supplement), Oct. 28, 2003, p. IV/642/1V/643.
Medtech Insight, "New Frontiers in Heart Valve Disease," 7(8): 226/260 (2005).
Palacios, "Percutaneous Valve Replacement and Repair, Fiction or Reality?" Journal of American College of Cardiology, vol. 44, No. 8 (2004) pp. 1662-1663.
Ruiz, "Transcathether Aortic Valve Implantation and Mitral Valve Repair: State of the Art," Pediatric Cardiology, 26(3):289/294 (2005).
Stassano et al., "Mid/term results ofthe valve/on/valve technique for bioprosthetic failure," Lur. J. Cardiothorac. Surg. 2000; 18:453/457.
Webb et al, "Percutaneous Aortic Valve Implantation Retrograde from the Femoral Artery," Circulation (2006), 113;842/850.

(56) References Cited

OTHER PUBLICATIONS

Yonga et al, "Percutaneous Balloon Mitral Valvotomy: Initial Experience in Nairobi Using a New Multi/Track Catheter System," East African Medical Journal (Kenya), Feb. 1999, pp. 71-74.
Yonga ft al, "Percutaneous Transvenous Mitral Commissurotomy in Juvenile Mitral Stenosis," East African Medical Journal (Kenya), Apr. 2003, pp. 172-174.
Expert report of Dr. Nigel Buller, dated Jan. 12, 2009, Edwards' United Kingdom action for invalidity, Claim No. HC 08C00934 (83 pages).
Expert report of Dr. Nigel Buller, non/con fidential annex/infringement, dated Jan. 12, 2009, Edwards' United Kingdom action for invalidity, Claim No. HC 08C00934 (95 pages).
Expert report of Dr. Rodolfo Quijano, dated Jan. 9, 2009, Edwards' United Kingdom action for invalidity, Claim No. HC 08C00934 (18 pages).
First Expert report of Prof. David Williams, dated Jan. 12, 2009, Edwards' United Kingdom action for invalidity, Claim No. HC 08C00934 (41 pages).
First Expert report of Prof. Martin Rothman, dated Jan. 12, 2009, Edwards' United Kingdom action for invalidity, Claim No. HC 08C00934 (64 pages).
Fourth Expert report of Prof. Martin Rothman, dated Apr. 22, 2009, Edwards' United Kingdom action for invalidity, Claim No. I/IC 08C00934 (10 pages).
Second Expert report of Dr. Nigel Buller, dated Feb. 25, 2009, Edwards' United Kingdom action for invalidity, Claim No. HC 08C00934 (24 pages).
Second Expert report of Dr. Rodolfo Quijano, dated Feb. 26, 2009, Edwards' United Kingdom action for invalidity, Claim No. HC 08C00934 (6 pages).
Second Expert report of Prof. David Williams, dated Feb. 5, 2009, Edwards' United Kingdom action for invalidity, Claim No. HC 08C00934 (15 pages).
Second Expert report of Prof. Martin Rothman, dated Feb. 5, 2009, Edwards' United Kingdom action for invalidity, Claim No. HC 08C00934 (11 pages).
Third Expert report of Dr. Nigel Buller, dated Apr. 21, 2009, Edwards' United Kingdom action for invalidity, Claim No. HC 08C00934 (6 pages).
Third Expert report of Dr. Rudolf( ) Quijano, dated Apr. 27, 2009, Edwards' United Kingdom action for invalidity, Claim No. HC 08C00934 (3 pages).
Third Expert report of Prof. David Williams, dated Apr. 22, 2009, Edwards' United Kingdom action for invalidity, Claim No. HC 08C00934 (9 pages).
First Expert report of Dr. Nigel Person Buller (30 pages), *Corevalve, Inc.* v. *Edwards Lifesciences AG and Edwards Lifesciences PVT, Inc.*, High Court of Justice /Chancery Division Patents Court, United Kingdom, Case No. HC/07/001243 (30 pages).
Second Expert report of Dr. Nigel Person Buller (5 pages), *Corevalve. Inc.* v. *Edwards Lifesciences AG and Edwards Lifesciences PVT, Inc.*, High Court of Justice /Chancery Division Patents Court, United Kingdom, Case No. HC/07/001243 (Jun. 18, 2008).
Drawing by Dr. Buller (Edwards Expert) of his interpretation of the "higher stent" referred to as col. 8, lines 13/222 of Andersen EP 592410131 (1 page), *Corevalve, Inc.* v. *Edwards Lifesciences AG and Edwards Lifesciences PVT, Inc.* High Court of Justice /Chancery Division Patents Court, United Kingdom, Case No. IIC/07/001243.
Drawing by Dr. Buller (Edwards Expert) of "higher stent" on the schematic representation of the aortic valve area set out in Figure 2 of Rothman's first expert report (1 page), *Carevalve. Inc.* v. *Edwards Lifesciences AG and Edwards Lifesciences PVT, Inc.*, High Court of Justice /Chancery Division Patents Court, United Kingdom, Case No. HC/07/001243.
First Expert report of Professor John R. Pepper (20 pages), *Carevalve. Inc.* v. *Edwards Lifesciences AG and Edwards Lifesciences PVT, Inc.*, High Court of Justice /Chancery Division Patents Court, United Kingdom, Case No. HC/07/001243 (Apr. 28, 2008).
Second Expert report of Professor John R. Pepper (3 pages), *Corevalve, Inc.* v. *Edwards Lifesciences/AG and Edwards Lifesciences PVT, Inc.*, High Court of Justice /Chancery Division Patents Court, United Kingdom, Case No. HC/07/001243 (Jun. 10, 2008).
First Expert report of Dr. Anthony C. Lunn (7 pages), *Corevalve. Inc.* v. *Edwards Lifesciences AG and Edwards Lifesciences PVT, Inc.*, High Court of Justice /Chancery Division Patents Court, United Kingdom, Case No. HC/07/001243 (Apr. 28, 2008).
First Witness statement of Stanton Rowe (9 pages), *Corevalve. Inc.* v. *Edwards Lifesciences AG and Edwards Lifesciences PVT, Inc.*, High Court of Justice /Chancery Division Patents Court, United Kingdom, Case No. 11C/07/001243 (May 27, 2008).
Second Witness statement of Stanton Rowe (3 pages), *Corevalve, Inc.* v. *Edwards Lifesciences AG and Edwards Lifesciences PVT Inc.*, High Court of Justice /Chancery Division Patents Court, United Kingdom, Case No. HC/07/001243 (Jun. 20, 2008).
PVT slides naming Alain Cribier, Martin Leon, Stan Rabinovich and Stanton Rowe (16 pages), *Corevalve, Inc.* v. *Edwards Lifesciences AG and Edwards Lifesciences PVT Inc.*, High Court of Justice /Chancery Division Patents Court, United Kingdom, Case No. HC/07/001243.
First Expert report of Professor Martin Terry Rothman (75 pages), *Corevalve. Inc.* v. *Edwards Lifesciences AG and Edwards Lifesciences PVT, Inc.*, High Court of Justice /Chancery Division Patents Court, United Kingdom, Case No. HC/07/001243 (Apr. 28, 2008).
Reply Expert report of Professor Martin Terry Rothman (9 pages), *Corevalve, Inc.* v. *Edwards Lifesciences AG and Edwards Lifesciences PVT Inc.*, High Court of Justice /Chancery Division Patents Court, United Kingdom, Case No. HC/07/001243 (May 27, 2008).
First Expert report of Richard A. Hillstead (41 pages), *Corevalve, Inc.* v. *Edwards Lifesciences AG and Edwards Lifesciences PVT Inc.*, High Court of Justice /Chancery Division Patents Court, United Kingdom, Case No. HC/07/001243 (Apr. 28, 2008).
Reply Expert report of Richard A. Hillstead (9 pages), *Corevalve, Inc.* v. *Edwards Lifesciences AG and Edwards Lifesciences PVT Inc.*, High Court of Justice /Chancery Division Patents Court, United Kingdom, Case No. IIC/07/C01243 (May 27, 2008).
Trapp, et al., "To Use or Not to Use the Pump Oxygenator in Coronary Bypass Operations," The Annals of Thoracic Surgery, vol. 19, No. 1 (1975), pp. 108/111.
Zumbro, et al., "A Prospective Evaluation of the Pulsatile Assist Device," The Annals of Thoracic Surgery, vol. 28, No. 3 (1979), pp. 269/273.
Akins, et al., "Preservation of interventricular septal function in patients having coronary artery bypass grafts without cardiopulmonary bypass," American Heart Journal, vol. 107, No. 2 (1984), pp. 304/309.
Archer, et al., "Coronary Artery Revascularization Without Cardiopulmonary Bypass," Texas Heart Institute Journal, vol. 11, No. 1 (1984), 2p. 52/57.
Buffolo, et al., "Direct Myocardial Revascularization without Cardiopulmonary Bypass," Thorac. Cardiovasc. Surgeon 33 (1985), pp. 26/29.
Benetti, "Direct coronary surgery with saphenous vein bypass without either cardioipulmonary bypass or cardiac arrest," J. Cardiovasc. Stu. vol. 26, No. 3 (1985), pp. 217/222.
Kresh, et al., "Heart/mechanical Assist Device Interaction," Trans. Am. Soc. Artif. Intern. Organs, vol. 32 (1986), pp. 437/443.
Ballantyne, et al., "Delayed Recovery of Severely 'Stunned' Myocardium with the Support of a Left Ventricular Assist Device after Coronary Artery Bypass Graft Surgery," Journal of American College of Cardiology, vol. 10, No. 3 (1987), pp. 710/712.
Ruzevich, et al., "Long/term Follow/up of Survivors of Postcardiotomy Circulatory Support," Trans. Am. Soc. Artif. Intern. Organs, vol. 34 (1988), pp. 116/124.
McGee, et al., "Extended Clinical Support with an Implantable Left Ventricular Assist Device," Trans. Am. So. Artif. Intern. Organs, vol. 35 (1989), pa. 614/616.
Richenbacher, et al., "Current Status of Cardiac Surgery: A 40 Year Review," JACC, vol. 14, No. 3 (1989), pp. 535/544.
Scholz, et al., "Transfemoral Placement of the Left Ventricular Assist Device 'Hemopump' During Mechanical Resuscitation," Thorac. Cardiovasc. Surgn., vol. 38 (1990), pp. 69/72.

(56) References Cited

OTHER PUBLICATIONS

Anstadt, et al., "Direct Mechanical Ventricular Actuation for Cardiac Arrest in Humans," Chest, vol. 100, No. 1 (1991), pp. 86/92.
Benetti, et al., "Direct Myocardial Revascularization without Extracorporeal Circulation," Chest, vol. 100, No. 2 (1991) pp. 312/316.
Pfister, et al., "Coronary Artery Bypass Without Cardiopulmonary Bypass," Ann. Thorac. Surg., vol. 54, No. 6 (1992), pp. 1085-1092.
Lönn, et al., "Coronary Artery Operation Supported by the Hemopump: An Experimental Study on Pig," Ann. Thorac. Surg., vol. 58, No. 1 (1994), pp. 516-518.
"Regional Cardiac Wall Immobilization for Open Chest and Closed Chest Coronary Artery Bypass Grafting on the Beating Heart: The 'Octopus' Method," Circulation, vol. 92, No. 8 Supplement 1 (1995), p. 1/177.
Robinson, et al., "A Minimally Invasive Surgical Method for Coronary Revascularization—Preliminary Experience in Five Patients," Circulation, vol. 92, No. 8 (1995), 1/176.
Borst, et al., "Coronary Artery Bypass Grafting Without Cardiopulmonary Bypass and Without Interruption of Native Coronary Flow Using a Novel Anastomosis Site Restraining Device ('Octopus')," MCC, vol. 27, No. 6 (1996), pp. 1356/1364.
Gacioch, at al., "Cardiogenic Shock Complicating Acute Myocardial Infarction: The Use of Coronary Angioplasty and the Integration of the New Support Devices into Patient Management," MCC, vol. 19, No. 3 (1992), pp. 647/653.
Fanning, at al., "Reoperative Coronary Artery Bypass Grafting Without Cardiopulmonary Bypass," Ann. Thorac. Surg., Vo. 55, No. 2 (1993), pp. 486/489.
Fonger, at al., "Enhanced Preservation of Acutely Ischemic Myocardium With Transseptal Left Ventricular Assist," Ann. Thorac. Surg., vol. 57, No. 3 (1994), pp. 570/575.
Lavergne, at al., "Transcatheter Radiofrequency Ablation of Atrial Tissue Using a Suction Catheter," PACE, vol. 12 (1989), Part II, pp. 177/186.
Stevens, et al., Abstract: "Closed Chest Coronary Artery Bypass with Cardioplegic Arrest in the Dog," 67th Scientific Sessions.
Trapp, et al., "Placement of Coronary Artery Bypass Graft Without Pump Oxygenator," Ann. Thorac. Surg., vol. 19, No. 1 (1975), pp. 1/9.
Grundeman, et al., "Experimental videothoracoscopic cannulation of the left atrial appendix," Surg. Endosc., (1993) 7:511/513.
Calafiore, at al., /The LAST Operation: Techniques and Results Before and After the Stabilization Era. Ann. Thorac. Surg. (1998); 66:998/1001.
Konishi, at al., "Hybrid/Type Stabilizer for Off/Pump Direct Coronary Artery Bypass Grafting," Ann. Thorac. Surg., (1998) 66:961/2.
DelRossi, at al., "A New Retractor to Aid in Coronary Artery Surgery," Ann. Thorac. Surg., vol. 36, No. 1 (1983), pp. 101/102.
Westaby, et al, "Less Invasive Coronary Surgery: Consensus From the Oxford Meeting," Ann. Thorac. Surg. (1996) 62:924/31.
Roux, at al., "New Helper Instrument in Cardiac Surgery," Ann. Thorac. Surg., (1989) 48:595/6.
Kolessov, "The Surgery of Coronary Arteries of the Heart," Leningrad, ad, Meditsina, 1997, p. 360 (Russian article).
Kolessov, "The Surgery of Coronary Arteries of the Heart," Leningrad, Meditsina, 1997, p. 360 (English translation).
Mammary Artery/Coronary Artery Anastomosis as Method of Treatment for Angina Pectoris, V.I Kolessov, MD/Thoracic and Cardiovascular Surgery, vol. 54, No. 4, Oct. 1967 pp. 535/544.
Direct Myocardial Revascularization by Saphenous Vein Graft, R.G. Favaloro, MD DG Effler, MD; LK Groves, MD; WG Sheldon, MD; and FM Sones, Jr., MD / The Annals of Thoracic Surgery, vol. 10, No. 2, Aug. 1970.
A Simple Technique and Device to Provide a Bloodless Operative Field in Coronary Artery Surgery Without Cross/Clamping the Aorta, M. Riahi, RJ Schlosser and LA Tomastis/The Journal of Thoracic and Cardiovascular Surgery, vol. 66, No. 6, Dec. 1973, pp. 974/978.
To Use or Not to Use the Pump Oxygenator in Coronary Bypass Operations, Drs. WG Trapp and R. Bisarya/The Annals of Thoracic Surgery, vol. 19, No. 1, Jan. 1975, pp. 108/109.
A Prospective Evaluation of the Pulsatile Assist Device, GL Zumbro, Jr., MD; G Shearer, CCP; ME Fishback, MD; and RF Galloway, MD / The Annals of Thoracic Surgery, vol. 28, No. 2 Aug. 1979, pp. 269/273.
Preservation of Interventricular Septal Function in Patients Having Coronary Artery Bypass Grafts Without Cardiopulmonary Bypass, CW Akins, MD; CA Boucher, MD; and GM Pohost, MD / American Heart Journal, vol. 107, No. 2, Feb. 1984, pp. 304/309.
Coronary Artery Revascularization Without Cardiopulmonary Bypass, R. Archer, DO; DA Ott, MD; R. Parravicini, MD; DA Cooley, MD; GJ Reul, MD; OH Frazier, MD; JM Duncan, MD; JJ Livesay, MD and WE Walker, MD, Texas Heart Institute Journal, vol. 11, No. 1, Mar. 1984, pp. 52/57.
Direct Myocardial Revascularization Without Cardiopulmonary Bypass, E. Buffolo; JCS Andrade, J Succi; LEV Leao; and C Gallucci. Thoac. Cardiovasc. Surgeon, 33 (1985) pp. 26/29.
Direct Coronary Surgery with Saphenous Vein Bypass Without Eigher Cardiopulmonary Bypass or Cardiac Arrest, FJ Benetti, The Journal of Cardiovascular Surgery, vol. 26, No. 3, May/Jun. 1985, pp. 217/222.
Heart/Mechanical Assist Device Interaction, JY Kresh; PLM Kerkhof; SM Goldman; and SK Brockman, Trans. Am. Soc. Artif. Intern. Organs, vol. XXXII, 1986, pp. 437/443.
Delayed Recovery of Severaly 'Stunned' Myocardium with the Support of a Left Ventricular Assist Device after Coronary Artery Bypass Graft Surgery, CM Ballantyne MD; MS verani, MD, FACC; HD Short, MD; C Hyatt, BSN, RN; GP Noon, MD, FACC, Journal of the American College of Cardiology, vol. 10, No. 3, Sep. 1987, pp. 710/712.
Long/Term Follow/up of Survivors of Postcardiotomy Circulatory Support, SA Ruzevich; KR Kanter; DG Pennington; MT Swartz; LR McBride; and DT Termuhlen, Trans. Am. Soc. Artif. Intern. Organs, vol. XXXIV, 1988, pp. 116/124.
Extended Clinical Support with an Implantable Left Ventricular Assist Device, MG McGee; SM Parris; T Nakatani; T Myers; K Dasse; WD Hare; JM Duncan; VL. Poirier; and OH Frazier, Trans Am. Soc. Artif. Intern. Organs, vol. XXXV, 1989, pp. 614/616.
Current Status of Cardiac Surgery: A 40/Year Review, WE Richenbacher, MD; JL Myers, MD, FACC; JA Walhausen, MD, FACC, Journal of American College of Cardiology, vol. 14, No. 3, Sep. 1989, pp. 535/544.
Transfemoral Placement of the Left Ventricular Assist Device "Hemapump" During Mechanical Resuscitation, KH Scholz; U Tebbe; M Chemnitius; H Kreuzer; T Schroder; JP Hering; P Uhlig; G Hellige; HJ Grone; R Autschbach; B Schorn; W Ruschewski; and H Dalichau, Thoracic and Cardiovascular Surgeon, vol. 38 (1990) pp. 69/72.
Direct Mechanical Ventricular Actuation for Cardiac Arrest in Humans, MP Anstadt, MD; RL Bartlett, MD; JP Malone, MD, FCCP; and GL Anstadt, VMD; Chest, vol. 100, No. 1, Jul. 1991.
Direct Myocardial Revascularization Without Extracorpoeal Circulation, FJ Benetti, MD; G Naselli, MD; M Wood, MD; and L Geffner, MD, Chest, vol. 100. No. 2, Aug. 1991, pp. 312/316.
Coronary Artery Bypass Without Cardiopulmonary Bypass, Pfister et al, The Annals of Thoracic Surgery, vol. 54 #6 Dec. 1992 pp. 1085/1092.
Coronary Artery Operation Supported by the Hemopump: An Experimental Study on Pig, U Lonn, MD; B Peterzen, MD; H Granfeldt, MD; and H Casimir/Ahn, MD, Ph.D. The Annals of Thoracic Surgery, vol. 58, No. 1, Jul. 1994, pp. 516/523.
Regional Cardiac Wall Immobilization for Open Chest and Closed Chest Coronary Artery Bypass Grafting on the Beating Heart: The 'Octopus' Method, Circulation, vol. 92. No. 8 Supplement 1, I/177 (Oct. 15, 1995).
A Minimally Invasive Surgical Method for Coronary Revascularization—Preliminary Experience in Five Patients, MC Robinson, DR Gross, and W Zeman, Circulation, (Oct. 15, 1995) vol. 92, No. 8, I/176.
Coronary Artery Bypass Grafting Without Cardiopulmonary Bypass and Without Interruption of Native Coronary Flow Using a Novel

(56) References Cited

OTHER PUBLICATIONS

Astamosis Site Restraining Device ("Octopus"), C. Borst et al., Journal of the American College of Cardiology, vol. 27, No. 6, 1356/1364 (May 1996).

Cardiogenic Shock Complicating Acute Myocardial Infarction: the Use of Coronary Angioplasty and the Integration of the New Support Device into Patient Management, GM Gacioch, MD; Stephen G. Ellism, MD, FACC; L Lee, MD; ER Bates, MD, FACC; M Kirsh, MD, FACC; JA Walton, MD, FACC; EH Topol, MD, FACC, Journal of the American College of Cardiology, vol. 19, No. 3, Mar. 1, 1992.

Reoperative Coronary Artery Bypass Grafting Without Cardiopulmonary Bypass, WJ Fanning, MD; GS Kakos, MD; and TE Williams, Jr., MD, Ph.D., The Annals of Thoracic Surgery, vol. 55, No. 2, Feb. 1993, pp. 486/489.

Enhanced Preservation of Acutely Ischemic Myocardium with Transeptal Left Ventricular Assist, JD Fonger, MD; Y Thou, MD; H Matsuura, MD; GS Aldea, MD; and RJ Shemin, MD, The Annals of Thoracic Surgery, vol. 57, No. 3, Mar. 1994, pp. 570/575.

Transcatheter Radiofrequency Ablation of Atrial Tissue Using a Suction Catheter, Th Lavergne et al. (PACE, vol. 12, Jan. 1989, Part II, pp. 177/186.

Abstract: "Closed Chest Coronary Artery Bypass With Cardioplegic Arrest in the Dog", Stevens et al. 67th Scientific Sessions.

Placement of Coronary Artery Bypass Graft without Pump Oxygenator, Trapp et al., Journal of the Society of Thoracic Surgeons and the Southern Thoracic Surgical Assn. vol. 19. No. 7 Jan. 1975.

Experimental Videothoracoscopic Cannulation of the Left Atrial Appendix: A Feasible Rapid Approach for Initiating Left Heart Bypass? PF Grundeman; DW Meijer; JJG Bannenberg; R tukkie; and PJ Klopper, Surgical Endoscopy (1993) 7: 511/513.

The LAST Operation: Techniques and Results Before and After the Stabilization Era, Antonio M. Calafiore, MD; Giuseppe Vitolla, MD; Valerio Massei, MD; Giovanni Teodori, MD; Gabriele Di Giammarco, MD; Teresa Iovino, MD and Angela Iaco, MD; Ann Thorac Surg 1998; 66:998/1001.

Hybrid/Type Stabilizer for Off/Pump Direct Coronary Artery Bypass Grafting, by: Toshio Konishi, M.D.; Kazuhiko Higuchi, M.D.; Mutumu Fukata, M.D.; Shinji Akisima, M.D.; and Shiji Fukuda, M.D.; Ann Thorac Surgery 1998; 66:961/2.

A.J. Delrossi, M.D., and G.M. Lemore, M.D., A New Retractor to Aid in Coronary Artery the Annals of Thoracic and Cardiovascular Surgery, vol. 36 Jul. 1983, pp. 101/102.

Stephen Westaby, FRCS and Federico J. Benetti, M.D.; Less Invasive Coronary /STEPHEN Surgery: Consensus from the Oxford Meeting, Annals of Thoracic Surgery 1996, 62: 924/31.

Kolessov V.I. The Surgery of Coronary Arteries of the Heart, Leningrad, Meditsina, 1977, pp. 360. (Russian Article).

Kolessov V.I. The Surgery of Coronary Arteries of the Heart, Leningrad, Meditsina, 1977, pp. 360. (English Translation).

New Helper Instrument in Cardiac Surgery—D. Roux, M.D.; G. Fournial, M.D.; Y. Glock, M.D.; P. Dalous, M.D.; and P. Puel, M.D., Annal Thorac Surg. 1989;48:595/6.

\* cited by examiner

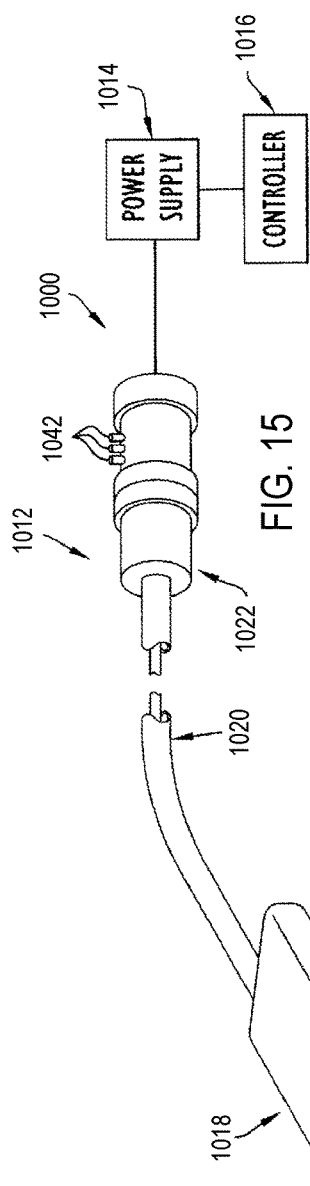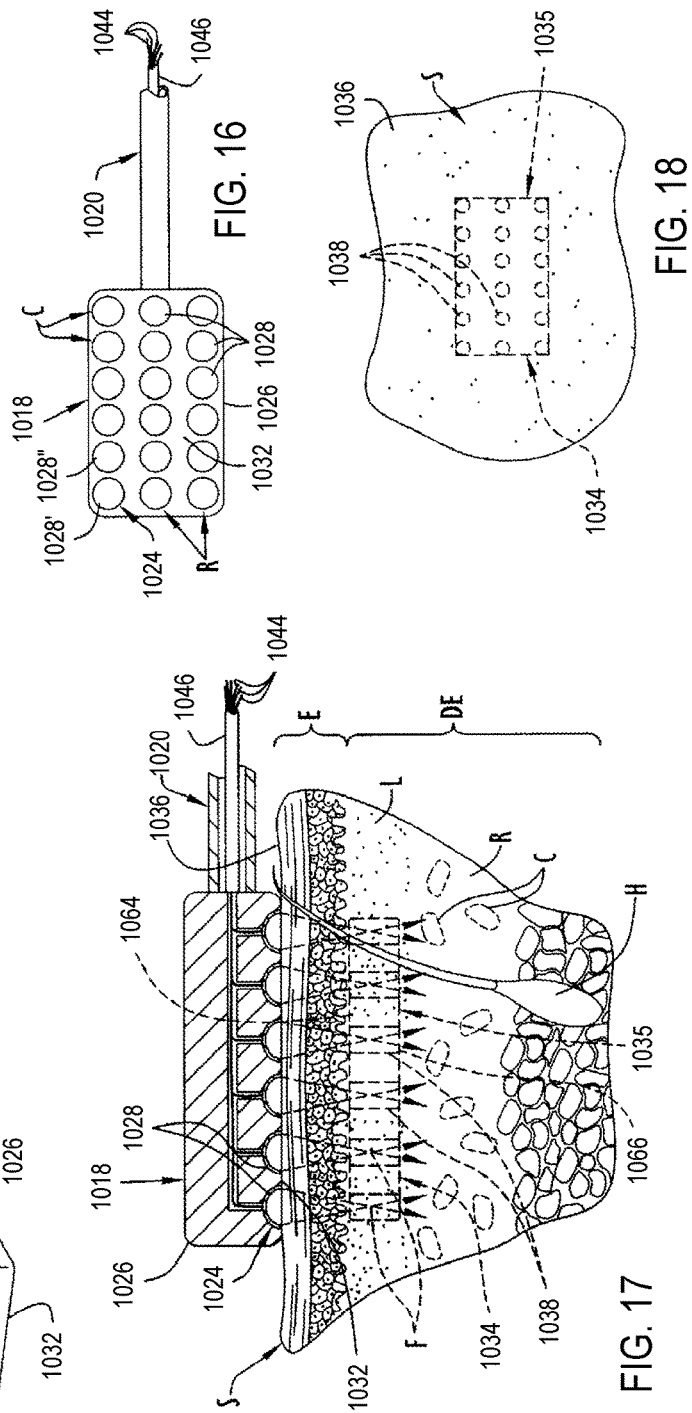

METHOD FOR ABLATING TARGET TISSUE OF A PATIENT

CROSS-REFERENCE TO RELATED APPLICATIONS SECTION

This application is a continuation of U.S. patent application Ser. No. 14/174,268, filed on Feb. 6, 2014, the contents of which are incorporated herein by reference.

U.S. patent application Ser. No. 14/174,268 is a continuation of U.S. application Ser. No. 13/585,622, filed on Aug. 14, 2012, the contents of which are incorporated herein by reference.

U.S. patent application Ser. No. 13/585,622 is a continuation of U.S. application Ser. No. 12/570,888, filed on Sep. 30, 2009, now U.S. Pat. No. 8,241,274, the contents of which are incorporated herein by reference.

U.S. patent application Ser. No. 12/570,888 filed Sep. 30, 2009 claims the benefit of U.S. Provisional Patent Application Ser. No. 61/194,783 filed on Sep. 30, 2008, the disclosure of which is incorporated herein by reference in its entirety.

U.S. patent application Ser. No. 12/570,888 filed Sep. 30, 2009 is also a continuation-in-part of U.S. patent application Ser. No. 11/298,282 filed Dec. 9, 2005 now U.S. Pat. No. 8,221,402, which is a continuation-in-part of U.S. patent application Ser. No. 11/128,686 filed May 13, 2005 now U.S. Pat. No. 7,706,882

U.S. patent application Ser. No. 11/128,686 filed May 13, 2005 claims the benefit of U.S. Provisional Patent Application Ser. No. 60/571,182 filed on May 14, 2004, the disclosure of which is incorporated herein by reference in its entirety.

U.S. patent application Ser. No. 11/128,686 filed May 13, 2005 is a continuation-in-part of U.S. patent application Ser. No. 10/464,213 filed Jun. 18, 2003, now U.S. Pat. No. 6,936,046, which is a continuation of U.S. patent application Ser. No. 09/629,194 filed Jul. 31, 2000, now U.S. Pat. No. 6,595,934, which is a continuation-in-part of U.S. patent application Ser. No. 09/487,705 filed Jan. 19, 2000, now abandoned, the disclosures of which are incorporated herein by reference in their entirety.

U.S. patent application Ser. No. 11/128,686 filed May 13, 2005 is also a continuation-in-part of U.S. patent application Ser. No. 10/156,315 filed May 28, 2002, now U.S. Pat. No. 7,507,235, which is a continuation of U.S. patent application Ser. No. 09/879,294 filed Jun. 12, 2001, now U.S. Pat. No. 6,447,443, which claims the benefit of the filing dates of U.S. Provisional Patent Application Ser. No. 60/261,343 filed Jan. 13, 2001, Ser. No. 60/263,739 filed Jan. 24, 2001, Ser. No. 60/282,029 filed Apr. 6, 2001 and Ser. No. 60/286,952 filed Apr. 26, 2001, the disclosures of which are incorporated herein by reference in their entirety.

U.S. patent application Ser. No. 11/128,686 filed May 13, 2005 is also a continuation-in-part of U.S. patent application Ser. No. 10/643,299 filed Aug. 19, 2003, now U.S. Pat. No. 7,338,434, which claims the benefit of the filing dates of U.S. Provisional Patent Application Ser. No. 60/424,243 filed Nov. 6, 2002 and Ser. No. 60/404,969 filed Aug. 21, 2002, the disclosures of which are incorporated herein by reference in their entirety.

TECHNICAL FIELD

The present disclosure relates generally to treatment of cardiac heart disease. More particularly, the present disclosure relates to implantable valve prostheses for implantation into the cardiac system.

BACKGROUND

Recently, there has been increasing interest in minimally invasive and percutaneous replacement of cardiac valves. Percutaneous replacement of a heart valve does not involve actual physical removal of the diseased or injured heart valve. Rather, the defective or injured heart valve typically remains in position while the replacement valve is inserted into a balloon catheter and delivered percutaneously via the vascular system to the location of the failed pulmonary valve. Such surgical techniques involve making a very small opening in the skin of the patient into which a valve assembly is inserted via a delivery device similar to a catheter. There, the replacement valve is expanded by the balloon to compress the native valve leaflets against the body opening in which it is inserted, anchoring and sealing the replacement valve. This technique is often preferable to more invasive forms of surgery, such as opening a large portion of the chest for cardiopulmonary bypass, for example.

In the context of percutaneous, pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is crimped or compressed around the balloon portion of a catheter until it is as close to the diameter of the catheter as possible. The valve is then delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Pat. Application No. 2003/0036791 A1 and European Patent Application No. 1 057 460-A1.

Assignee's co-pending U.S. patent application titled "Apparatus for Treatment of Cardiac Valves and Method of Its Manufacture", filed Nov. 18, 2005 and assigned U.S. Ser. No. 11/282,275, describes percutaneous heart valves for use as a replacement pulmonary valve. Like the valves described by Tower et al., the heart valves of this co-pending application incorporate a valved segment of bovine jugular vein, mounted within an expandable stent.

In addition to percutaneous valve implantation, heart valve repair can also be accomplished using catheter-based valve repair procedures. In the context of annuloplasty ring implantation on a valve annulus, for example, a variety of repair procedures can be used, such as procedures that require indirect visualization techniques to determine the exact location of the heart valve and annuloplasty ring during placement of the ring at the valve annulus. Indirect visualization techniques, as described herein, are techniques that can be used for viewing an indirect image of body tissues and/or devices within a patient. One example of such a technique is referred to as endoscopic visualization, which involves displaying images from endoscopic light guides and cameras within the thoracic cavity on a video monitor that is viewed by a surgeon. Effective use of this method depends on having sufficient open space within the working area of the patient's body to allow the surgeon to recognize the anatomical location and identity of the structures viewed on the video display, which can be difficult to accomplish in certain areas of the heart.

Another indirect visualization technique involves the use of fluoroscopy, which is an imaging technique commonly used by physicians to obtain real-time images of the internal structures of a patient through the use of a fluoroscope. Fluoroscopy can be effective in many situations, but does have some drawbacks. For one example, some tissues, such as the cardiac tissues, do not readily appear under fluoroscopy, making it very difficult to accurately align an annuloplasty ring prior to its implantation. To improve the visualization of the area of interest, radiopaque contrast dye can be used with x-ray imaging equipment. However, when treating the mitral valve, for example, repeated injections of contrast dye are not practical because of rapid wash-out of the dye in this area of high fluid flow. For another example, to make high-volume contrast injections of this kind, an annuloplasty catheter system would require multiple lumens, undesirably large lumens, and/or an additional catheter, none of which is desirable during catheterization procedures. Further, multiple high-volume contrast injections are somewhat undesirable for the patient due to potential complications in the renal system, where the radiopaque contrast medium is filtered from the blood.

A wide variety of other techniques are available for viewing images of cardiac structures, including ultrasonography such as trans-thoracic echocardiography (TTE), trans-esophageal echocardiography (TEE), cardiac magnetic resonance (CMR) including magnetic resonance imaging (MRI) or magnetic resonance angiography (MRA), and computed tomography (CT) including computer tomography angiography (CTA). These techniques, used alone or in combination with other available techniques, all typically have certain drawbacks relative to visualization and guidance during catheter-based valve repair procedures.

Yet another visualization technique that can be used for catheter-based valve repair involves mapping a valve annulus, such as a mitral valve annulus, and obtaining real time imaging during heating heart surgery through the use of electromagnetic (EM) imaging and navigation. This type of technique can be effective for viewing the significant movement of the annulus during both systole and diastole that occurs during procedures performed on a beating heart. With EM navigation, a patient is generally placed on a table having a plurality of sensors either on the surface of the table or at positions around the table. The sensors are connected to a processor and the processor knows the positions of the sensors relative to the table. A patient is then placed on the table and immobilized, and then an elongated flexible device having at least three EM coils spaced along its distal portion can then be inserted into the patient's body (into the vascular system for example). The coils are typically made from extremely small diameter material that can be wound around the outside of the device or wound around an interior layer of the device and then covered with an additional layer of material. A very thin wire or some other electrically conductive material can be used to communicate from an external AC power source to each of these coils. Alternatively, wireless sensors can be used to eliminate the need to provide a wire to communicate with the EM coils.

As the elongated device is moved through the body, the sensors can detect the EM signal that is created by the moving coil. The processor then calculates the position of the coils relative to each sensor. The location of the sensors can be viewed on a display device, and the EM navigation can be combined with other navigation/visualization technologies so that the location of the EM coils in a patient's body can be viewed in real time. Additional sensors may also be incorporated into a system using EM navigation to improve the accuracy of the system, such as temporarily attaching sensors to a patient's body and/or covering at least a portion of a patient with a blanket that contains additional sensors. The relationship between all of the sensors can be used to produce the image of the patient's body on the table. Examples of methods and systems for performing medical procedures using EM navigation and visualization systems for at least part of an overall navigation and visualization system can be found, for example, in U.S. Pat. No. 5,782,765 (Jonkman); U.S. Pat. No. 6,235,038 (Hunter et al.); U.S. Pat. No. 6,546,271 (Resifeld); U.S. Patent Application No. 2001/0011175 (Hunter et al.); U.S. Patent Application No. 2004/0097805, (Verard et al.), and U.S. Patent Application No. 2004/0097806 (Hunter et al.), the entire contents of which are incorporated herein by reference.

Another method for mapping the mitral valve annulus and obtaining real time imaging during beating heart surgery is through the use of electro-potential navigation. Electro-potential (EP) navigation involves the use of external sensors that are placed on the patient. When using EP navigation, a low frequency electrical field is created around the patient, and the coils on the instrument are connected to a DC energy source such that there is a constant energy signal emitting from the coils. The coils create a disturbance in the electrical field as they move through the field, and location of the instrument in the 3D coordinate space is calculated by determining the location of the disturbance in the energy field relative to the sensors.

As described above, delivery of a valve percutaneously to a remote access site in the body via the vascular system and delivery of devices for treating cardiac valve disease can be challenging because precise manipulation of the surgical tools is more difficult when the surgeon cannot see the area that is being accessed and when the heart is moving. Thus, there is a need for heart valve placement or repair systems having visualization capabilities that permit the surgeon to quickly, easily and securely implant a heart valve or repair a heart valve in a patient with minimal resulting trauma to the patient. In certain cases, there is a further need for heart valve placement systems that can implant such valves into a failed bioprosthesis, which also requires precise manipulation by a surgeon. In addition, there is a need for heart valve repair systems that can repair a failed or failing heart valve or a failed or failing bioprothesis. Such systems should further provide the surgeon with a high degree of confidence that a valve has been properly positioned within the patient's heart during surgery.

SUMMARY

While a variety of systems and devices have been developed to provide tracking and visualization in certain areas of the body for a number of different applications, these systems are not being used and are not generally adaptable to be used for placement or repair of heart valves in certain locations in the heart. That is, the types of navigation systems used for other areas of the body have different operating parameters and requirements that are different from those needed for percutaneous implantation of a valve or percutaneous repair of a valve within a patient's heart. The present disclosure advantageously addresses these operating parameters and requirements while minimizing the use of fluoroscopy and providing a 3-dimensional view of the heart structure.

In one aspect of the disclosure, a delivery system is provided for percutaneous delivery of a heart valve to a predetermined position in the heart of a patient, where the delivery system itself includes features that allow it to be accurately positioned in the heart. In another aspect of the disclosure, a delivery system is provided for percutaneous repair of a heart valve in the heart of a patient, where the repair system itself includes features that allow it to be accurately positioned in the heart. For example, a delivery or repair system can include multiple ferromagnetic elements spaced from each other along the length of an elongated body. Preoperative and intraoperative imaging can help guide the device or delivery system to the desired position in the heart using an external magnetic field, which drives the ferromagnetic objects on the device or delivery system into position. The imaging, navigation, and movement are all merged.

In another aspect of the disclosure, a method and device are provided that involve imaging the native root using an interoperative technique, then introducing a device that is easily visualized in a chosen imaging modality. The type of balloon used (e.g., flow-through or non-flow-through) will determine whether the cardiac motion will then need to be reduced. The balloon is then inflated and the aortic root is imaged so that the best size can be chosen that does not allow migration or force the leaflets to block the coronaries.

BRIEF DESCRIPTION OF THE DRAWINGS

The present disclosure will be further explained with reference to the appended Figures, wherein like structure is referred to by like numerals throughout the several views, and wherein:

FIG. 15 is a broken perspective view, partly schematic, illustrating a high intensity focused ultrasound stimulation or ablation assembly for use in the methods of the present invention.

FIG. 16 is a broken bottom view of an ultrasound emitting member of a focused ultrasound ablation device of the high intensity focused ultrasound stimulation or ablation assembly.

FIG. 17 is a broken side view, partly in section, of the ultrasound emitting member and depicting focusing of ultrasound energy in the skin to form an ablated tissue area containing unablated skin tissue and a plurality of lesions at which the skin tissue is ablated.

FIG. 18 is a broken top view illustrating the surface or cross-sectional configuration of the ablated tissue area of FIG. 17.

DETAILED DESCRIPTION

Figure 1:
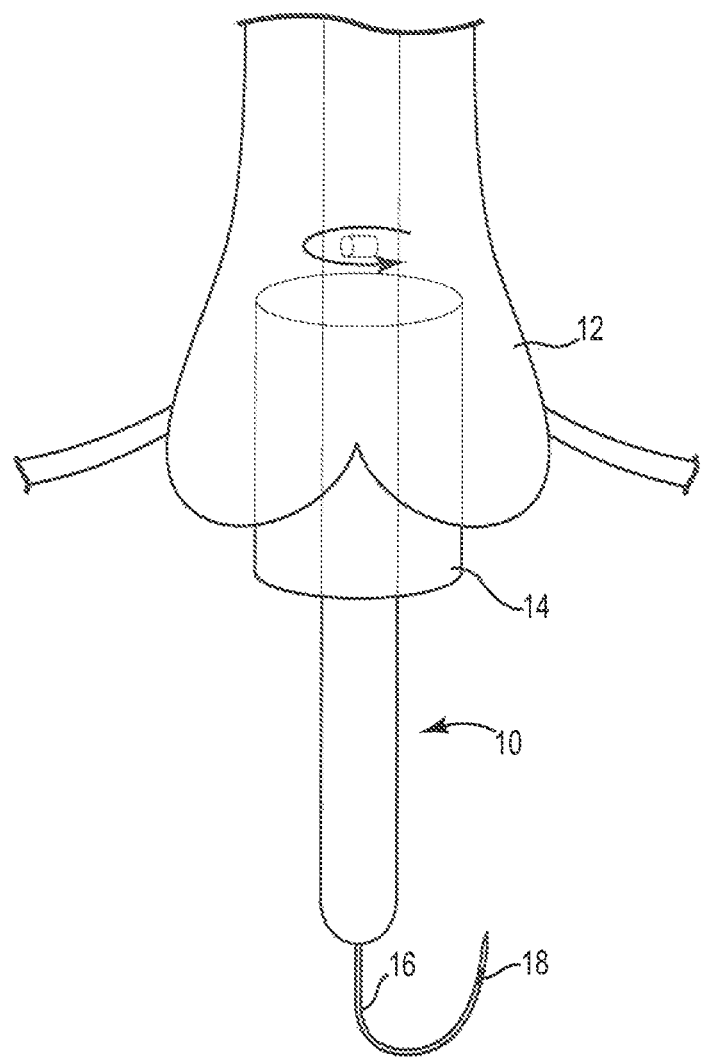
FIG. 1 is a schematic front view of one embodiment of a heart valve delivery system of the disclosure, including at least one ferromagnetic element used for valve placement.

As set out above, the navigation systems of the present disclosure are particularly directed to percutaneous replacement and repair of cardiac valves, which can be performed using a number of different delivery systems. One exemplary delivery system and its use may correspond to that described in the above-cited Tower, et al. applications, where the stented valve can be expanded against a failed native or prosthetic valve. The delivery system can be advanced to the desired valve implant site using a guidewire, after which the sheath is moved proximally, exposing the balloon mounted on an inner catheter. The balloon is expanded, which thereby expands the stented valve until it reaches a desired outer diameter where it contacts the wall of a heart vessel. The balloon is then deflated and the delivery system is withdrawn proximally. In order to locate the valve and delivery systems during the surgical procedure, one or a combination of the methods, devices, and systems of the disclosure described herein may be used.

Notably, although the term "replacement" normally signifies removal of a diseased valve and implantation of a new valve, in accordance with the disclosure, a new valve may also be implanted directly over top of or adjacent to a diseased native valve, which may also generically be referred to as "replacement" or may instead be referred to as "implantation". Both types of procedures are contemplated for use with the present disclosure. In many cases, an implantation procedure can be the same as a replacement procedure without the removal of the diseased valve.

Certain embodiments of the disclosure described herein may only be used for placement of particular valves (e.g., aortic valves); however, some embodiments of the disclosure may be useful for valve placements in more than one area of the heart (e.g., mitral valves, pulmonic valves), with the methods requiring different navigation of the device to these areas of the heart. In any of the methods of the disclosure, it is desirable to avoid placing the valve prosthesis in a position that blocks the coronaries during the surgical process.

The location for valve implantation or repair can be determined by various imaging modalities such as ultrasound imaging, CT, MRI, PET, fluoroscopy, etc. The coordinates for the desired location for valve implantation or repair from any of these imaging modalities can be determined. Two or three-dimensional imaging may be performed as well as phased or annular array imaging may be performed. For example, two or three-dimensional echocardiography, such as transesophageal echocardiography, or ultrasound imaging, such as transthoracic ultrasound imaging may be employed as described in U.S. Patent Application Publication No. 2005/0080469, the disclosure of which is incorporated by reference in its entirety. In one embodiment of the disclosure, an imaging device may be used to illuminate a valve implantation site, a valve repair site and/or surgical site.

In one embodiment of the disclosure, an ultrasound imaging transducer assembly may be used to provide a real-time or multiplexed echo feedback on the progress of the valve implantation or repair. In one embodiment of the disclosure, the changes in mechanical properties of tissue may be observed in eco imaging. In addition, an ultrasound transducer may sense reflections from the targeted tissue such as backscatter echo and spatial compound imaging, etc. to provide one or more properties of the tissue imaged.

In addition, with the methods of the disclosure, it is often desirable to use a sizing balloon prior to valve placement to determine the proper size of the valve that will be implanted. One example of a sizing technique is to use an expandable and retractable sizing device made out of a material such as Nitinol. Such a sizing device can be navigated to the implantation site, such as by using an MRI compatible device, and then an image can be taken of the sizing device in its compressed or retracted condition. The device can then be expanded until it is in contact with the vessel at the implantation site and another image can be taken of the device in its expanded condition. These images of the sizing device in its compressed condition and expanded condition are then compared with each other and with the sizes of the available valves to determine the optimum valve for implantation. Additionally or alternatively, the pressure increase of a sizing device (e.g., an expandable balloon-type device) can be monitored and recorded during its expansion, and the data obtained can be compared to a pre-measured pressure increase of a similar device. That is, the information obtained from the pressure increase in the sizing device will correspond with a certain external size of the device, which in turn will correspond to a valve of a certain size. It is further contemplated that the implantation device can release dye into the implantation area while checking the pressures to determine if the device is blocking any of the coronaries.

In some embodiments of the disclosure, electromagnetic navigation can be performed with 4D ultrasound, as opposed to using fluoroscopy, CT, or MRI, for example. For one particular example, the 4D ultrasound can be used for intraoperative navigation instead of using fluoroscopy in order to obtain better resolution of the heart.

Referring now to the Figures, wherein the components are labeled with like numerals throughout the several Figures, and initially to FIG. 1, a delivery system 10 is illustrated, with a prosthetic valve 14 mounted thereon and being inserted into an aorta 12 of a patient. Delivery system 10 includes a guide wire 16 and at least one sensor 18, e.g., a ferromagnetic element, that establishes an electric field for the system 10 and can be used to give rotation to the valve. Although it is possible that only one ferromagnetic element 18 is provided, multiple ferromagnetic elements may be provided at spaced-apart locations along a portion of the length of the delivery device to provide additional data regarding navigation of the system 10. In any case, intraoperative imaging or preoperative images can be used to define alignment of annuloplasty devices, for example. The use of these ferromagnetic elements can precisely locate points within the heart using an external, 3-dimensional frame of reference.

Each element 18 of a particular delivery system 10 may be the same or different from other ferromagnetic elements 18 in that same system. When the elements are different from each other, the ferromagnetic elements may be distinguishable to provide the navigation process with an additional assurance of accuracy. In particular, each sensor 18 may have a variety of different shapes and forms, such as a coil that is wound around the delivery system with a predetermined number of wrappings, a clamp or collar that extends completely or partially around the delivery system at certain locations, or any other configuration that can be securely attached to the delivery system. Further, the sensor elements 18, e.g., ferromagnetic elements, should be sufficiently large that they are visible using the imaging devices of the system, but should not be so large that they interfere with the valve replacement process.

Figure 2:
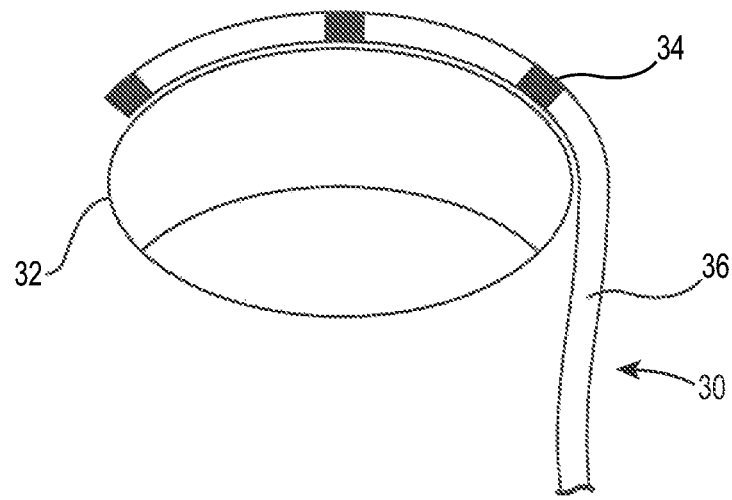
FIG. 2 is a schematic front view of a portion of a delivery system for an annuloplasty device, which is positioned adjacent to a valve annulus.

FIG. 2 is a schematic view of a delivery system 30 positioned relative to an annulus 32 of a patient's heart. Delivery system 30 includes multiple sensors 34, e.g., ferromagnetic elements, spaced from each other along the length of an elongated body 36. The number, size, spacing, and type of sensor elements 34 may be selected to determine certain characteristics of the annulus of the patient. In any case, interoperative imaging or preoperative images can be used to define the alignment of a valve repair device, e.g., an annuloplasty device, that is to be implanted.

The delivery systems of FIGS. 1 and 2 can be used with a system that moves the sensor objects, e.g., ferromagnetic objects, on the devices via an externally generated magnetic field. In one specific example, preoperative and intraoperative imaging can help guide the device or delivery system to an annulus (e.g., a mitral annulus) using a system that involves the use of an external magnetic field which drives ferromagnetic objects placed on a catheter into their desired position. The information provided by the imaging, navigation, and movement are advantageously merged together for use by the physician or surgeon.

Figure 3:
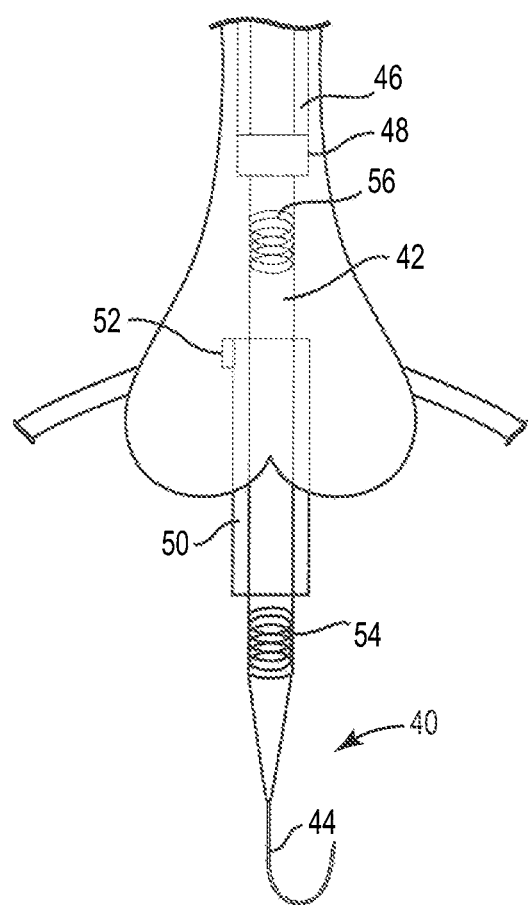
FIG. 3 is a schematic front view of another embodiment of a heart valve delivery system of the disclosure.

FIG. 3 illustrates a delivery system 40, which includes a catheter 42, a guide wire 44, a sheath 46, and one or more sensor markers 48 on the sheath 46. The sensor marker or markers 48 on the sheath 46 allow for precise exposure of the stent or an associated balloon during a stent delivery process. That is, the location of each sensor marker 48 can be detected and therefore can allow for precise movement of the sheath 46. The delivery system 40 further includes a prosthetic valve 50 that has at least one sensor marker 52, e.g., a radiopaque marker, to allow for rotational orientation of the valve 50. This delivery system 40 is used for pre-screening or pre-imaging of the anatomy of a patient to thereby provide a roadmap of the native anatomy. The delivery system 40 can further be used to image with a balloon or sizer that is deployed into the root at various pressures, which will allow for a measurement of compliance. The system also includes a first sensor navigation coil 54 positioned adjacent to one end of the valve 50, and a second sensor navigation coil 56 positioned adjacent to the opposite end of the valve 50.

Figure 4:
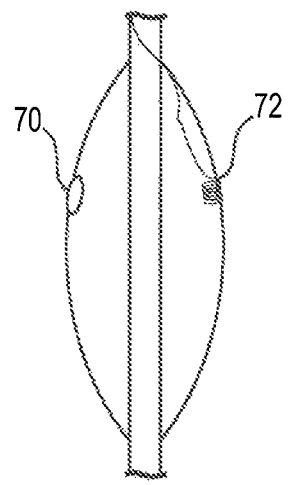
FIG. 4 is a schematic front view of a portion of another embodiment of a heart valve delivery system of the disclosure.

FIG. 4 further illustrates a portion of a delivery system that includes a sensor marker 70 that may be a radiopaque material, gadolinium, dysprosium oxide, or another material that makes it visible in certain imaging modalities. For example, gadolinium (Gd) markers can be used for MRI procedures. The system further includes at least one sensor electromagnetic receiver coil or electrode 72. Sensor marker 70 is positioned on a portion of the system that may be referred to as the passive portion or segment of the system, and the sensor electromagnetic coil or electrode 72 is positioned on a portion of the system that may be referred to as the active portion or segment of the system. This system can be used to capture preoperative images, register the images to the intraoperative patient anatomy, and navigate within the anatomy using electromagnetic or electropotential methods or passively using intraoperative MRI. Each sensor electromagnetic coil or electrode 72 may be placed at a predetermined location on the catheter delivery system and on its associated implantable valve. The predetermined location or locations can be chosen for functional components to ensure proper positioning. For example, a sensor element, e.g., an electromagnetic coil, can be placed at the tip of a catheter so that it is possible to continuously track and visualize the catheter tip in real time without the continuous use of fluoroscopy.

In another alternative, one or more electromagnetic coils can be placed at the end and/or the middle and/or other intermediate location(s) of an inflatable balloon to track the location of the balloon relative to the annulus of the target valve. In this way, the location of the balloon can be determined so that the catheter can be maneuvered to accurately position the balloon at a predetermined location for its inflation and for valve deployment. In a similar manner, one or more sensor electromagnetic coils can additionally or alternatively be placed on a valve in order to enable an operator to track and visualize the valve on the delivery device and to accurately position the valve in a predetermined location. One advantage that is provided by the use of these sensor electromagnetic coils is that the coils provide an operator with the ability to track the devices (e.g., valves) in a different visualization modality into which relatively detailed anatomical information can be incorporated. For example, the tracking or positioning of the sensor electromagnetic coils can be superimposed over a 3-dimensional preoperative image of the patient's anatomy, which provides more detailed information of the cardiac tissue without contrast use and without repeated exposure to x-rays or other radiation.

Figure 5:
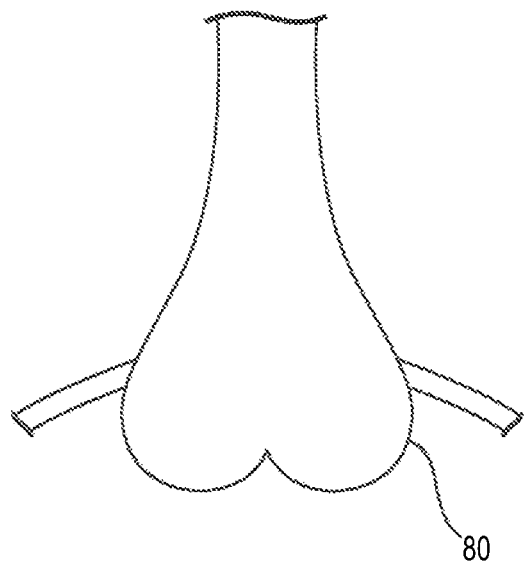
FIGS. 5 and 6 are schematic front views of an aortic root of a heart, with FIG. 6 illustrating a delivery system positioned relative to the aortic root.
Figure 6:
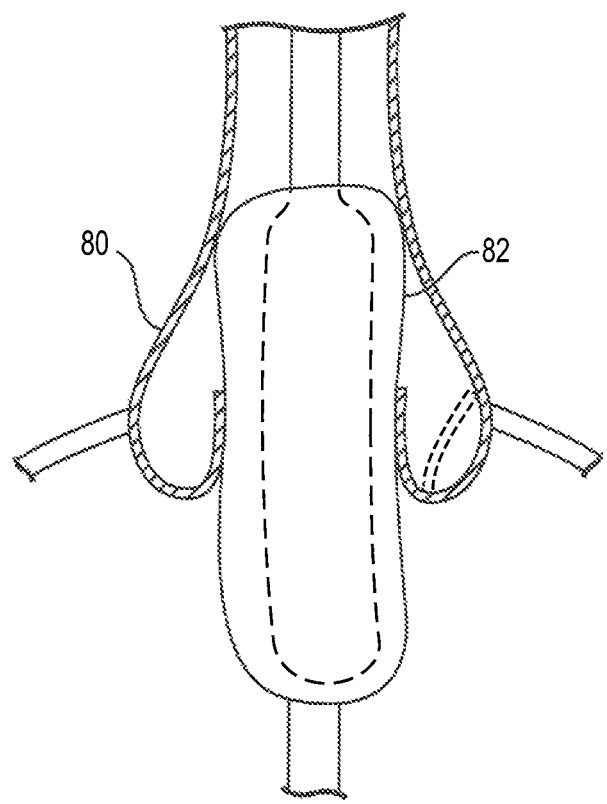

FIGS. 5 and 6 illustrate a method and device for delivering a heart valve in accordance with the disclosure. In general, the native root 80 is initially imaged using an intraoperative technique, such as fluoroscopy, 4D echo, interventional MRI, and the like. This image becomes the baseline or "roadmap" that is used for the remainder of the processes. A balloon 82 or stent may then be deployed or a stent can be used to size the aortic valve at various pressures or stages. The chosen balloon or stent should be easily visualized in the chosen imaging modality (e.g., if interventional MRI is used, iron or gadolinium can be used). That is, the materials chosen for the balloon or stent should make the device conspicuous with the imaging technique that is used.

The blood flow may then optionally be reduced by controlled intermittent asystole, high rate pacing, or other technique(s) used for slowing cardiac motion or stopping the heart for extended periods of time. The balloon 82 or stent may alternatively be designed to allow blood to flow or pass through it, in which case the blood flow would not necessarily need to be reduced. A non-compliant balloon can be inflated to various pressures and/or sizes and the aortic root can be imaged while looking at the leaflet anatomy. The balloon can then be chosen to be the best size that will not migrate but that also does not force the leaflets to block the coronaries. Alternatively or additionally, a compliant balloon, can be used to determine the compliance of the aortic root. If stents are used, they are preferably recapturable and the leaflets preferably function when the device is deployed but not released. In any case, the deployment diameter or force chosen must prevent the valve leaflets from covering the coronary ostia.

In accordance with the disclosure, additional aspects of methods and devices for balloon sizing and valvuloplasty using a valvuloplasty/sizer balloon include a number of steps, some of which are optional. In one embodiment, a valvuloplasty/sizer balloon is selected, where multiple balloons can be provided in a number of different sizes and/or where each balloon can be provided as a single balloon (compliant or non-compliant), or may comprise multiple balloons that are coaxial or placed serially in a linear arrangement on the same catheter. The balloon can include features that allow for at least some blood flow, such as a certain level of porosity and/or at least one central hole, for example. The chosen balloon or balloons can then be inflated to a first pressure that correlates with a known radial force that will typically be required by a certain transcatheter valve stent that will subsequently be implanted.

Once the balloon or balloons are inflated to this first pressure, a number of measurements can be performed, which can be selected for a particular application from a number of measurement options. One such measurement is to measure the diameter or other dimensions of the balloon at various anatomical locations (e.g., annulus, sinotubular junction, ascending aorta, sinus region, and the like) using a balloon silhouette or radiopaque fluid within the balloon. The circularity of diameters at one or more anatomical locations can then be measured. The orifice area can then be calculated. The clearance between the native leaflets and the coronary arteries can then be measured with the balloon or balloons inflated to simulate the dimensions of the transcatheter valve stent when it is deployed. The balloon can optionally include integral markings to facilitate making this measurement. The balloon could also have indicia or other detectable features that indicate particular structural features that allow a clinician to determine a desirable stent height to avoid the coronary ostia, to provide stable seating of the valve in its space, and the like. The balloon catheter can incorporate means (e.g., transducer or calibrated joint or feature) to assess the dislodgement or migration force of the transcatheter valve stent that will be deployed.

Next, the parameters of the system can be evaluated. First, the calcific locations of the native valve can be identified, and a determination can be performed of the mobility of the calcium under balloon inflation. A verification can be made of the coronary clearance and patency with native leaflets pushed out by the balloon, which thereby simulates the transcatheter valve stent. The resulting effect on the adjacent anatomy (e.g., the mitral valve orifice) can also be evaluated, along with the effect on the heart rhythm (e.g., heart block, fibrillation, and the like).

After the chosen measurement and evaluation steps have been completed, these results can be compared against target values or guidelines to determine whether an acceptable result has been achieved. If acceptable results have not been achieved, some or all of the previous steps can be performed at one or more additional pressures that are different than the first pressure, where each new pressure that is used corresponds to a different radial force, until an acceptable result is achieved. When an acceptable result is achieved, then a balloon valvuloplasty can be performed, where the optimum stent radial force, stent height, and stent profile can be selected based on the measurements and evaluation parameters discussed above. However, if an acceptable result cannot be achieved even after using different pressures, it is contemplated that the procedure be abandoned in that the valve is not suitable for implant at this location for at least one reason (e.g., that the coronaries are occluded at all pressures, that the valve will migrate at all pressures, that arrhythmia or heart block will occur at all pressures, that the diameter and/or circularity are outside the feasibility range for the device, and/or the like). It is noted that the measurements may optionally be repeated after the balloon valvuloplasty is performed.

In the methods of imaging of the disclosure, a number of materials can be used as contrast medium for the components of the systems. These materials can provide contrasting markers that are combined for improved imaging results. For one example, when magnetic resonance imaging (MRI) techniques are used, iron can be used for imaging. Alternatively, dysprosium oxide can be characterized as the negative material and be illustrated as a black area on a display screen, and gadolinium can be characterized as the positive material and be illustrated as a white area. For another example, when echocardiographic techniques are used, gas can be shown as a black area on a display screen, and microspheres or nonocoatings may be shown as a white area. For yet another example, when computed tomography (CT) techniques are used, markers can be provided with different materials that are illustrated as either black or white areas, such as can be provided by platinum, tantalum, $BaSO_4$, and the like.

Figure 7:
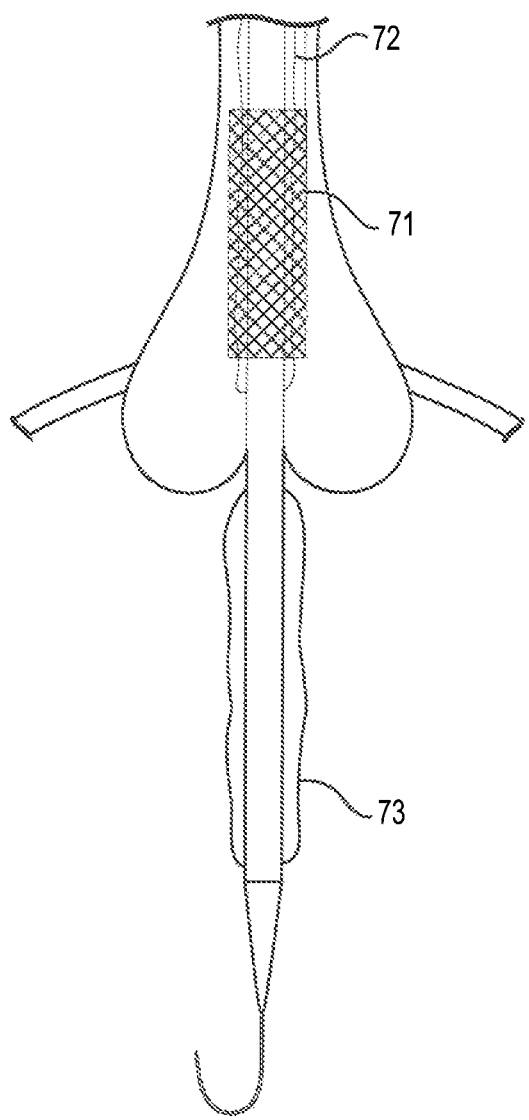
FIG. 7 is a schematic front view of another embodiment of a heart valve delivery system of the disclosure.

FIG. 7 illustrates a system that provides the dual function of deploying a stent 71 with an inflatable and expandable balloon 72, while also providing a dilation balloon or leaflet resection tool 73. The dilation balloon can be used for dilation, measurement, and/or excising of the native valve.

Figure 8:
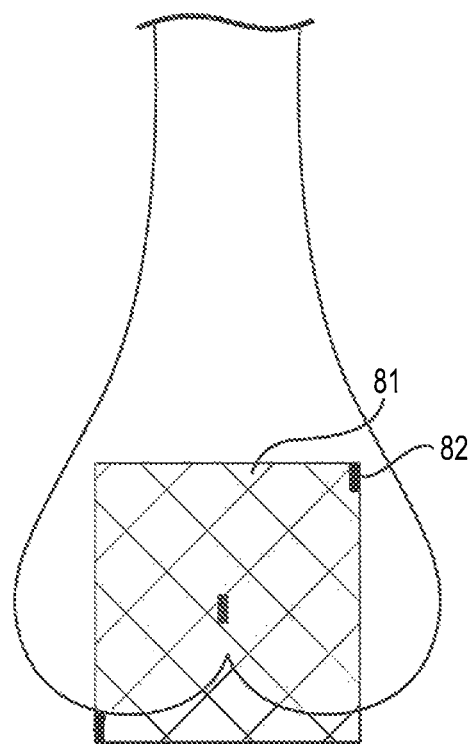
FIG. 8 is a schematic front view of another embodiment of a delivery system of the disclosure.

FIG. 8 shows a stent 81 positioned relative to an aortic valve, where the stent includes multiple sensor markers 82 spaced from each other. These sensor markers provide visualization so that post-operative follow-up can be accomplished more easily. In particular, having specific, easily identifiable markers facilitates being able to repeatably follow the stent over time and to measure deformation of the stent, as well as to track any fractures that may occur relative to the identifiable markers. The markers can also provide guidance for additional valves or stents that may need to be positioned relative to the stent. For one example, a second stent or valve can have the same or similar markers as the original stent or valve so that a physician can align the markers of both valves or stents in order to deploy the new valve in the desired position relative to the old stent or valve. In another example, the second stent or valve can have different markers than the original stent or valve, such that a particular relationship or positioning of the new and old stents or valves can be achieved by positioning the markers in a certain arrangement relative to each other.

Figure 9:
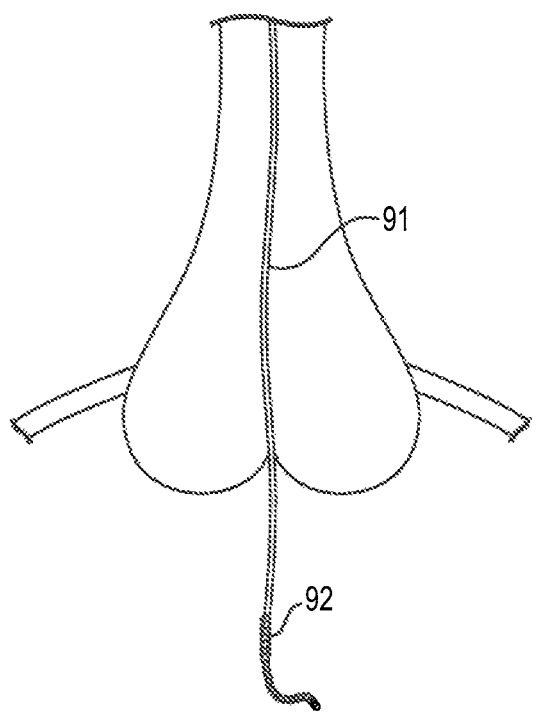
FIG. 9 is a schematic front view of a guide wire of a heart valve delivery system of the disclosure.

FIG. 9 is an illustration of an embodiment of an imaging technique in which a guide wire 91 includes one or more sensors 92, for example, an echogenic coating, a RF receiver coil, a gadolinium marker, an electrode, or the like. This element or portion of the guide wire allows precise passage of the wire through a stenotic aortic valve using an intraoperative imaging mode. Using the techniques described herein to visualize or guide a component or device with these markers, the guidewire can be guided across the stenotic orifice, which can be challenging if it is heavily calcified. This can be accomplished more easily if the guidewire is steerable.

Figure 10:
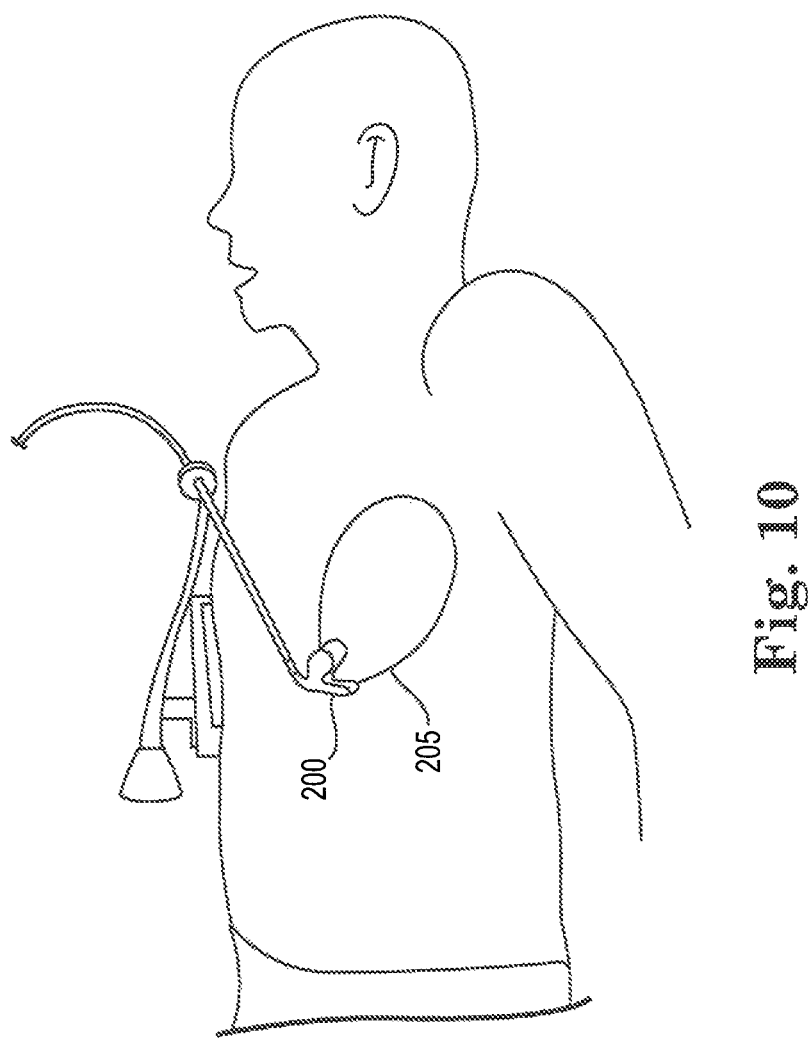
FIG. 10 is an illustration of a tissue-engaging device of the disclosure.

FIG. 10 is an illustration of a tissue-engaging device 200 being used in a closed chest, non-sternotomy procedure to position the heart 205 into a non-physiological orientation. Positioning the heart in a non-physiological orientation can provide access to areas of the heart that normally would not be available to one or more devices, for example, through a thoracotomy or port, through the patient's esophagus or trachea, or positioned outside the chest.

Figure 11:
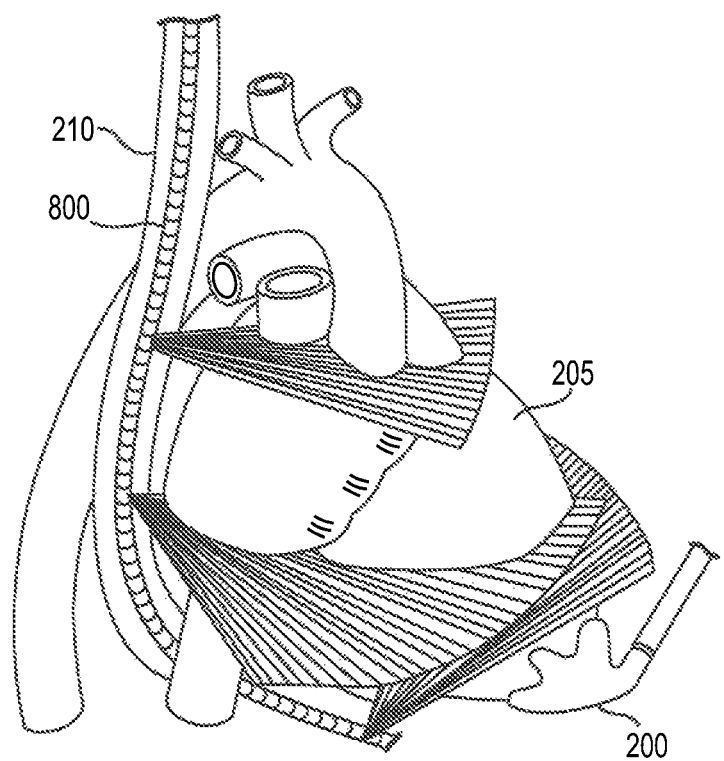
FIG. 11 is an illustration of an imaging device of the disclosure.

In one embodiment of the disclosure, an imaging device 800 may be used to image tissue such as heart tissue as shown in FIG. 11. The imaging device may be appropriately sized to allow its placement within the esophagus of the patient. Alternatively, the imaging device may be appropriately sized to allow its placement within the trachea and/or bronchi of the lungs of the patient. Alternatively, one or more imaging devices may be positioned through one or more other body cavity openings of the patient and/or positioned on the skin of the patient. For example, one or more imaging devices may be positioned through the mouth, the nose, the anus, the urethra and/or the vagina. In one embodiment of the disclosure, one or more imaging devises may be placed through a port, a stab wound, or an incision. In one embodiment of the disclosure, a valve replacement device or a valve repair device may include one or more imaging capabilities. For example, ultrasound imaging capabilities may be incorporated into a valve replacement device or valve repair device so that a single device could be used to both image and repair valve tissue or image and implant a valve bioprosthesis.

In one embodiment of the disclosure, once one or more imaging devices are placed in the desired position, cardiac tissue is then imaged and the location of valve tissue to be treated is determined. To image cardiac tissue not positioned within the focusing range of an imaging device, a tissue-engaging device 200 may be used to move and position the tissue of interest within the focusing range of the imaging device. The tissue-engaging device 200 may be used to position tissue prior to an imaging procedure, during an imaging procedure and/or following an imaging procedure. In addition to cardiac tissue, other tissue types and/or organs may be positioned and imaged by one or more positioning and imaging devices. In one embodiment of the present disclosure, the positioning or tissue-engaging device may comprise one or more imaging capabilities, e.g., ultrasound imaging.

In one embodiment of the disclosure, a tissue-engaging device may include one or more ultrasound imaging elements. The tissue-engaging device comprising one or more ultrasound imaging elements may be used to move and position tissue. A tissue-engaging device may be used to position tissue prior to a valve procedure, during a valve procedure and/or following a valve procedure, for example, a valve implantation or repair procedure. In addition to cardiac tissue, other tissue types and/or organs may be imaged by one or more ultrasound imaging elements of the device. The distal end of the tissue-engaging device may be positioned within a patient through an incision, a stab wound, a port, a sternotomy and/or a thoracotomy. An endoscope may be used to help position the tissue-engaging device.

In one embodiment of the disclosure, an imaging device or system may comprise one or more switches to facilitate its regulation by a physician or surgeon. One example of such a switch is a foot pedal. The switch may also be, for example, a hand switch, or a voice-activated switch comprising voice-recognition technologies. The switch may be incorporated in or on one of the surgeon's instruments or any other location easily and quickly accessed by the surgeon or medical practitioner. In one embodiment, a switch may be physically wired to the imaging device or it may be a remote control switch.

In one embodiment of the disclosure, an imaging device may be based on one or more imaging modalities such as ultrasound imaging, CT, MRI, PET, fluoroscopy, echocardiography, etc. An imaging device may have two and/or three-dimensional imaging capabilities as well as phased and/or annular array imaging capabilities. For example, two or three-dimensional echocardiography, such as transesophageal echocardiography (TEE), or ultrasound imaging, such as transthoracic ultrasound imaging may be possible with use of an imaging device.

The imaging device may comprise one or more light sources and/or illuminating materials, e.g., glow-in-the-dark materials. For example, one or more portions of a tissue-engaging device and/or one or more portions of a valve replacement or repair delivery system may comprise one or more glow-in-the-dark materials. The imaging device may be based on fluorescence technologies. The imaging device may comprise fiber optic technologies; for example a fiber optic conduit may deliver light from a remote light source to an area adjacent a treatment site.

An imaging device may comprise a light pipe, for example, to illuminate the tissue-engaging device and/or a valve replacement or repair delivery device and/or the surgical field adjacent. A transparent, semi-transparent or translucent tissue-engaging head may be illuminated merely by placement of the end of a light pipe or other light source adjacent a portion of the tissue-engaging device. A transparent, semi-transparent or translucent portion of a valve replacement or repair device may be illuminated merely by placement of the end of a light pipe or other light source adjacent a transparent, semi-transparent or translucent portion of a valve replacement or repair delivery device or system.

An imaging device may include a visual display or monitor, such as, for example, a LCD or CRT monitor, to display various amounts and types of information. By software control, the user may choose to display the information in a number of ways. The imaging device may be powered by AC current, DC current, or it may be battery powered either by a disposable or re-chargeable battery. The imaging device may provide UV, IR and/or visible light. The imaging device may include a laser. The imaging device may be incorporated into tissue-engaging device and/or a valve replacement or repair device or system or it may be incorporated into a separate device. A separate imaging device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. A separate imaging device may be positioned through one or more body cavity openings of the patient and/or positioned outside the patient, e.g., near the patient or on the skin of the patient. One or more imaging devices may be positioned in the esophagus, the trachea and/or the bronchi of the lungs.

In one embodiment of the disclosure, the beating of a patient's heart may be controlled before a cardiac valve procedure, during a cardiac valve procedure, or following a cardiac valve procedure, e.g., a valve replacement procedure or a valve repair procedure. In one embodiment of the disclosure, a nerve stimulator device comprising one or more nerve stimulation electrodes may be used to stimulate the patient's vagal nerve to slow or stop the patient's heart during a valve replacement or valve repair procedure. The patient may be given one or more drugs to help stop the beating of the heart and/or to prevent "escape" beats. Following vagal stimulation, the heart may be allowed to return to its usual cardiac rhythm. Alternatively, the heart may be paced, thereby maintaining a normal cardiac output or to increase cardiac output. Vagal stimulation, alone or in combination with electrical pacing and/or drugs, may be used selectively and intermittently to allow a surgeon to perform a valve replacement or valve repair procedure on a temporarily stopped heart. For example, stimulation of the vagus nerve in order to temporarily and intermittently slow or stop the heart is described in U.S. Pat. Nos. 6,006,134, 6,449,507, 6,532,388, 6,735,471, 6,718,208, 6,228,987, 6,266,564, 6,487,446 and U.S. patent application Ser. No. 09/670,370 filed Sep. 26, 2000, Ser. No. 09/669,961 filed Sep. 26, 2000, Ser. No. 09/670,440 filed Sep. 26, 2000. These patents and patent applications are incorporated herein by reference in their entireties.

Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present disclosure may include various electrodes, catheters and electrode catheters suitable for vagal nerve stimulation to temporarily stop or slow the beating heart alone or in combination with other heart rate inhibiting agents.

Nerve stimulation electrodes may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon, which may be inflated with air or liquid to press the electrodes firmly against the vessel wall. Similar techniques may be performed by insertion of a catheter-type device into the trachea or esophagus. Additionally, tracheal devices, e.g., tracheal tubes, tracheal imaging devices, and/ or esophageal devices, e.g., esophageal tubes, esophageal imaging devices, comprising electrodes may be used.

Nerve stimulation electrodes may be oriented in any fashion along a catheter device, including longitudinally or transversely. Various imaging techniques or modalities, as discussed earlier, such as ultrasound, fluoroscopy and echocardiography may be used to facilitate positioning of the electrodes. If desired or necessary, avoidance of obstruction of air flow or blood flow may be achieved with notched catheter designs or with catheters, which incorporate one or more tunnels or passageways.

In one embodiment of the disclosure, the location of the electrodes is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Figure 12:
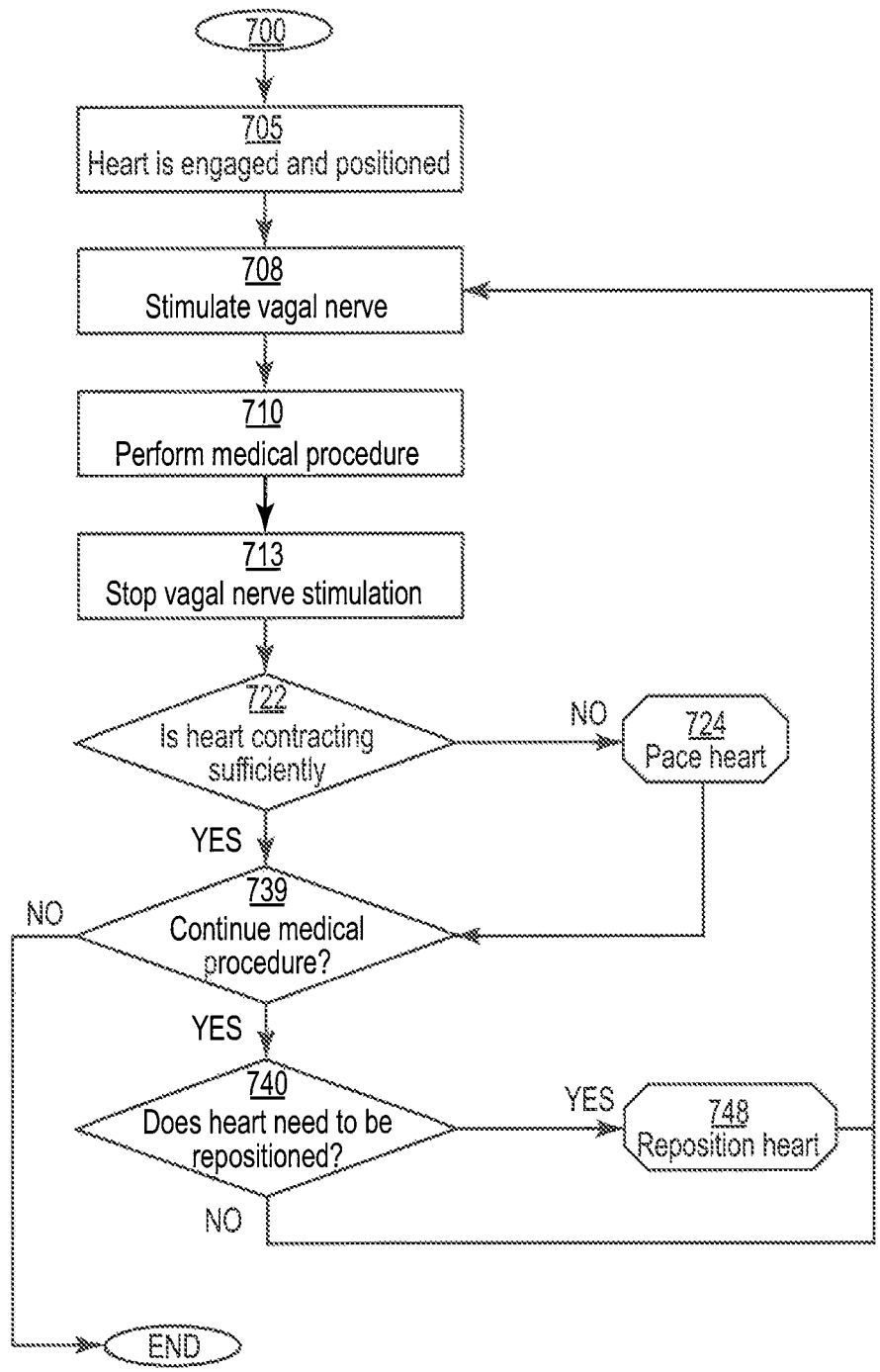
FIG. 12 is a flow diagram of one embodiment of the disclosure.

FIG. 12 shows a flow diagram of one embodiment of the present disclosure. The patient is prepared for a medical procedure at 700. Once the patient is prepared, the heart is engaged and positioned using tissue-engaging device 200 (Block 705). Once the heart is positioned in a desired orientation, e.g., a non-physiological orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. Drugs may be administered without nerve stimulation. The types of drugs administered may produce reversible asystole of a heart while maintaining the ability of the heart to be electrically paced. Other drugs may be administered for a variety of functions and purposes. Drugs may be administered at the beginning of the procedure, intermittently during the procedure, continuously during the procedure or following the procedure. Examples of one or more drugs that may be administered include a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

Typically, vagal-nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure, such as imaging and/or valve replacement or valve repair, is begun (Block 710). In one embodiment of the disclosure, one or more imaging devices may be positioned, e.g., outside a patient or within a patient, for example, within the trachea, bronchi of the lungs and/or esophagus of the patient, and an imaging modality is emitted, for example, ultrasound energy is emitted, from the one or more imaging devices and imaging energy is focused within tissue, e.g., cardiac tissue such as cardiac valve tissue. Following a brief interval of nerve stimulation while the valve replacement or valve repair procedure is performed, nerve stimulation is ceased (Block 713) and the heart is allowed to contract.

In one embodiment of the disclosure, the heart may be free to beat on its own or a cardiac stimulator device or pacemaker comprising one or more cardiac stimulation electrodes may be used to cause the heart to contract (Blocks 722 and 724). Cardiac stimulation electrodes used to stimulate the heart may be, for example, non-invasive, e.g., clips, or invasive, e.g., needles or probes. Cardiac electrodes may be positioned through a thoracotomy, sternotomy, endoscopically through a percutaneous port, through a stab wound or puncture, through a small incision in the chest, placed on the chest or in combinations thereof. The present disclosure may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes. In one embodiment of the disclosure, one or more cardiac electrodes, e.g., stimulation and/or monitoring electrodes, may be positioned on a tissue-engaging device. In one embodiment of the disclosure, a cardiac stimulator device may be used to stimulate the heart to beat rapidly to the point cardiac output is minimized or significantly decreased from a normal cardiac output. A valve replacement procedure or valve repair procedure may be performed during rapid pacing of the heart. In one embodiment of the disclosure, the heart may be stimulated to beat so fast it quivers and cardiac output essentially falls to zero during which a valve replacement procedure or valve repair procedure may be performed.

If the valve replacement or valve repair procedure needs to continue or a new valve replacement or repair procedure is to be performed, the heart again may be slowed or stopped via vagal nerve stimulation. In addition, the heart may be repositioned if necessary or desired at Block 748.

In one embodiment of the present disclosure, a probe device sized and shaped to fit within the trachea, bronchi and/or esophagus of the patient may comprise one or more nerve stimulation electrodes, members or elements and one or more ultrasound members or elements. The probe device may be positioned within the trachea, bronchi and/or esophagus of the patient. The nerve stimulation electrodes may be used to stimulate one or more nerves of the patient, e.g., a vagal nerve, as disclosed earlier, while the probe device is positioned within the trachea, bronchi and/or esophagus of the patient. A valve replacement or valve repair delivery system may be used, as disclosed earlier, while the probe device is positioned within the trachea, bronchi and/or esophagus of the patient. The nerve stimulation electrodes may be coupled to a nerve stimulator, e.g., used to stimulate the patient's vagal nerve to slow or stop the patient's heart during a valve replacement or valve repair procedure.

In one embodiment of the disclosure, a valve replacement or valve repair device or system may include a display and/or other means of indicating the status of various components of the device to the surgeon such as a numerical display, gauges, a monitor display or audio feedback. The valve replacement or valve repair device or system may also include one or more visual and/or audible signals used to prepare a surgeon for the start or stop of the valve replacement or valve repair procedure. A controller may synchronize deliver of a bioprosthetic valve between heart beats to reduce inadvertent tissue damage. A controller may be slaved to a nerve stimulator and/or a cardiac stimulator. Alternatively, a nerve stimulator and/or cardiac stimulator may be slaved to a controller. Alternatively, a controller may be capable of nerve stimulation and/or cardiac stimulation.

In one embodiment of the disclosure, electrodes may be used for cardiac pacing, defibrillation, cardioversion, sensing, stimulation, and/or mapping prior to, during, or following a valve replacement and/or valve repair procedure or procedures.

In one embodiment of the disclosure, a tissue-engaging device and/or a valve replacement or valve repair system or device may be attached to a flexible or rigid hose or tubing for supplying suction and/or fluids from a suitable suction source and/or fluid source to the target tissue surface through one or more suction and/or fluid elements, openings, orifices, and/or ports of the devices and/or systems. The hose or tubing may comprise one or more stopcocks and/or connectors such as luer connectors. Suction may be provided by the standard suction available in the operating room. Suction source may be coupled with a buffer flask and/or filter. Suction may be provided at a negative pressure of between 200-600 mm Hg with 400 mm Hg preferred. As used herein, the terms "vacuum" or "suction" refer to negative pressure relative to atmospheric or environmental air pressure.

Suction may be provided via one or more manual or electric pumps, syringes, suction or squeeze bulbs or other suction or vacuum producing means, devices or systems. Suction source may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to a tissue-engaging device and/or a valve replacement or valve repair system or device, thereby allowing the systems or devices to be easily manipulated by a physician or surgeon. Another method that would allow the physician or surgeon to easily manipulate the system or device includes incorporation of suction source into tissue-engaging device and/or a valve replacement or valve repair system. For example, a small battery operated vacuum pump or squeeze bulb may be incorporated.

In one embodiment of the disclosure, a suction source may be slaved to a tissue-engaging device, a fluid source, one or more sensors, an imaging device, a drug delivery device, a guidance device and/or a stimulation device. For example, a suction source may be designed to automatically stop suction when a controller sends a signal to stop suction. In one embodiment of the disclosure, a suction source may include a visual and/or audible signal used to alert a surgeon to any change in suction. For example, a beeping tone or flashing light may be used to alert the surgeon when suction is present. A suction source may be slaved to a robotic system or a robotic system may be slaved to a suction source. Suction may be used to secure, anchor or fix a tissue-engaging device and/or a valve replacement or valve repair system or device to an area of tissue. The area of tissue may comprise a beating heart or a stopped heart. Suction may be used to remove or aspirate fluids from the target tissue site. Fluids removed may include, for example, blood, saline, Ringer's solution, ionic fluids, contrast fluids, irrigating fluids and energy-conducting fluids. Steam, vapor, smoke, gases and chemicals may also be removed via suction.

In one embodiment of the disclosure, one or more fluid sources is provided for providing one or more fluids, for example, to a tissue-engaging device, a valve replacement delivery system or device, a valve repair delivery system or device, and/or the patient. A tissue-engaging device may be attached to a flexible or rigid hose or tubing for supplying fluids from fluid source to the target tissue through fluid elements, openings, orifices, or ports of device. A valve replacement or valve repair delivery system or device may be attached to a flexible or rigid hose or tubing for receiving fluids from fluid source and for supplying fluids, if desired, to the target tissue through fluid elements, openings, orifices, or ports of the system or device.

A fluid source of the present disclosure may be any suitable source of fluid. The fluid source may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. A fluid source may be powered by AC current, DC current, or it may be battery powered either by a disposable or re-chargeable battery. A fluid source may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to one or more devices, for example, a tissue-engaging device, an imaging device, a valve replacement device, or a valve repair device to deliver fluid and/or remove fluid, thereby allowing the device or system comprising a fluid source to be easily manipulated by a surgeon. Fluid reservoirs may include an IV bag or bottle, for example.

In one embodiment of the disclosure, one or more fluid sources may be incorporated into a tissue-engaging device and/or a valve replacement device and/or a valve repair device, thereby delivering fluid or removing fluid at the target tissue site. The fluid source may be slaved to a tissue-engaging device and/or a valve replacement device and/or a valve repair device, and/or a suction source, and/or a sensor and/or an imaging device. For example, the fluid source may be designed to automatically stop or start the delivery of fluid while a tissue-engaging device is engaged with tissue or while a valve replacement delivery device is delivering and positioning a valve or while a valve repair device is repairing a valve.

In one embodiment of the disclosure, one or more valve replacement delivery systems, valve repair systems, tissue-engaging devices, suction sources, fluid sources, sensors and/or imaging devices may be slaved to a robotic system or a robotic system may be slaved to one or more valve replacement delivery systems, valve repair systems, tissue-engaging devices, suction sources, fluid sources, sensors and/or imaging devices.

In one embodiment of the disclosure, the fluid source may comprise one or more switches, e.g., a surgeon-controlled switch. One or more switches may be incorporated in or on a fluid source or any other location easily and quickly accessed by the surgeon for regulation of fluid delivery by the surgeon. A switch may comprise, for example, a hand switch, a foot switch, or a voice-activated switch comprising voice-recognition technologies. A switch may be physically wired to a fluid source or it may be a remote control switch. The fluid source and/or system may include a visual and/or audible signal used to alert a surgeon to any change in the delivery of fluid. For example, a beeping tone or flashing light may be used to alert the surgeon that a change has occurred in the delivery of fluid.

In one embodiment of the disclosure, fluids delivered to a tissue-engaging device and/or a valve replacement device and/or a valve repair device and/or an imaging device and/or a sensor may include saline, e.g., normal, hypotonic or hypertonic saline, Ringer's solution, ionic, contrast, blood, and/or energy-conducting liquids. An ionic fluid may electrically couple an electrode to tissue thereby lowering the impedance at the target tissue site. An ionic irrigating fluid may create a larger effective electrode surface. An irrigating fluid may cool the surface of tissue. A hypotonic irrigating fluid may be used to electrically insulate a region of tissue. Fluids delivered according to one embodiment of the disclosure may include gases, adhesive agents and/or release agents.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with or without a fluid to the patient. Biological agents may be found in nature (naturally occurring) or may be chemically synthesized. Cells and cell components, e.g., mammalian and/or bacterial cells, may be delivered to the patient. A platelet gel or tissue adhesive may be delivered to the patient.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present disclosure, a drug delivery device may be used or incorporated into another device of the present disclosure. The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit.

One or more of the iontophoresis electrodes may also be used as, nerve stimulation electrodes or as cardiac stimulation electrodes.

A drug delivery device may be incorporated into a tissue-engaging device and/or a valve replacement device and/or a valve repair device and/or an imaging device, thereby delivering drugs at or adjacent the target tissue site or the drug delivery device may be placed or used at a location differing from the location of the target tissue site such as a cardiac valve site. In one embodiment of the disclosure, a drug delivery device may be placed in contact with the inside surface or the outside surface of a patient's heart.

In one embodiment of the disclosure, a drug delivery device may be slaved to a tissue-engaging device, a suction source, a fluid source, a sensor, an imaging device, a valve replacement device and/or a valve repair device. For example, a drug delivery device may be designed to automatically stop or start the delivery of drugs during tissue engagement of a tissue-engaging device, during valve replacement via a valve replacement device and/or a valve repair device. The drug delivery device may be slaved to a robotic system or a robotic system may be slaved to the drug delivery device.

The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device may include a visual and/or audible signal used to alert a surgeon to any change in the medical procedure, e.g., in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to one embodiment of this disclosure may include any naturally occurring or chemically synthesized (synthetic analogues) beta-adrenergic receptor blocking agents. Beta-adrenergic receptor blocking agents or .beta.-adrenergic blocking agents are also known as beta-blockers or .beta.-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this disclosure may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to one embodiment of this disclosure may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methyl sulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this disclosure may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to one embodiment of this disclosure may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to one embodiment of this disclosure may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III anti-arrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this disclosure may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this disclosure.

Beta-adrenergic stimulation or administration of calcium solutions may be used to reverse the effects of a calcium channel blocker such as verapamil. Agents that promote heart rate and/or contraction may be used in the present disclosure. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. In one embodiment, one catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage In one embodiment of the disclosure one or more sensors may be used to sense information regarding the patient or the procedure. A controller may store and/or process such information before, during and/or after a medical procedure, e.g., a valve replacement procedure and/or a valve repair procedure.

A controller may be used according to one embodiment of the present disclosure to control, for example, the energy supplied to one or more energy transfer elements, e.g., electrodes or transducers, of a tissue-engaging device, an imaging device, a valve replacement device and/or a valve repair device. The controller may also gather and process information from one or more sensors. The gathered information may be used to adjust energy levels and times. The controller may incorporate one or more switches to facilitate regulation of the various system components by the surgeon. One example of such a switch is a foot pedal. A switch may also be, for example, a hand switch, or a voice-activated switch comprising voice-recognition technologies. A switch may be physically wired to the controller or it may be a remote control switch. A switch may be incorporated in or on one of the surgeon's instruments, such as surgical site retractor, e.g., a sternal or rib retractor, a tissue-engaging device, a valve replacement device and/or valve repair device, or any other location easily and quickly accessed by the surgeon. The controller may include a display. The controller may also include other means of indicating the status of various components to the surgeon such as a numerical display, gauges, a monitor display or audio feedback.

The controller may incorporate a cardiac stimulator and/or cardiac monitor. For example, electrodes used to stimulate or monitor the heart may be incorporated into a tissue-engaging device, a valve replacement device, a valve repair device and/or an imaging device. The controller may incorporate a nerve stimulator and/or nerve monitor. For example, electrodes used to stimulate or monitor one or more nerves, e.g., a vagal nerve, may be incorporated into a tissue-engaging device, a valve replacement device, a valve repair device and/or an imaging device. The controller may comprise a surgeon-controlled switch for cardiac stimulation and/or monitoring, as discussed earlier. The controller may comprise a surgeon-controlled switch for nerve stimulation and/or monitoring, as discussed earlier. Cardiac stimulation may comprise cardiac pacing and/or cardiac defibrillation. The Controller, tissue-engaging device, a valve replacement device, a valve repair device and/or an imaging device may incorporate a cardiac mapping device for mapping the electrical signals of the heart.

A visual and/or audible signal used to alert a surgeon to the completion or resumption of energy delivery, suction, sensing, monitoring, stimulation and/or delivery of fluids, drugs and/or cells may be incorporated into a controller of the present disclosure. For example, a beeping tone or flashing light that increases in frequency as the energy delivered increases.

In one embodiment of the disclosure, a tissue-engaging device, a valve replacement device, a valve repair device and/or an imaging device may include one or more sensors. Sensor may be incorporated into a tissue-engaging device, a valve replacement device, a valve repair device and/or an imaging device or it may be incorporated into another separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

In one embodiment of the disclosure, a sensor may comprise one or more switches, e.g., a surgeon-controlled switch. One or more switches may be incorporated in or on a sensor device or any other location easily and quickly accessed by the surgeon for regulation of a sensor by a physician or a surgeon. A switch may be, for example, a hand switch, a foot switch, or a voice-activated switch comprising voice-recognition technologies. A switch may be physically wired to the sensor or it may be a remote control switch.

In one embodiment of the disclosure, a sensor may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed.

In one embodiment of the disclosure, a sensor may comprise one or more temperature-sensitive elements, such as a thermocouple, to allow a surgeon to monitor temperature changes of a patient's tissue. Alternatively, the sensor may sense and/or monitor voltage, amperage, wattage and/or impedance. For example, an ECG sensor may allow a surgeon to monitor the hemodynamics of a patient during a valve replacement or valve repair procedure. The heart may become hemodynamically compromised during positioning and while in a non-physiological position. Alternatively, the sensor may be any suitable blood gas sensor for measuring the concentration or saturation of a gas in the blood or tissues. For example, the sensor may be a sensor for measuring the concentration or saturation of oxygen or carbon dioxide in the blood or tissues. Alternatively, the sensor may be any suitable sensor for measuring blood pressure or flow, for example a Doppler ultrasound sensor system, or a sensor for measuring hematocrit (HCT) levels.

Alternatively, the sensor may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

In one embodiment of the disclosure, the sensor may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

A sensor may be used to detect naturally detectable properties representative of one or more characteristics, e.g., chemical, physical, mechanical, thermal, electrical or physiological, of a valve replacement system, a valve repair system, and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties may include, for example, pressure, tension, stretch, fluid flow, electrical, mechanical, chemical and/or thermal. For example, a sensor may be used to sense, monitor and/or control suction or vacuum delivered from a suction source. A sensor may be used to measure suction between a device and tissue. A sensor may be used to sense, monitor and/or control fluid delivered from a fluid source. A sensor may be used to sense, monitor and/or control energy delivered from a power supply via a controller.

In one embodiment of the disclosure, a sensor may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

In one embodiment of the disclosure, one or more sensors may be incorporated into a tissue-engaging device, a valve replacement device, a valve repair device and/or an imaging device or one or more sensors may be placed or used at a location differing from the location of a tissue-engaging device, a valve replacement device, a valve repair device and/or an imaging device. For example, a sensor may be placed in contact with the inside surface or outside surface of a patient's heart during a valve replacement procedure or valve repair procedure.

In one embodiment of the disclosure, a tissue-engaging device, a valve replacement device, a valve repair device, an imaging device, a suction source, a fluid source, a drug delivery device and/or a controller or processor may be slaved to one or more sensors. For example, a tissue-engaging device may be designed to automatically adjust suction if a sensor measures a predetermined sensor value, e.g., a particular suction value.

In one embodiment of the disclosure, the sensor may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

In one embodiment of the disclosure, one or more devices may be coupled to a controller, which may include one or more processors. For example, a processor may receive and preferably interpret a signal from one or more sensors. A processor may comprise software and/or hardware. A processor may comprise fuzzy logic. A suitable amplifier may amplify signals from one or more sensors before reaching a processor. The amplifier may be incorporated into a processor. Alternatively the amplifier may be incorporated into a sensor, a tissue-engaging device, a valve replacement device, a valve repair device, a suction source, a fluid source, a drug delivery device, and/or an imaging device. Alternatively, the amplifier may be a separate device. A processor may be a device separate from a sensor, a tissue-engaging device, a valve replacement device, a valve repair device, a suction source, a fluid source, a drug delivery device, and/or an imaging device. A processor may be incorporated into a sensor, a tissue-engaging device, a valve replacement device, a valve repair device, a suction source, a fluid source, a drug delivery device, and/or an imaging device. A processor may control the energy delivered from a power supply. For example, a signal of a first intensity from a sensor may indicate that the energy level from a power supply should be lowered; a signal of a different intensity may indicate that the power supply should be turned off. For example, a processor may be configured so that it may automatically raise or lower the suction delivered to a device comprising suction, the fluids delivered to a device comprising fluid delivery, the drugs delivered to a device comprising drug delivery, energy delivered to a device comprising energy delivery, e.g., from a power supply. Alternatively, for example, the control of the suction source, the fluid source, drug delivery source, the power supply based on output from a processor may be manual.

In one embodiment of the disclosure, a controller may include a visual display or monitor, such as, for example, a LCD or CRT monitor, to display various amounts and types of information. By software control, the user may choose to display the information in a number of ways. The monitor may show, for example, a currently sensed parameter, e.g., blood flow or blood-pressure or cardiac contractions. The monitor may also lock and display the maximum sensed value achieved. Sensed information may be displayed to the user in any suitable manner, such as for example, displaying a virtual representation of valve replacement device, a valve repair device, an imaging device and/or tissue-engaging device on the monitor. Alternatively, a monitor may display the voltage corresponding to the signal emitted from a sensor. This signal may correspond in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would, for example, turn off or adjust the power supply.

The display of a controller according to one embodiment of the disclosure may be located on a valve replacement device, a valve repair device, a power supply, a tissue-engaging device, a suction source, a fluid source, a sensor and/or an imaging device. An indicator, such as an LED light, may be permanently or removeably incorporated into a valve replacement device, a valve repair device, a power supply, a tissue-engaging device, a suction source, a fluid source, a sensor and/or an imaging device. The indicator may receive a signal from a sensor indicating that a measured parameter has reached an appropriate value. In response, the indicator may turn on, change color, grow brighter or change in any suitable manner to indicate that the particular procedure should be modified or halted. The indicator may also be located on a valve replacement device, a valve repair device, a power supply, a tissue-engaging device, a suction source, a fluid source, a sensor and/or an imaging device and/or may be located on another location visible to the user.

In one embodiment of the disclosure, the controller may include an audio device that indicates to the user that the delivery of suction, fluids and/or energy should be halted or adjusted, for example. Such an audio device may be, for example, a speaker that broadcasts a sound (for example, a beep) that increases in intensity, frequency or tone as a parameter sensed by a sensor increases. The user may adjust, for example, turn down or turn off power supply when the sound emitted reaches a given volume or level. In another embodiment, the audio device may also give an audible signal (such as the message "turn off energy source"), for example, when a parameter sensed by a sensor reaches a certain level. Such an audio device may be located on a valve replacement device, a valve repair device, a power supply, a tissue-engaging device, a suction source, a fluid source, a sensor and/or an imaging device, for example. In one embodiment of the disclosure, the audio device may be a separate device.

In one embodiment of the disclosure, a valve replacement device, a valve repair device, an imaging device, tissue-engaging device, a nerve stimulation device, a cardiac stimulation device, a suction, source, a fluid source, one or more sensors, a drug delivery device, a guidance device and/or a controller may be slaved to a robotic system or a robotic system may be slaved to a valve replacement device, a valve repair device, an imaging device, tissue-engaging device, a nerve stimulation device, a cardiac stimulation device, a suction, source, a fluid source, one or more sensors, a drug delivery device, a guidance device and/or a controller. Computer- and voice-controlled robotic systems that position and maneuver endoscopes and/or other surgical instruments for performing microsurgical procedures through small incisions may be used by the physician or surgeon to perform precise and delicate maneuvers. These robotic systems may allow the surgeon to perform a variety of microsurgical procedures. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

A medical procedure, e.g., a valve repair procedure, a valve replacement procedure, or a valve imaging procedure, of the present disclosure may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. The medical procedure may be a valve procedure. Alternatively, the medical procedure may be surgery performed on another organ of the body.

In one embodiment of the present disclosure, a positioning or tissue-engaging device may comprise one or more sensors and/or electrodes, e.g., sensing electrodes and/or stimulation electrodes. In another embodiment of the present disclosure, an imaging device may comprise one or more sensors and/or electrodes, e.g., sensing electrodes and/or stimulation electrodes. In another embodiment of the present disclosure, a positioning or tissue-engaging device may comprise imaging capabilities, e.g., ultrasound imaging, and one or more sensors and/or electrodes, e.g., sensing electrodes and/or stimulation electrodes.

In one embodiment of the present disclosure, a valve replacement device or system or a valve repair device or system may comprise one or more sensors and/or electrodes, e.g., sensing electrodes and/or stimulation electrodes. In another embodiment of the present disclosure, a valve replacement device or system or a valve repair device or system may comprise imaging capabilities, e.g., ultrasound imaging, and/or one or more electrodes, e.g., stimulation electrodes. In another embodiment of the present disclosure, a valve replacement device or system or a valve repair device or system may comprise tissue-positioning capabilities, e.g., suction engagement of tissue. In one embodiment of the disclosure, a valve replacement device or system or a valve repair device or system may be guided or steerable.

In one embodiment of the present disclosure, devices, systems, and methods that may be used for guidance of a medical device, e.g., a valve replacement device or a valve repair device, in a minimally invasive medical procedure, include electromagnetic devices, systems and methods, electric field devices, systems and methods, and ultrasound devices, systems and methods. Examples of various tracking, monitoring, positioning, guiding and/or navigating technologies are disclosed in U.S. Pat. Nos. 5,782,765; 6,190,395; 6,235,038; 6,379,302; 6,381,485; 6,402,762; 6,434,507; 6,474,341; 6,493,573; 6,636,757; 6,669,635; 6,701,179; 6,725,080, the entire disclosures of which are incorporated herein by reference.

A guidance device, system, and/or method that may be used according to one embodiment of the disclosure include the use of electrical fields, for example, electric fields passing in three axes through a patient's body. In one embodiment, three pairs of sensors, e.g., electrode patches, are positioned in electrical contact with the patient's body. In one embodiment, one set of the electrode patch sensors are oriented in each of the three axes, side-to-side, front-to-back, and head-to-toe, e.g., electrode patch sensors located on neck and thigh. A 40.1 KHz, 40.2 KHz, and 40.3 KHz signal is transmitted, for example, between each of the three sets of electrode patch sensors, respectively. The three signals transmitted between the electrode patch sensors, may be picked up by sensors, e.g., electrodes, positioned on medical devices placed within the patient's body, e.g., within the patient's cardiovascular system or thoracic cavity. Sensor electrodes that are in contact with electrically conductive tissue and/or fluids, e.g., blood, may be monitored from outside of the body via the three signals transmitted between the three pairs of electrode patch sensors, since there will be a voltage drop across each of the three inter-patch spaces within the body associated with electrodes of the medical devices. The voltage drop may be used to calculate the location of the monitored sensor electrode(s) in 3-D space within the patient's body. One embodiment of an electric field guidance device may track the position of up to 10 sensor electrodes simultaneously. An electric field guidance device or system may include a visual monitor or display to display electrode locations or positions. For example, the monitored sensor electrodes may be shown on a three axis coordinate grid on a monitor or display. In one embodiment, the electric field guidance device achieves the best accuracy when the electric field gradients are uniform. Distortions to the electric fields may cause inaccuracies in the rendered position of the electrodes. Electric field distortions may be caused by air voids, for example, within the thoracic cavity. Therefore, sensor electrodes that are being tracked should maintain contact with conductive tissue and/or fluids to have their positions monitored continuously, for example, on the coordinate system.

A guidance device, system, and/or method may use one or more imaging devices to acquire images, for example, previously acquired ultrasound, CT, MRI, PET, fluoroscopy and/or echocardiography images, to provide real-time medical device monitoring, positioning, tracking and/or guidance. Previously acquired images may be registered to the patient. For example, acquired images of anatomical structures of the patient may be accurately registered to the patient's anatomy in real-time. The guidance device or system may then show, for example, on a visual monitor or display, the locations or positions of the medical device sensors relative to a previously acquired image or images, thereby providing real-time monitoring, positioning, tracking and/or guidance of the medical device or devices relative to an image or images of the patient's anatomy.

A guidance device, system, and method that may be used according to one embodiment of the disclosure include the use of a magnetic field. In one embodiment, sensors comprising three small coils are positioned and oriented in three different axes of a medical device, e.g., a valve replacement device or system or a valve repair device or system, and a sensor, e.g., an antenna pad, is placed in contact with the patient's body, for example, the antenna sensor pad is placed under the patient. The magnetic field guidance device and method senses the 3-D location of the three sensor coils of the medical device. The 3-D location of the sensor coils may then be displayed or represented on a visual monitor or display, for example, as shown on a three axis coordinate grid. Again, the guidance device, system, and/or method may use one or more imaging devices to acquire images to provide real-time medical device monitoring, positioning, tracking and/or guidance. For example, a device comprising sensor coils may be monitored as the portion of the device comprising the sensor coils is moved around a space, cavity or chamber, e.g., a cardiac chamber, within the patient. The geometry of the space, cavity or chamber may then be mapped and displayed, for example, on a visual monitor or display. The accuracy of the geometric mapping of a space, cavity or chamber is generally related to the number of data points collected or monitored. A magnetic field guidance device or system is generally not sensitive to air voids within the patient's body.

A guidance device and method that may be used according to one embodiment of the disclosure includes the use of ultrasound. In one embodiment, sensors comprising ultrasound transducers are incorporated into a medical device, e.g., a valve replacement device or system or a valve repair device or system. The ultrasound transducer sensors of the medical device to be tracked emit ultrasonic energy. The ultrasonic energy is then received by ultrasonic transducer sensors on other devices within the patient's body or in contact with the patient's body. The ultrasound guidance device may then display the relative positions of one or more of the ultrasound transducer sensors and renders images of the devices incorporating the ultrasound transducer sensors. Again, the guidance device, system, and/or method may use one or more imaging devices to acquire images to provide real-time medical device monitoring, positioning, tracking and/or guidance. The 3-D location of the ultrasound transducer sensors may be displayed or represented on a visual monitor or display, for example, as shown on a three axis coordinate, grid layered onto a previously acquired image. The ultrasound guidance device or system can be very sensitive to air voids or differences in the speed of sound within various types of tissues and/or fluids.

A guidance device, system, and method that may be used according to one embodiment of the disclosure include the use of an electromagnetic field transmitter that may be coupled to an image intensifier of a fluoroscopic imaging device, e.g., a fluoroscope. In one embodiment, the guidance device or system may transmit three alternating magnetic fields that may be received by coils within the field of interest. The electromagnetic field transmitter may contain a matrix of small metal spheres that may be used to normalize a fluoroscopic image. In one embodiment, fluoroscopic images are acquired in one or more directional orientations using a fluoroscopic imaging device or system. The acquired images are then viewed by a physician who is then able to track and guide a medical device within the field of interest. In one embodiment, each medical device tracked and/or guided comprises at least one receiving sensor coil that allows the medical device to which it is attached to be tracked in 3D space with respect to the previously acquired fluoroscopic image or images.

In embodiment of the present disclosure, previously acquired images, e.g., images of a patient's thoracic cavity, acquired by one or more imaging devices may be displayed while displaying images and precise locations of one or more medical devices inserted into the patient, e.g., the patient's thoracic cavity. The medical devices may be hand held, manually controlled, remotely controlled, e.g., by magnetic fields, and/or robotically controlled. Each medical device that is to be tracked in real-time comprises at least one sensor coil. In one embodiment, electromagnetic navigation or guidance technology utilizes a system that transmits three separate electromagnetic fields that are sensed by a single sensor coil or multiple sensor coils mounted on the medical device to be tracked. In one embodiment, each medical device to be monitored and/or tracked in 3-D space requires at least one sensor coil. Additional medical device sensor coils may provide details regarding the shape and/or path of the medical device, for example. The shape of a flexible and/or articulating portion of a medical device may be provided via sensor coils positioned on or within the flexible and/or articulating portion. For example, an elongated flexible member of a medical device may have multiple sensor coils positioned along its length. In one embodiment, accurate registration of a previously acquired anatomical image may be performed using surface fiducial registration points as well as internal, implanted and/or indwelling reference devices. The form of reference points required to register the image to the true anatomy may depend on the accuracy needed for the particular procedure and anatomy of interest. In terms of information management to the physician or surgeon, one embodiment of this disclosure couples visual imaging, e.g., endoscopic imaging, with navigation or guidance through the virtual anatomy.

One embodiment of the present disclosure involves first imaging of the patient's area of interest, e.g., the patient's thoracic cavity anatomy, using, for example, one or more plane fluoroscopy, computed tomography (CT), magnetic resonance (MR) imaging, and/or one or more plane 2-D or 3-D ultrasound imaging prior to the procedure. The initial imaging may be carried out by first placing fiduciary markers on specific points on or in the patient's body. The fiduciary markers may be easily identified on the images via use of one or more contrast agents or materials identifiable to the particular imaging technique used. The fiduciary markers may be attached to the skin, positioned subcutaneously, implanted, positioned in the trachea, bronchi, and/or esophagus, or may be inserted into the cardiovascular system, for example. In one embodiment, a medical device, e.g., a catheter or catheter-like device, having multiple sensor coils may be placed through the venous system through the inferior vena cava and/or superior vena cava and extended into various additional portions of the right side of the heart, e.g., the right atrial appendage, the coronary sinus, the right ventricle, the inter-ventricular septum, the right ventricular apex, the right ventricular outflow tract, and/or the pulmonary arteries. In one embodiment, delivery to sites such as the pulmonary arteries may be aided by the addition of a balloon positioned at or near the distal end of the fiduciary marking device to make use of blood flow to force the device downstream into the distal end of the right side of the cardiovascular system and into one or more of the pulmonary arteries. Additionally, such a fiduciary marking device may be placed in the arterial side of the cardiovascular system, whereby it may be introduced via an artery into the ascending aorta and extended through the descending aorta (or into superior arterial vessels) and into the aortic valve, the left ventricle, the inter-ventricular septum, the left ventricular apex, the mitral valve annulus, the left atrium, the left atrial appendage, and/or the pulmonary veins. In one embodiment, on or more fiduciary devices inserted into the esophagus and/or trachea may be used to track in-real time respiration effects on the posterior aspects of the heart. One or more reference sensor coils or marking points may be incorporated into a tracheal tube used for a patient on a respirator. One or more reference sensor coils or marking points may be incorporated into an esophageal tube. An esophageal reference may provide information of the location or position of the esophagus during procedures.

In one embodiment, the guidance device or system may include one or more fiducial marking and/or reference devices. The fiducial marking and reference devices may be placed, for example, in and around the heart, e.g., endocardially, epicardially and/or in the pericardial space, to define the real-time precise location of the heart's surfaces and structures. An imaging device may be used to perform an imaging technique while one or more fiduciary marking and reference devices are positioned at one or more locations. Imaging may be performed with regard to respiration and/or cardiac cycle of the patient, such that the motions associated with respiration and/or the beating of the heart may be accounted for during the timing of the acquisition of the images. Placement of fiduciary marking and reference devices may be determined by the physician according to the anatomy of interest where the highest accuracy of the medical devices with respect to the anatomical structures is required. Placements of fiduciary marking and reference devices may be performed using fluoroscopy.

In one embodiment, the guidance device or system may be used during a heart valve replacement or repair procedure. For example, a pulmonic valve replacement procedure using a transvascular approach may involve preliminary imaging with an imaging device, wherein imaging is performed with skin surface fiduciary markers and a fiduciary marking catheter device placed through the venous system into the right ventricular outflow tract and to the site of the pulmonic valve annulus. After the preliminary imaging is complete and the patient is in the operating room, the pre-acquired image is then registered to the patient using the surface fiduciary markers as well as the internal catheter to provide high accuracy in the region of critical interest at the pulmonic valve annulus. The fiduciary catheter device may then be removed and a valve delivery and deployment device may be advanced into the site of the pulmonic valve for delivery and deployment of a replacement valve. During valve delivery and deployment, a physician may use the image guidance navigation device or system to view the real-time location and advancement of the valve delivery and deployment device and to view its motion through the cardiovascular system all the way to the site of deployment at the pulmonic valve annulus, for example.

In one embodiment, the guidance device or system may be used during a minimally invasive procedure or a transcatheter procedure. In one embodiment of the present disclosure, the procedure may be performed from the right side of the patient or the left side of the patient. One or more structures that may be of interest to a physician or surgeon upon entry into a patient's thoracic cavity, e.g., entry through a small incision or port access, may be the location of the pericardial sac and associated structures such as the phrenic nerve. Also of interest may be the location and courses of the caval veins, i.e., the inferior and superior vena cava, the pulmonary arteries, and/or the pulmonary veins. In one embodiment, the caval veins and other structures may be registered to one or more pre-acquired images using fiducial marking devices placed in the venous cardiovascular system. In one embodiment, the pericardial reflections that are located between the superior pulmonary veins are separated. In this region, a surgeon must be careful to avoid damage to the atrial walls, pulmonary veins, and in particular, the pulmonary arteries. Therefore, it may be advantageous to place a fiduciary marking device into one or more of the pulmonary arteries to ensure precise registration of these structures upon start of the procedure in the operating room. Such precise location registration may greatly aid the surgeon in performance of the dissections of these pericardial reflections. In one embodiment, the location of the lung surface may be of interest. In one embodiment, the tracking of the lung surface may be performed via placement of one or more devices comprising one or more tracking sensor coils on the surface of the lung. In one embodiment, an imaging device, e.g., an endoscopic camera and/or light guide, may be used to allow visual imaging of the surgical site or sites. The imaging device may be used to produce one or more images that may be displayed on a monitor. The one or more images may be coupled with the visual display produced from a guidance or navigation device or system. The imaging device may comprise one or more sensor coils, thereby allowing at least a portion of the imaging device to be tracked and/or guided in 3-D space by the guidance or navigation device or system. The visual display produced by the guidance device may be coupled in an appropriate manner to the visual display produced by the imaging device, thereby providing a physician with real-time monitoring of the imaging device and, thereby providing additional information to allow the physician to easily identify anatomical structures located in the viewing area of the imaging device. In one embodiment, imaging devices may be equipped with one or more sensor coils of a guidance system, thereby allowing distal and proximal portions to be identified easily. For example, flexible and/or deflectable medical devices may require multiple sensors, e.g., sensor coils, to define the location and path of multiple portions of the medical device, e.g., the proximal and distal portions of a flexible and/or deflectable distal medical device.

In one embodiment, sensors may be incorporated in one or more medical devices. A sensor may be attached or coupled directly to the surface of a medical device. A sensor may be incorporated into a medical device. A sensor may be incorporated into a removable sheath, cover or insert that may be placed over or inserted into at least a portion of a medical device. A removable sensor sheath, cover or insert may be disposable or re-useable. A sheath or cover may serve to protect one or more portions of a medical device from one or more body fluids and/or tissues. A sheath or cover may comprise one or more lumens that allow suction, irrigation, and/or passage of guide-wires, catheters or similar flexible, and/or polymeric devices through the sheath and into the working region at the distal end of the medical device.

In one embodiment, the guidance device or system may be used during a procedure of guiding, delivery and placement of a valve bioprosthesis or guiding, delivery and repair of a valve. In one embodiment, an imaging device or system may be used to acquire a detailed CT or MRI scan of one or more cardiac structures, for example, one or more valves. In one embodiment, an imaging device or system may be used to acquire a detailed CT or MRI scan of one or more arteries, for example, the carotid, brachiocephalic trunk, subclavian, bronchial, phrenic, hepatic, cephalic trunk, splenic, mesenteric, renal, lumbar, and iliac arteries. It can be important to identify these branch arteries and their locations prior to a particular medical procedure so as to not to occlude any of them during the medical procedure. In one embodiment, the valve replacement delivery device or valve repair delivery device may be equipped with one or more sensor coils to allow precise tracking and guidance of the delivery system through the aortic anatomy. A previously acquired image may be critical in determining the optimal valve placement or repair site.

In one embodiment of the disclosure, one or more images of a patient's anatomy may be produced using one or more imaging device, e.g., an x-ray device, a fluoroscopy device, a CT device, a MRI device, a PET device and/or an ultrasound imaging device. These images may be used in combination with tracked positions of one or more medical devices placed in a patient. These medical devices, e.g., a valve replacement device or a valve repair device, may be tracked using one or more guidance devices comprising, for example, one or more sensors. The medical devices may also comprise one or more sensors. In one embodiment of the disclosure, a computer generated display showing a medical device's position created by a guidance device or system may be superimposed on a previously acquired image or images produced by one or more imaging devices. In one embodiment of the disclosure, a guidance device or system may include one or more imaging devices. In one embodiment of the disclosure, a guidance device or system may include a controller, e.g., a controller as discussed above. In one embodiment of the disclosure, a guidance device or system may include one or more sensors, e.g., wherein the sensors are coupled to a controller. In one embodiment of the disclosure, a guidance device or system may be slaved to a robotic system or a robotic system may be slaved to a guidance device or system.

In one embodiment of the disclosure, a method of real-time image registration includes monitoring in real-time fixed surface and indwelling fiduciary marking devices so as to update and correct the registration of previously acquired images, e.g., x-ray images, fluoroscopy images, CT images, Mill images, PET images and/or ultrasound images, thereby providing real-time changes in position of the anatomical structures of interest, e.g., respiration, cardiac motion, and intestinal peristalsis.

In one embodiment of the disclosure, a guidance device or system may comprise an electrical sensor, a magnetic field sensor, an optical sensor, an acoustic sensor and/or an inertial sensor. In one embodiment of the disclosure, a guidance device or system may comprise a magnetic field generator. In one embodiment of the disclosure, a sensor coil may comprise an electrically conductive, magnetically sensitive element that may be responsive to time-varying magnetic fields for generating induced voltage signals as a function of, and representative of, the applied time-varying magnetic field.

One embodiment of the disclosure comprises a valve replacement device or valve repair device and one or more sensors, e.g., receiving sensor coils that allow electromagnetic tracking and navigation in 3-D space of the location of one or more portions of the devices. In one embodiment of the disclosure, the valve replacement device is a valve replacement delivery device or system. In one embodiment of the disclosure, the valve replacement device is a replacement valve. In one embodiment of the disclosure, the valve repair device is a valve repair delivery device or system. In one embodiment of the disclosure, the valve repair device is an implantable valve repair device. In one embodiment of the disclosure, the valve replacement device or valve repair device is a surgical device. In one embodiment of the disclosure, the valve replacement device or valve repair device is a minimally invasive device and/or an endoscopic device. In one embodiment of the disclosure, the valve replacement device or valve repair device is a transcatheter device. In one embodiment of the disclosure, the valve replacement device or valve repair device comprises one or more portions that are flexible, articulating, malleable and/or rigid.

One embodiment of the disclosure includes one or more fiduciary marking or reference devices that may be used to update and correct the registration of previously acquired images, e.g., x-ray images, fluoroscopy images, CT images, Mill images, PET images and/or ultrasound images, thereby providing real-time changes in position of the anatomical structures of interest, e.g., respiration, cardiac motion, and intestinal peristalsis. In one embodiment, a fiduciary marking or reference device is visualizable and/or detectable by one or more means of non-invasive imaging such as x-ray, fluoroscopy, computed tomography, magnetic resonance, PET and/or ultrasound imaging. In one embodiment, the fiduciary marking or reference device may include one or more sensors, e.g., sensor coils, thereby allowing the device's location in 3-D space to be easily determined and used as a reference and/or real-time registration point or points for tracking, navigation and/or guidance, e.g., electromagnetic tracking, navigation and/or guidance, in 3-D space.

One embodiment of the disclosure includes a fiduciary reference or marking device which may be fixed in location on or within a patient's body via an adhesive, a tissue fixation screw, helix, barb and/or hook, a suction source, an inflatable balloon, an expandable structure, and/or via physical pressure.

One embodiment of the disclosure includes an esophageal device that comprises one or more sensors, e.g., receiving sensor coils, which allow determination of the location of the esophageal device in 3-D space. One embodiment of the disclosure includes a trans-esophageal device, e.g., a trans-esophageal imaging device and/or a trans-esophageal stimulation device, which comprises one or more sensors, e.g., receiving sensor coils, which allow determination of the location of the trans-esophageal device in 3-D space.

One embodiment of the disclosure includes a tracheal device that comprises one or more sensors, e.g., receiving sensor coils, which allow determination of the location of the tracheal device in 3-D space. One embodiment of the disclosure includes a trans-tracheal device, e.g., a trans-tracheal imaging device and/or a trans-tracheal stimulation device, which comprises one or more sensors, e.g., receiving sensor coils, which allow determination of the location of the trans-tracheal device in 3-D space.

One embodiment of the disclosure includes a vascular device that comprises one or more sensors, e.g., receiving sensor coils, which allow determination of the location of the vascular device in 3-D space. One embodiment of the disclosure includes a trans-vascular device, e.g., a trans-vascular imaging device, a trans-vascular stimulation device, a trans-vascular valve replacement device and/or a trans-vascular valve repair device, which comprises one or more sensors, e.g., receiving sensor coils, which allow determination of the location of the trans-vascular device in 3-D space.

One embodiment of the disclosure includes a guiding device, e.g., a guiding catheter device, which comprises one or more sensors, e.g., receiving sensor coils, which allow determination of the location of the guiding device in 3-D space. One embodiment of the disclosure includes a catheter-like insert device, which may be inserted through the lumen of a larger catheter device, the catheter-like insert device comprising one or more sensors, e.g., receiving sensor coils, which allow determination of the location of the catheter-like insert device in 3-D space.

One embodiment of the disclosure includes a stimulation device that comprises one or more sensors, e.g., receiving sensor coils, which allow determination of the location of the stimulation device in 3-D space. One embodiment of the disclosure includes a nerve stimulation device, e.g., a vagal nerve stimulation device, which comprises one or more sensors, e.g., receiving sensor coils, which allow determination of the location of the nerve stimulation device in 3-D space.

One embodiment of the present disclosure includes a tissue-engaging device that comprises one or more sensors, e.g., receiving sensor coils, which allow determination of the location of the tissue-engaging device in 3-D space. One embodiment of the present disclosure includes a tissue dissection device, which comprises one or more sensors, e.g., receiving sensor coils, which allow determination of the location of the tissue dissection device in 3-D space. One embodiment of the disclosure includes a tissue retraction device, which comprises one or more sensors, e.g., receiving sensor coils, which allow determination of the location of the tissue retraction device in 3-D space.

One embodiment of the disclosure includes a valve replacement device or system that comprises one or more sensors, e.g., receiving sensor coils, which allow determination of the location of the valve replacement device or system in 3-D space. One embodiment of the disclosure includes a valve replacement delivery device or system that comprises one or more sensors, e.g., receiving sensor coils, which allow determination of the location of the valve replacement delivery device or system in 3-D space.

One embodiment of the disclosure includes a valve repair device or system that comprises one or more sensors, e.g., receiving sensor coils, which allow determination of the location of the valve repair device or system in 3-D space. One embodiment of the disclosure includes a valve repair delivery device or system that comprises one or more sensors, e.g., receiving sensor coils, which allow determination of the location of the valve repair delivery device or system in 3-D space.

A medical procedure according to one embodiment of the present disclosure may be a non-invasive, minimally invasive and/or invasive procedure. In one embodiment, the medical procedure may entail a port-access approach, a partially or totally endoscopic approach, a sub-xyphoid approach, a sternotomy approach and/or a thoracotomy approach. In one embodiment, the medical procedure may entail a trans-vascular procedure, a percutaneous procedure and/or a transcatheter procedure. The medical procedure may include the use of various robotic, imaging systems, and/or guidance systems. The medical procedure may be a procedure comprising the heart, e.g., valve replacement and/or valve repair. Alternatively, the medical procedure may be a procedure comprising another organ of the body. The medical procedure may be a procedure comprising more than one organ of the body. In one embodiment, on or more medical devices of the present disclosure may be positioned and used, for example, through a sternotomy, through a thoracotomy that avoids the sternal splitting incision of conventional cardiac surgery, through a mini-thoracotomy, through a sub-xyphoid incision, percutaneously, transvenously, arthroscopically, endoscopically, for example, through a percutaneous port, through a stab wound or puncture, through a small or large incision, for example, in the chest, in the groin, in the abdomen, in the neck or in the knee, or in combinations thereof. In one embodiment, on or more medical devices of the present disclosure may be guided into a desired position using various imaging and/or guidance techniques as described herein.

Figure 13:
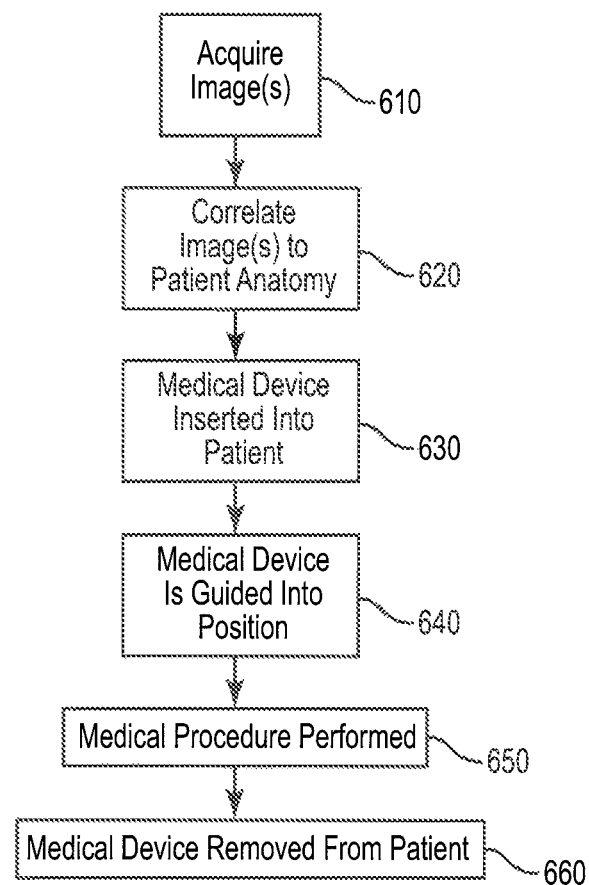
FIG. 13 is a flow diagram of one embodiment of the disclosure.

One embodiment of a method according to the present disclosure is outlined in FIG. 13. An imaging device acquires one or more images, as described herein, of a patient's anatomy of interest at 610. Next an image guidance system comprising reference markers, as described herein, is used to correlate the acquired image(s) with the patient's anatomy at 620. A medical device, e.g., a valve replacement device or system and/or a valve repair device or system, comprising one or more image guidance sensors is then inserted into the patient at 630. The medical device is then guided into a desired position, e.g., adjacent cardiac tissue, using the image guidance system at 640. A medical procedure, e.g., a valve replacement procedure or a valve repair procedure comprising the replacement of a cardiac valve or repair of a cardiac, is performed at 650. The medical device, or a portion thereof, is removed from the patient at 660.

Figure 14:
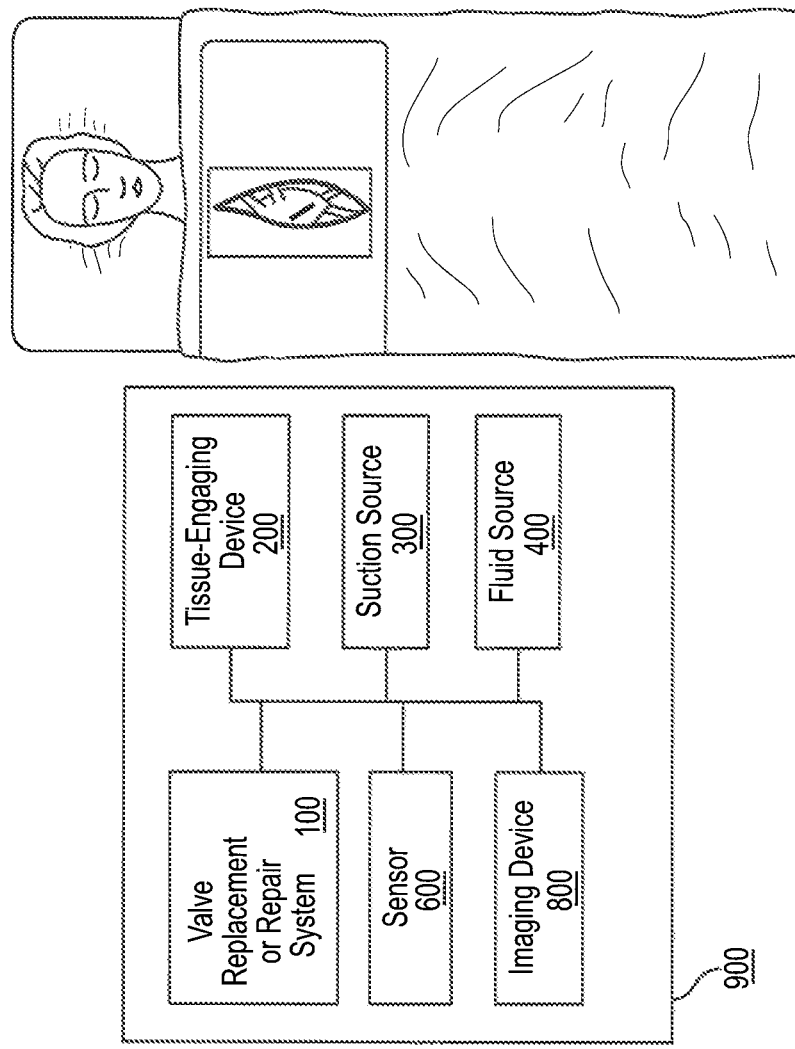
FIG. 14 is a schematic view of one embodiment of a system in accordance with the disclosure.

FIG. 14 shows a schematic view of one embodiment of a system 900 for replacing or repair one or more cardiac valves. In this embodiment, system 900 is shown to comprise a valve replacement or repair system 100, a tissue-engaging device 200, a suction source 300, a fluid source 400, a sensor 600 and an imaging device 800. The valve replacement or repair system 100 may include a valve replacement delivery device or system or a valve repair delivery device or system. In one embodiment of the disclosure, the valve replacement or repair delivery systems may comprise a power supply and/or a controller. System 900 may also include a drug delivery device, a guidance device, a nerve stimulation device and/or cardiac stimulation device (all not shown in FIG. 14). The tissue-engaging device may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere to engage or grasp tissue via suction. In one embodiment of the disclosure, the tissue-engaging device may be used to position, manipulate, hold, grasp, immobilize and/or stabilize tissue in accordance with the present disclosure. The drug delivery device may be used to deliver drugs and/or biological agents to a patient. The imaging device may be used to image or illuminate a tissue site. The imaging and guidance devices may be used to help control and guide one or more components of system 900 during a medical procedure. In one embodiment of the disclosure, a valve replacement device or system or a valve repair device or system may comprise a tissue-engaging device.

A high intensity focused ultrasound ablation or stimulation assembly or system 1000 for use in the methods of the present invention is illustrated in FIG. 15 and is similar to the high intensity focused ultrasound stimulation assembly described in parent U.S. patent application Ser. No. 09/487,705 and prior U.S. patent application Ser. No. 09/487,710, the disclosures of which are incorporated herein by reference. The high intensity focused ultrasound ablation or stimulation assembly 1000 includes a focused ultrasound ablation or stimulation device 1012, a power supply 1014 and a controller 1016. The focused ultrasound ablation or stimulation device 1012 is similar to that described in U.S. patent application Ser. Nos. 09/487,705 and 09/487,710 and includes a focused ultrasound emitting member 1018, an elongate handle shaft or body 1020 having a distal end at which the ultrasound emitting member is disposed and a handle or handpiece 1022 coupled to a proximal end of the handle shaft 1020. As shown in FIGS. 16 and 17, the ultrasound emitting member includes a transducer 1024 carried by or within a housing, carrier or case 1026. The transducer, which includes one or more individual ultrasound emitting elements or transducer elements, is capable of generating and emitting ultrasound energy in response to being supplied with electrical power from power supply 1014. In the case of ultrasound emitting member 1018, the transducer includes a plurality of individual ultrasound emitting elements or transducer elements 1028, each including a piezoelectric element that vibrates to produce ultrasound energy when an electrical current or signal is supplied thereto. The transducer elements 1028 have a focusing configuration or geometry that results in the ultrasound energy produced thereby being focused a fixed distance from the ultrasound emitting member. The transducer elements 1028 have a partial spherical or concave configuration causing the ultrasound energy generated thereby to be focused, as shown by arrows in FIG. 17, at focusing zones F, respectively.

The transducer elements 1028 are arranged in an array on or in housing 1026 and, therefore, the transducer 1024 may be considered a multi-array transducer. In the case of ultrasound emitting member 1018, the transducer elements are arranged in a planar array of three rows R and six columns C, although the transducer elements can be arranged in any number of rows and columns. In the case of focused ultrasound emitting member 1018, each row R has an equal number of transducer elements, and each column C has an equal number of transducer elements. It should be appreciated that any number of transducer elements can be provided in each row and column and that the number of transducer elements provided in each row and column can be the same or different.

The transducer elements 1028 can be referenced by their location in the array. For example, the transducer element 1028' in the first row, first column can be designated transducer element R1C1, the transducer element 1028" in the first row, second column can be designated transducer element R1C2 and so on. The transducer elements may be disposed as close as possible to one another; however, it should be appreciated that the spacing between the individual transducer elements 1028 of the array can vary so that adjacent transducer elements can be disposed closer together or further apart from one another. As explained further below, the transducer elements 1028 are selectively, independently actuatable to selectively emit or not emit ultrasound energy.

The transducer elements 1028 can be designed in various ways as known in the art. In the case of transducer 1024, the transducer elements each comprise a piezoelectric element formed by a layer of piezoelectric material carried by housing 1026. The piezoelectric elements are recessed from a planar external lower or bottom surface 1032 of housing 1026. The piezoelectric elements are curved in a direction inwardly of surface 1032 such that ultrasound energy generated by the piezoelectric elements is emitted from focused ultrasound emitting member 1018 in a direction perpendicular to surface 1032 for focusing at the focusing zones F, which are spaced outwardly of surface 1032. Accordingly, surface 1032 is an active surface or face of the ultrasound emitting member which, when positioned externally on, adjacent or in contact with skin S, results in the ultrasound energy emitted by the transducer being focused at zones F, which will be disposed within the skin S as shown in FIG. 17. When the ultrasound emitting member is positioned on, against or adjacent the skin S at a location aligned with a designated target area 1034 within the skin S, the target area 1034 being shown in dotted lines in FIGS. 17 and 18, the focusing zones will be disposed at or within the target area as best shown in FIG. 17.

Each focusing zone F consists of a single point or a plurality of points forming a zone at which the ultrasound energy is focused. Each focusing zone is in line with a central axis of the corresponding transducer element. Each focusing zone is disposed a fixed predetermined distance from a plane containing the active face 1032, the predetermined distance for each focusing zone being perpendicular or normal to the active face 1032. Therefore, the focusing zones F will also be disposed a predetermined perpendicular distance or a calculable or determinable perpendicular distance from an external surface 1036 of skin S with which the active face 1032 is placed in contact or adjacent thereto. Where the active face 1032 is placed in contact with the external skin surface 1036, the perpendicular distance that zones F are disposed from external skin surface 1036 will be the same as the predetermined distance. Where the active face 1032 is not placed in contact with the external skin surface 1036 but, rather, is spaced from the external skin surface 1036 by a known amount, for example, the perpendicular distance that zones F are disposed from the external skin surface will correspond to the predetermined distance minus the distance that the active face 1032 is spaced from the external skin surface 1036. Where the active face 1032 is spaced from the external skin surface 1036, an acoustic coupling medium can be disposed between the external skin surface 1036 and the member 1018.

Since the ultrasound is focused at focusing zones F, which are spaced from one another, the ultrasound is of greater or higher intensity at focusing zones F than in tissue surrounding the focusing zones F. Ultrasound energy is thusly focused or concentrated at the focusing zones F, causing the skin at the focusing zones F to be heated to an ablative temperature resulting in formation of lesions 1038 at the focusing zones, respectively. The tissue is ablated at the lesions 1038; and, as used herein, "ablated" tissue includes tissue that has been thermally damaged, altered, necrotized, denatured, destroyed, coagulated or cauterized. When all of the transducer elements 1028 are actuated, as shown in FIG. 17, heating of skin S will occur at a focusing zone F for each transducer element, resulting in formation of a lesion 1038 at each focusing zone F. The cross-sectional size of the lesions will normally depend on the width of the focusing zones. However, depending on the intensity and duration of the ultrasound energy, the lesions 1038 may "grow" or "spread" somewhat beyond the focusing zones due to thermal conduction causing the dispersal or spread of heat from the focusing zones. Therefore, depending on procedural parameters and the dimensions of the focusing zones, each lesion 1038 has a predetermined or predictable cross-sectional size, i.e. length and width, as well as depth. As an example, each lesion 1038 spreads radially outwardly somewhat from the corresponding focusing zone. The lesions 1038 have a generally circular surface or cross-sectional configuration as shown in FIGS. 17 and 18 and a specific depth as shown in FIG. 17. Depending on procedural parameters, the dimensions of the focusing zones and/or the type of tissue being ablated, the lesions may or may not have a uniform cross-section along their depth. Where the focusing zones are sufficiently close together, and where the intensity of the ultrasound energy emitted from the transducer elements is sufficiently high and is applied to the tissue for a sufficient duration, the individual lesions may merge to form a single continuous lesion at the target area so that the target area is filled with ablated tissue. However, depending on the spacing between the focusing zones, and depending on the intensity of the ultrasound energy emitted from the transducer elements and the duration of ultrasound energy delivery to the tissue, the lesions 1038 may remain separate, discrete and not connected to one another as shown in FIGS. 17 and 18 so that the target area 1034 contains unablated skin tissue and the lesions 1038 at which the tissue of the skin is ablated. FIG. 18 illustrates a lesion 1038 formed in skin S for each focusing zone F wherein the lesions 1038 are disposed within the target area 1034 but do not merge with, contact, overlap or abut one another. Rather, each lesion 1038 is surrounded or circumscribed perimetrically by unablated skin tissue. The non-contacting lesions 1038 and unablated skin tissue are contained in an ablated tissue area 1035 at, coincident, coextensive or aligned with the target area 1034.

When all of the transducer elements 1028 are actuated, an ablated tissue area of specific surface or cross-sectional configuration and size is created within the skin S for the transducer 1024 in accordance with the configuration and size of the array, the intensity level of the emitted ultrasound energy, the duration or time of ultrasound energy delivery to the skin, and the size of the lesions. Accordingly, an ablated tissue area having a specific cross-sectional length, width and depth is formed in the skin, with the perimeter of the ablated tissue area circumscribing the array of lesions 1038. FIGS. 17 and 18 illustrate, in dotted lines, the ablated tissue area 1035 formed in skin S when all of the transducer elements are actuated. The ablated tissue area 1035 has a generally rectangular surface or cross-sectional configuration or area with a predetermined cross-sectional length and width shown in FIG. 18 and a predetermined cross-sectional depth, shown in FIG. 17, the cross-sectional depth corresponding to the depth of the lesions 1038. When the ultrasound emitting member 1018 is positioned on, against or adjacent the skin S at a location aligned with a designated target area 1034 in the skin, the ablated tissue area 1035 will be formed at or coincide with the target area as shown in FIGS. 17 and 18. The ablated tissue area is surrounded, bordered or circumscribed perimetrically by unablated skin tissue, as well as having unablated skin tissue above and below it. Since the focusing zones F begin the predetermined distance or the calculable or determinable distance below the external skin surface 1036, the ablated tissue area 1035 is an internal or subsurface ablated tissue area beginning the predetermined distance or the calculable or determinable distance beneath the external skin surface. Accordingly, the lesions 1038 and ablated tissue area 1035 begin at a beginning or starting margin 1064 located the predetermined or calculable distance below the external tissue surface 1036 and end at an ending margin 1066 disposed further below the external tissue surface than the beginning margin, the distance between the beginning and ending margins corresponding to the depth of the lesions 1038 and, therefore, the depth of the ablated tissue area 1035.

The housing 1026 can have various external configurations and sizes and can be formed by a portion of the transducer or can mount the transducer elements in various ways. The handle shaft 1020 comprises an elongate, hollow or tubular member of sufficient length to position the ultrasound emitting member 1018 at various operative sites in or on the body of a patient while the handle 1022 is maintained at a remote location, typically externally of the patient's body. The handle shaft 1020 could be solid and may comprise a bar or other shaped member. Preferably, the handle shaft 1020 is malleable as disclosed in U.S. patent application Ser. No. 09/488,844, the disclosure of which is incorporated herein by reference. The handle 1022 has a forward end coupled to the proximal end of handle shaft 1020 and has a rearward end. The handle 1022 preferably has a configuration to facilitate grasping by a surgeon or other operator. One or more controls or switches 1042 may be provided on handle 1022 to effect operation of the focused ultrasound ablation device.

One or more electrical transmission wires 1044 is/are connected to the transducer 1024 and extend through the handle shaft 1020 for connection with power supply 1014 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 1044. For example, an electrical cord of suitable length may be removably coupled between the handle 1022 and the power supply 1014. The power supply 1014 can be designed in various ways as a source or supply of electricity to activate or excite transducer 1024 to generate and emit ultrasound energy. For example, the power supply can be designed to provide high frequency alternating electrical current to the transducer via the one or more transmission wires. The power supply may include an RF generator, with or without an amplifier, providing a constant current source. Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 1042 on the handle.

In the case of focused ultrasound ablation device 1012, a transmission wire 1044 is provided for each piezoelectric element and, therefore, for each transducer element. As shown in FIG. 17, each transmission wire 1044 is connected to its corresponding piezoelectric element and to the power supply so that the transducer elements are individually driven by or supplied with current from the power supply. The transmission wires 1044 are disposed in respective passages within the housing and may be disposed within a sheath or sleeve 1046 extending through shaft 1020. However, the transmission wires can be disposed externally of the housing and/or the shaft. The transmission wires 1044 are connected to switches (not shown), respectively, for controlling the supply or transmission of current from the power supply 1014 to the piezoelectric elements, respectively. The switches can be incorporated in the ultrasound emitting member 1018, the power supply 1014 and/or the controller 1016.

The controller or control unit 1016 controls the supply of power from power supply 1014 to transducer 1024 so that the transducer can be driven to deliver various intensity levels of ultrasound energy for various durations, periods or lengths of time. In particular, the controller 1016 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 1016 and/or the controller keyboard can be used to selectively couple and decouple the individual transducer elements 1028 with the electrical drive signal or current from the power supply 1014.

Input to the controller 1016 provided by the surgeon or other medical personnel determines the transducer elements 1028 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other non-selected transducer elements can remain deactivated to prevent transmission of electrical current thereto when the power supply is actuated or switched to an "on" mode. It should be appreciated that various components and/or methodology can be incorporated in the device 1012, the power supply 1014 and/or the controller 1016 to permit selective actuation of selected ones of the transducer elements 1028 and that such components and/or methodology would be within the purview of one skilled in the art.

Various transducers can be used in the methods of the present invention. The piezoelectric elements can be made of various piezoelectric materials such as PZT crystal materials, hard lead, zirconate/lead titanium, piezoelectric ceramic, or lithium-niobate piezoceramic material. The transducer elements can be of various sizes and can have various focusing geometries. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of the skin to be effected in response to the application or delivery of ultrasound energy to the skin for a relatively short duration or length of time. In accordance with the present invention, the duration or length of time for ultrasound energy delivery or application to the skin preferably ranges from 2 to 60 seconds depending on desired lesion size and/or ablative effect.

In accordance with the methods of the present invention, high intensity focused ultrasound is used to create an internal ablated tissue area within the skin containing unablated skin tissue and a plurality of lesions at which the tissue of the skin is ablated. In reaction to the lesions, collagen growth in the skin is stimulated. In this manner, collagen levels in the skin are increased resulting in a reduction of wrinkles, enhanced skin resilience and a more youthful appearance.

The skin S, as shown in FIG. 17, includes an outer or external layer, known as the epidermis E, and an inner or internal layer, known as the dermis DE. The epidermis E is comprised of a plurality of sub-layers including several layers of stratified epithelial tissue and defines external skin surface 1036. The epidermis E has a basilar layer including melanocytes, which produce melanin serving to protect the skin from the harmful effects of ultraviolet radiation. The dermis DE, or "true skin", is comprised of connective tissue with a varying amount of elastic fibers and numerous blood vessels, lymphatics, nerves and hair follicles H. The dermis DE includes a superficial layer, known as the superficial dermis or papillary layer L, and a deep layer, known as the deep dermis or reticular layer R. The superficial layer L may itself be considered as comprising a plurality of superficial sublayers forming the superficial dermis. The reticular layer R contains collagen C and elastin, which impart firmness, flexibility and durability to the skin.

As shown in FIG. 17, the ultrasound emitting member 1018 is placed against the skin S of a patient to position the active face 1032 in contact with the external skin surface 1036. The active face is placed at or on the skin surface 1036 at a location aligned with a desired target area 1034 in the skin for creation of an ablated tissue area, such location corresponding to an area of the skin that is to be rejuvenated. The shaft 1020 may be grasped and manipulated, as necessary, to facilitate positioning of the active face at the desired location on the external skin surface. Typically, the ultrasound emitting member will be placed in contact with skin of the patient's face at a location where a reduction in wrinkles is desired, such as the forehead, cheeks, and the areas around the mouth and eyes. Also, all or specific ones of the transducer elements are selected for actuation or "firing" in accordance with the desired size and configuration for the ablated tissue area and/or the desired number of lesions to be contained in the ablated tissue area. The ablation device 1012 is programmed via the controller to effect actuation or "firing" of the selected transducer elements when electric current or a signal is supplied to the transducer. Of course, selection and programming for actuation or "firing" of selected transducer elements can be performed prior to positioning of member 1018 on the skin surface.

Once the active face is positioned in contact with the skin S at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the skin S at the corresponding focusing zones F. In the procedure of FIG. 17, all of the transducer elements are "fired" to emit ultrasound energy, causing the skin to be heated to an ablative temperature at a focusing zone for each transducer element. The skin S at the focusing zones is heated to a temperature in the range of 60 to 90 degrees Celsius for the time required to achieve ablation or thermal damage in the skin. The focusing zones are contained in the target area 1034, which is coincident with or disposed in the superficial dermis L and is thusly disposed between the epidermis E and the deep dermis R. The skin S is heated at the focusing zones to a sufficiently high temperature so as to cause a plurality of subsurface or internal lesions 1038 to be simultaneously formed in the skin S and, in particular, in the superficial dermis L, while the ultrasound emitting member 1018 remains external of and does not physically penetrate the skin S.

Lesions 1038 have a generally circular surface or cross-sectional configuration as shown in FIGS. 17 and 18 and do not contact or touch one another. Lesions 1038 contain ablated or damaged skin tissue while the skin tissue surrounding each lesion 1038 is not heated to the ablative or thermally damaging temperature and, therefore, is unablated or undamaged. In this manner, eighteen discontinuous or non-contacting individual lesions 1038 are formed in the skin as represented in FIG. 18. Lesions 1038 are contained in the internal ablated tissue area 1035 coincident with the target area 1034, the ablated tissue area 1035 containing the lesions 1038 and the unablated skin tissue between adjacent lesions 1038. The lesions 1038 have a cross-sectional length and width and a depth of known parameters depending on the size and focusing geometry of the transducer elements, the intensity of the ultrasound energy, the temperature to which the skin is heated and the duration of ultrasound energy delivery or application to the skin.

Due to the predetermined distance and the known length for the focusing zones, the lesions 1038 and, therefore, the ablated tissue area 1035, begin at the beginning or starting margin 1064 located a predetermined or known depth beneath or below the external skin surface 1036 and end at the ending margin 1066 located a greater predetermined or known depth beneath the external skin surface 1036, the distance between the beginning and ending margins corresponding to the depth of the lesions and, therefore, the depth of the ablated tissue area 1035. By selecting the appropriate focusing zone depth and treatment parameters, a desired thickness or depth of unablated or undamaged skin tissue between the beginning margin 1064 and the external tissue surface 1036 is disposed outside the ablated tissue area. Preferably, the beginning margin is located 50 to 150 micrometers below the external skin surface. In the method of FIGS. 17 and 18, a layer of unablated skin tissue about 100 micrometers thick is maintained between the external skin surface 1036 and the beginning or starting margin 1064 of the lesions 1038, thusly preserving the epidermis E of the skin S. The lesions 1038 have a depth of 50 to 150 micrometers and, preferably, a depth of about 100 micrometers, in the direction perpendicular to skin surface 1036 such that the ablated tissue area and the lesions terminate or end at the ending margin 1066 disposed a depth of about 200 micrometers beneath the external skin surface 1036 at the transducer/tissue interface. Accordingly, there is a perpendicular distance of about 200 micrometers from the external skin surface to the ending margin of the ablated tissue area such that the deep dermis R is undamaged and preserved. By selecting the appropriate focusing zone length and treatment parameters, the depth of the ending margin 1066 within the skin is controlled thusly ensuring that the ablated tissue area and lesions do not extend or extend only an insignificant amount into the deep dermis.

As shown in FIG. 18, the ablated tissue area 1035, which is surrounded above, below and perimetrically by unablated or undamaged skin tissue, has a surface or cross-sectional configuration or area of generally rectangular shape with a cross-sectional width and length varying from 3 mm to 50 mm in either dimension, i.e. 3 mm×3 mm to 50 mm×50 mm or in between, depending on the size of the area to be treated. Although the cross-sectional length and width or other external dimensions of the ablated tissue area can be determined by the locations of the "fired" transducer elements, it should be appreciated that the cross-sectional length and/or width of the ablated tissue area can alternatively be obtained by moving the member 1018 along the skin as described in U.S. patent application Ser. No. 09/487,705, the disclosure of which is incorporated herein by reference.

Depending on the desired lesion size and/or thermal effect, ultrasound energy will be delivered or applied to the skin for a duration in the range of 2 to 60 seconds. The emission of ultrasound energy by ultrasound emitting member 1018 is terminated by the surgeon or other operator once lesions of desired size or a desired amount of tissue ablation has been obtained, and the member 1018 is removed from the patient's skin. In order to terminate the emission of ultrasound energy by the ultrasound emitting member, the power supply is deactivated or switched to an "off" mode so that electrical current is no longer supplied to the selected piezoelectric elements.

The lesions 1038, which typically contain thermally damaged tissue, cause the dermis DE to be stimulated to produce collagen C in the vicinity of the lesions. The lesions 1038 are naturally assimilated or degraded and absorbed by the patient's body and are replaced by healthy skin tissue. Accordingly, the level of collagen in the patient's skin increases in the vicinity of the lesions resulting in a reduction of wrinkles, greater resiliency and a more youthful appearance.

Figure 19:
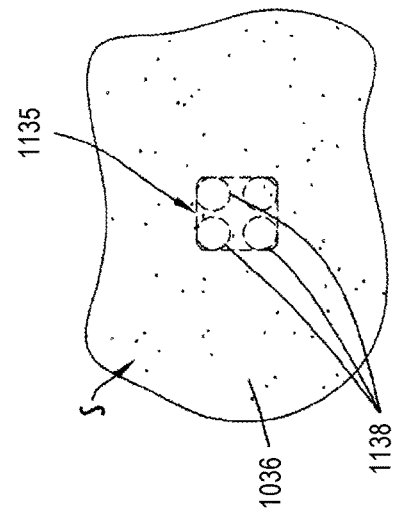
FIG. 19 is a broken top view illustrating the surface or cross-sectional configuration of an alternative ablated tissue area created in the skin.

FIG. 19 is representative of a single treatment procedure in accordance with the present invention wherein a subsurface ablated tissue area 1135 containing four non-contacting lesions 1138 is formed in the skin S. The ablated tissue area 1135 is similar to ablated tissue area 1035 except that it is of generally square surface or cross-sectional configuration or area and contains four generally circular lesions 1138 each surrounded by unablated skin tissue. The ablated tissue area 1135 can be formed using the ultrasound emitting member 1018 by selecting and "firing" transducer elements R1C1, R1C2, R2C1 and R2C2, for example, to emit ultrasound energy. As described for the procedure illustrated in FIGS. 17 and 18, the ultrasound energy emitted by the selectively "fired" or actuated transducer elements is focused in the skin at a focusing zone for each actuated transducer element, causing subsurface lesions 1138 to be formed in the skin at the focusing zones corresponding to transducer elements R1C1, R1C2, R2C1 and R2C2. The lesions 1138 are similar to lesions 1038 but are larger in diametric cross-sectional size than lesions 1038. The ablated tissue area 1135 is surrounded by unablated tissue above, below and perimetrically.

Figure 20:
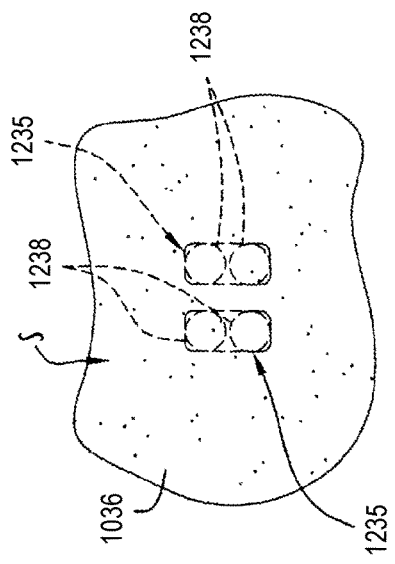
FIG. 20 is a broken top view illustrating the surface or cross-sectional configuration of a plurality of further alternative ablated tissue areas created in the skin.

FIG. 20 is representative of a multiple treatment procedure in accordance with the present invention wherein a plurality of internal ablated tissue areas 1235, each containing unablated skin tissue and a plurality of lesions 1238, are formed or created in the skin S. The ablated tissue areas 1235 are spaced from one another, and each contains two generally circular lesions 1238 similar to lesions 1138 except that lesions 1238 have a slightly larger cross-sectional diameter than lesions 1138. The lesions 1238 of each ablated tissue area 1235 are spaced slightly from one another and are surrounded by unablated skin tissue so as to be non-contacting. Each ablated tissue area 1235 has a surface or cross-sectional configuration or area of generally rectangular shape. The ablated tissue areas 1235, which are similar to ablated tissue area 1035 except for their cross-sectional configuration, can be formed using member 1018 as described above by actuating an appropriate pair of transducer elements. The ablated tissue areas 1235 are typically formed in separate treatments performed at different times. However, it should be appreciated that a plurality of ablated tissue areas, such as ablated tissue areas 1235, can be formed in the skin during a single procedure performed at one time.

Figure 21:
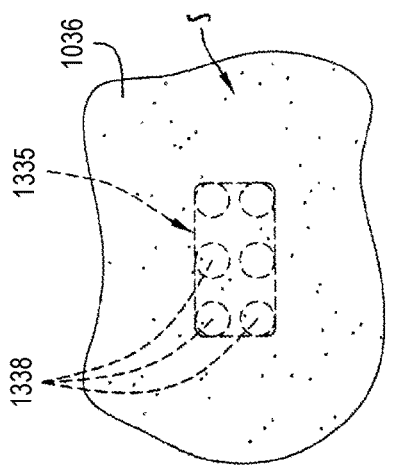
FIG. 21 is a broken top view illustrating the surface or cross-sectional configuration of another alternative ablated tissue area created in the skin.

FIG. 21 illustrates in dotted lines an ablated tissue area 1335 of rectangular cross-sectional configuration formed in the skin S and containing six generally circular non-contacting lesions 1338 each surrounded by unablated tissue. The lesions 1338 and ablated tissue area 1335 are similar to the lesions 1038 and ablated tissue area 1035 except for the cross-sectional size of lesions 1338 being different from the cross-sectional size of lesions 1038. The ablated tissue area 1335 will typically be formed in a single treatment or procedure. The ablated tissue area 1335 can be formed using the ultrasound emitting member 1018 by actuating six appropriate transducer elements.

Figure 22:
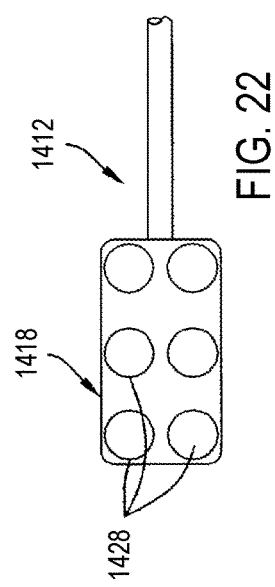
FIG. 22 is a broken bottom view of an alternative focused ultrasound ablation device having a modified ultrasound emitting member for use in the methods of the present invention.

It should be appreciated that the methods of skin rejuvenation according to the present invention can be performed using focused ultrasound ablation devices wherein the transducer elements of the ultrasound emitting members are not selectively actuatable. For example, FIG. 22 illustrates an alternative focused ultrasound ablation device 1412 having focused ultrasound emitting member 1418, which is similar to focused ultrasound emitting member 1018 except that focused ultrasound emitting member 1418 includes an array of six transducer elements 1428 actuatable simultaneously or in unison to emit ultrasound energy. The transducer elements 1428 are arranged in two rows and three columns and are used to form an ablated tissue area containing six lesions, such as ablated tissue area 1335. Accordingly, it should be appreciated that various dedicated ultrasound emitting members having different arrays and/or numbers of transducer elements can be provided, with a particular ultrasound emitting member being capable of obtaining a particular ablated tissue area of predetermined size, configuration and number of lesions in response to actuation of all of the transducer elements of the particular ultrasound emitting member.

Figure 23:
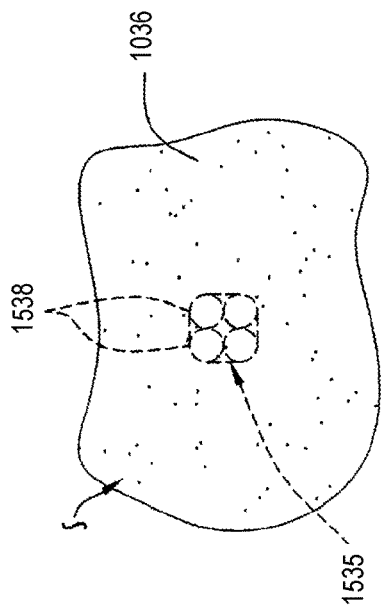
FIG. 23 is a broken top view illustrating the surface or cross-sectional configuration of an additional alternative ablated tissue area formed in the skin.

FIG. 23 illustrates an alternative, subsurface ablated tissue area 1535 formed in the skin S in a manner similar to ablated tissue area 1135. However, the ultrasound energy used to form ablated tissue area 1535 is of higher intensity and/or is applied to the skin for a longer duration than the ultrasound energy used to form ablated tissue area 1135. Accordingly, the lesions 1538 of ablated tissue area 1535 have a generally circular surface or cross-sectional configuration larger in diameter than the generally circular cross-sectional configuration of lesions 1138 due to greater dispersal of heat from the focusing zones. As a result, the lesions 1538 contact or touch one another but still do not merge sufficiently to fill the entire ablated tissue area 1535 with ablated tissue. Although each lesion 1538 is not completely surrounded perimetrically by unablated tissue, there is still some unablated tissue within the ablated tissue area 1535 as shown in FIG. 23 by unablated skin tissue disposed between adjacent lesions 1538. It should be appreciated, therefore, that the ablated tissue areas formed in accordance with the present invention can include a plurality of non-contacting lesions each completely surrounded by unablated tissue and/or a plurality of contacting lesions with unablated tissue between the contacting lesions.

In the procedures described and illustrated above, the ultrasound emitting member is placed against the skin at a desired location to form an ablated tissue area of final size and configuration in the skin with focused ultrasound energy generated and emitted by the ultrasound emitting member without moving the ultrasound emitting member from the desired location. It should be appreciated, however, that where the largest size ablated tissue area capable of being formed in the skin with the ultrasound emitting member is smaller than the final size and/or different from the final configuration desired for the ablated tissue area, the ultrasound emitting member can be moved along the skin to form an ablated tissue area of desired final size and configuration as explained in U.S. patent application Ser. No. 09/487,705, now abandoned.

Some of the advantages of the present invention are that varying intensity levels of ultrasound energy can be delivered to tissue for varying periods of time depending on desired ablative effect, the duration of ultrasound energy delivery or application to the tissue needed to accomplish a desired effect may be relatively brief depending on desired size for the lesions of the ablated tissue area and/or desired thermal effect on the tissue, the transducer or other member used to emit the ultrasound energy may be stationary or may be movable, or may be a microprocessor-controlled phased array in order to scan a target area with focused ultrasound, a plurality of individual ablated tissue areas can be formed in the tissue with the ablated tissue areas being separate and discontinuous or being contacting, abutting, contiguous or overlapping to form a single continuous ablated tissue area of desired size and/or shape, the ultrasound emitting member can remain stationary or can be moved along to scan a target area with focused ultrasound, the transducer or other member may be designed with a focusing configuration designed to ensure that the lesions of the ablated tissue area have a desired cross-sectional size, begin a desired depth within the tissue and have a desired depth, the transducer or other member is positioned externally adjacent or in contact with an external surface of the tissue or is acoustically coupled with the tissue to form an internal ablated tissue area without damaging the tissue surface and, in particular, a body cavity such as the esophagus or trachea, and an ablated tissue area of definitive size can be repeatedly and consistently produced. The esophagus is close to the posterior of the left atrium of the heart. This position makes it particularly attractive for trans-esophageal echocardiography (TEE) imaging as well as trans-esophageal ultrasound ablation.

The transducers of a phased array may be electronically controlled such that individual transducers can be controlled to interfere with the adjacent transducers. This interference can be used to "steer" the focal point of the acoustical energy to virtually any spot. For example, each element may be independently controlled and energized slightly out of phase with one another to electronically steer the focal point.

These and other objects, advantages and benefits are realized with the present invention as generally characterized in a method of tissue ablation using high intensity focused ultrasound wherein ultrasound energy is emitted from the ultrasound emitting member into the tissue to be ablated. The ultrasound energy is focused within the tissue at one or more overlapping or non-overlapping focusing zones contained in a target area. If multiple focusing zones are desired, the focusing zones are spaced from one another and, due to focusing of the ultrasound energy at the focusing zones, the ultrasound energy is of higher or greater intensity in the tissue at the focusing zones than in the tissue surrounding the focusing zones. The tissue is heated at the focusing zones by the focused ultrasound energy, thereby forming an ablated tissue area. Once an ablated tissue area of desired extent has been obtained, the ultrasound emitting member is removed.

The ultrasound emitting member has a focusing configuration causing the ultrasound energy to be focused a predetermined distance from an active face of the ultrasound emitting member. Also, the focusing configuration results in formation of lesions of predetermined or known depth in accordance with the length of the focusing zones, the selected ultrasound energy intensities and frequencies and the selected duration times for ultrasound energy delivery. The lesion depths are selected so that the lesions do not extend deeper than desired, thereby avoiding unwanted damage to surrounding tissue. The plurality of lesions may be non-contacting, with each lesion surrounded by unablated tissue. One or more of the plurality of lesions may contact another one of the plurality of lesions. The cross-sectional size of the lesions and the location and arrangement of the focusing zones in the tissue result in formation of a specific size ablated tissue area having a specific cross-sectional configuration. A single, discrete ablated tissue area or a plurality of single, discrete ablated tissue areas can be formed in the tissue in a single procedure or treatment performed at one time or in multiple procedures or treatments performed at different times. Where a plurality of ablated tissue areas are formed, the ablated tissue areas can be contiguous, contacting, overlapping or in abutment with one another so that the ablated tissue areas together form or create a single ablated tissue area of larger cross-sectional size and/or of a desired cross-sectional configuration.

One aspect of the present invention-provides a system for positioning, manipulating, holding, grasping, immobilizing and/or stabilizing an organ, such as a heart. The system may include one or more tissue-engaging devices, one or more suction sources, one or more fluid sources, one or more high intensity focused ultrasound energy devices, one or more sensors and one or more processors. The system may also include one or more imaging devices, guidance devices, drug delivery devices and/or illumination devices. A tissue-engaging device of the system may comprise a tissue-engaging head, a support apparatus and a clamping mechanism for attaching the tissue-engaging device to a stable object, such as a retractor that is fixed to a patient's chest or an operating table. A tissue-engaging device of the system may comprise one or more energy transfer elements connected to an energy source, one or more sensors connected to a processor, one or more suction openings connected to a suction source, and/or one or more fluid openings connected to a fluid source.

Another aspect of the present invention provides a method of positioning, manipulating, holding, grasping, immobilizing and/or stabilizing an organ, such as a heart. The method includes engaging and positioning an organ, such as a heart, during a high intensity focused ultrasound ablation procedure. The ablation procedure may include intermittently stimulating a vagal nerve and/or pacing a heart. The ablation procedure may include placement of a lead on or within a heart. The ablation procedure may include the use of suction to engage and position an organ, such as a heart. The ablation procedure may include the delivery of fluids, gases, and/or agents, such as drugs.

The present disclosure has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the disclosure. Thus, the scope of the present disclosure should not be limited to the structures described herein. Further, it will be appreciated by those skilled in the art that while the disclosure has been described above in connection with particular embodiments and examples, the disclosure is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

What is claimed is:

1. A method for treating a human patient, the method comprising:
    emitting ultrasound energy from an ultrasound transducer positioned remotely from target tissue of the patient, wherein the ultrasound transducer is positioned at a desired location relative to the patient and target tissue using location and imaging techniques;
    focusing the ultrasound energy such that one or more focal points are directed to the target tissue of the patient; and
    ablating the target tissue at each focal point with the focused ultrasound energy without ablating non-target tissue through which the ultrasound energy passes between the ultrasound transducer and the one or more focal points.

2. The method of claim 1, further comprising steering the focused ultrasound energy to a plurality of discrete focal points throughout the target tissue to be ablated.

3. The method of claim 2 wherein the ultrasound transducer comprises a phased array of ultrasound transducer elements, and wherein steering the focused ultrasound energy comprises electronically steering the focused ultrasound energy via microprocessor control of the phased array of ultrasound transducer elements.

4. The method of claim 3 wherein steering the focused ultrasound energy of the phased array of ultrasound transducer elements comprises electronically controlling each individual ultrasound transducer element to focus the ultrasound energy at the one or more focal points.

5. The method of claim 2 wherein steering the focused ultrasound energy comprises physically moving the ultrasound transducer relative to the patient and the target tissue.

6. The method of claim 1 wherein the ultrasound transducer is positioned at the desired location relative to the patient and target tissue using fluoroscopy.

7. The method of claim 1 wherein the ultrasound transducer is positioned at the desired location relative to the patient and target tissue using magnetic resonance imaging.

8. The method of claim 1 wherein the ultrasound transducer is positioned at the desired location relative to the patient and target tissue using direct visualization.

9. The method of claim 1 wherein the ultrasound transducer is positioned at the desired location relative to the patient and target tissue using mapping technology.

10. The method of claim 1 wherein the ultrasound transducer comprises a phased array of ultrasound transducer elements, and wherein emitting ultrasound energy from an ultrasound transducer positioned remotely from target tissue of the patient comprises emitting ultrasound energy from a first set of the ultrasound transducer elements while a second set of the ultrasound transducer elements are turned off.

11. The method of claim 1 wherein the ultrasound transducer comprises a phased array of ultrasound transducer elements, and wherein emitting ultrasound energy from an ultrasound transducer positioned remotely from target tissue of the patient comprises emitting ultrasound energy having a first phase and a first amplitude from a first set of ultrasound transducer elements, and emitting ultrasound energy having a second phase and a second amplitude from a second, different set of ultrasound transducer elements.

12. The method of claim 1 wherein emitting ultrasound energy from an ultrasound transducer positioned remotely from target tissue of the patient comprises emitting high frequency ultrasound (HIFU) energy.

13. The method of claim 1 wherein ablating the target tissue comprises ablating a non-linear area of tissue of the patient.

14. The method of claim 1 wherein ablating the target tissue comprises creating a plurality of non-linear, non-contiguous lesions within the target tissue.

15. The method of claim 1, further comprising monitoring a parameter of the ultrasound transducer and/or target tissue within the patient before and during delivery of the ultrasound energy.

16. The method of claim 15 wherein monitoring a parameter comprises monitoring changes in mechanical properties of the target tissue, and wherein the method further comprises altering delivery of the ultrasound energy in response to the monitored parameter.

17. The method of claim 1 wherein ablating the target tissue comprises ablating target nerve tissue within the patient.

18. The method of claim 1 wherein ablating the target tissue comprises ablating nerves of the patient such that neural communication along the nerves is inhibited or blocked.

* * * * *